US009504664B2

(12) United States Patent
Bannister et al.

(10) Patent No.: US 9,504,664 B2
(45) Date of Patent: *Nov. 29, 2016

(54) COMPOSITIONS AND METHODS FOR TREATING SEVERE PAIN

(71) Applicant: Infirst Healthcare Limited, London (GB)

(72) Inventors: Robin M. Bannister, Essex (GB); John Brew, Hertfordshire (GB)

(73) Assignee: Infirst Healthcare Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,599

(22) Filed: Dec. 18, 2015

(65) Prior Publication Data

US 2016/0101077 A1    Apr. 14, 2016

Related U.S. Application Data

(63) Continuation of application No. 14/155,080, filed on Jan. 14, 2014, now Pat. No. 9,265,742, which is a continuation-in-part of application No. 13/365,824, filed on Feb. 3, 2012, now Pat. No. 8,895,536, which is a continuation-in-part of application No. PCT/GB2011/052115, filed on Oct. 31, 2011, application No. 14/975,599, which is a continuation-in-part of application No. 13/365,828, filed on Feb. 3, 2012, now Pat. No. 8,895,537.

(30) Foreign Application Priority Data

| Oct. 29, 2010 | (GB) | ................................. | 1018289.7 |
| Feb. 4, 2011 | (GB) | ................................. | 1101937.9 |
| Aug. 10, 2011 | (GB) | ................................. | 1113728.8 |
| Aug. 10, 2011 | (GB) | ................................. | 1113729.6 |
| Aug. 10, 2011 | (GB) | ................................. | 1113730.4 |

(51) Int. Cl.

| *A61K 31/60* | (2006.01) |
| *A61K 31/192* | (2006.01) |
| *A61K 47/10* | (2006.01) |
| *A61K 47/14* | (2006.01) |
| *A61K 9/08* | (2006.01) |
| *A61K 47/44* | (2006.01) |
| *A61K 9/20* | (2006.01) |
| *A61K 31/196* | (2006.01) |
| *A61K 9/06* | (2006.01) |
| *A61K 31/19* | (2006.01) |

(52) U.S. Cl.
CPC ............. *A61K 31/192* (2013.01); *A61K 9/06* (2013.01); *A61K 9/08* (2013.01); *A61K 9/2013* (2013.01); *A61K 31/196* (2013.01); *A61K 31/60* (2013.01); *A61K 47/10* (2013.01); *A61K 47/14* (2013.01); *A61K 47/44* (2013.01); *A61K 31/19* (2013.01)

(58) Field of Classification Search
USPC ......................................... 514/159, 570, 571
See application file for complete search history.

(56) References Cited

U.S. PATENT DOCUMENTS

| 3,228,831 A | 1/1966 | Nicholson et al. |
| 3,800,038 A | 3/1974 | Rudel |
| 4,571,400 A | 2/1986 | Arnold |
| 4,684,666 A | 8/1987 | Haas |
| 4,918,103 A | 4/1990 | Park et al. |
| 5,011,852 A | 4/1991 | Park et al. |
| 5,059,626 A | 10/1991 | Park et al. |
| 5,154,930 A | 10/1992 | Popescu |
| 5,552,160 A | 9/1996 | Liversidge et al. |
| 5,645,856 A | 7/1997 | Lacy et al. |
| 5,955,451 A | 9/1999 | Lichtenberger et al. |
| 6,267,985 B1 | 7/2001 | Chen et al. |
| 6,294,192 B1 | 9/2001 | Patel et al. |
| 6,319,513 B1 | 11/2001 | Dobrozsi |
| 6,383,471 B1 * | 5/2002 | Chen .................... A61K 9/1075 424/401 |
| 6,451,339 B2 | 9/2002 | Patel et al. |
| 6,923,988 B2 | 8/2005 | Patel et al. |
| 7,473,432 B2 | 1/2009 | Cevc et al. |
| 8,895,536 B2 * | 11/2014 | Bannister ................ A61K 9/08 514/159 |
| 2003/0008003 A1 | 1/2003 | Jamali |
| 2003/0170279 A1 | 9/2003 | Lambert et al. |
| 2003/0232097 A1 | 12/2003 | Radhakrishnan et al. |
| 2004/0024057 A1 | 2/2004 | Earl et al. |
| 2004/0253276 A1 | 12/2004 | Sato et al. |
| 2005/0152968 A1 | 7/2005 | Brophy et al. |
| 2006/0034937 A1 | 2/2006 | Patel |

(Continued)

FOREIGN PATENT DOCUMENTS

| CN | 1736369 | 2/2006 |
| CN | 101129335 A | 8/2008 |

(Continued)

OTHER PUBLICATIONS

Csizmazia, E., et al., Penetration enhancer effect of sucrose laurate and Transcutol on ibuprofen, Journal of Drug Delivery Science and Technology, vol. 21, No. 5 Sep. 2011 XP009168551.

(Continued)

*Primary Examiner* — Pancham Bakshi
(74) *Attorney, Agent, or Firm* — One3 IP Management, P.C.; Dean G. Stathakis; Peter D. Weinstein

(57) ABSTRACT

The present specification discloses pharmaceutical compositions, methods of preparing such pharmaceutical compositions, and methods and uses of treating a chronic inflammation and/or an inflammatory disease in an individual using such pharmaceutical compositions.

21 Claims, No Drawings

(56) References Cited

U.S. PATENT DOCUMENTS

| | | |
|---|---|---|
| 2006/0062810 A1 | 3/2006 | Woo et al. |
| 2006/0078616 A1 | 4/2006 | Georgewill et al. |
| 2007/0015834 A1 | 1/2007 | Flashner-Barak et al. |
| 2007/0026062 A1 | 2/2007 | Holm et al. |
| 2007/0036831 A1 | 2/2007 | Baker |
| 2007/0104741 A1 | 5/2007 | Murty et al. |
| 2007/0190080 A1 | 8/2007 | Friedman |
| 2007/0203173 A1 | 8/2007 | Mudumba et al. |
| 2008/0153894 A1 | 6/2008 | Britten et al. |
| 2008/0154210 A1 | 6/2008 | Jordan et al. |
| 2009/0304782 A1 | 12/2009 | De Blas et al. |
| 2010/0099767 A1 | 4/2010 | Davis |
| 2010/0125060 A1 | 5/2010 | Razzak et al. |
| 2011/0142945 A1 | 6/2011 | Chen et al. |
| 2011/0195993 A1 | 8/2011 | Masson et al. |
| 2012/0270845 A1 | 10/2012 | Bannister et al. |
| 2012/0270899 A1 | 10/2012 | Bannister et al. |
| 2013/0156853 A1 | 6/2013 | Zhang et al. |

FOREIGN PATENT DOCUMENTS

| | | |
|---|---|---|
| CN | 102793628 A | 11/2012 |
| EP | 306060 A2 | 3/1989 |
| EP | 0 521344 A2 | 1/1993 |
| GB | 2331458 A | 5/1999 |
| GB | 2477590 A | 8/2011 |
| JP | 6009381 | 3/1992 |
| JP | 2008143807 | 12/2006 |
| JP | 2009155282 | 7/2009 |
| WO | 92/09272 A1 | 6/1992 |
| WO | 95/11039 A1 | 4/1995 |
| WO | 9703655 A1 | 2/1997 |
| WO | 98/25595 A2 | 6/1998 |
| WO | 00/27372 A1 | 5/2000 |
| WO | 0057859 A1 | 5/2000 |
| WO | 00/67728 A2 | 11/2000 |
| WO | 00/76478 A1 | 12/2000 |
| WO | 02/085414 A2 | 10/2002 |
| WO | 03/013566 A1 | 2/2003 |
| WO | 2004/082588 A2 | 9/2004 |
| WO | 2005/009436 A1 | 2/2005 |
| WO | 2006/096806 A2 | 9/2006 |
| WO | 2006/099325 A2 | 9/2006 |
| WO | 2006096806 A2 | 9/2006 |
| WO | 2008/070950 A1 | 6/2008 |
| WO | 2008070950 A1 | 6/2008 |
| WO | WO 2008/070950 A1 * | 6/2008 ........... A61K 31/192 |
| WO | 2008/120207 A3 | 10/2008 |
| WO | 2008/134512 A1 | 11/2008 |
| WO | 2009/033131 A2 | 3/2009 |
| WO | 2009/047785 A3 | 4/2009 |
| WO | 2009/067734 A1 | 6/2009 |
| WO | 2009/069139 A1 | 6/2009 |
| WO | 2010/059717 A2 | 5/2010 |
| WO | 2010/087947 A2 | 8/2010 |
| WO | 2010/097332 A1 | 9/2010 |
| WO | 2010/097334 A1 | 9/2010 |
| WO | 2010103312 A1 | 9/2010 |
| WO | 2011/095814 A1 | 8/2011 |
| WO | 2012/056251 A1 | 5/2012 |
| WO | 2012/104654 A1 | 8/2012 |
| WO | 2012/104655 A2 | 8/2012 |

OTHER PUBLICATIONS

Hesson Chung, et al., Oil Components Modulate Physical Characteristics and Function of the Natural Oil Emulsions as Drug or Gene Delivery System, Journal of Controlled Release 71:339-350 (2001).

List et al., Hydrogenation of Soybean Oil Triglycerides: Effect of Pressure on Selectivity. JAOCS (2000), vol. 77, pp. 311-314.

Nickitas-Etienne, PCT International Preliminary Report on Patentability, PCT/GB2011/050189, pp. 11 (Aug. 7, 2012).

Nickitas-Etienne, PCT International Preliminary Report on Patentability, PCT/GB2011/052115, pp. 8 (Apr. 30, 2013).

Schule, PCT International Search Report & Written Opinion, PCTGB2012050241, pp. 24 (Jul. 13, 2012).

Schule, PCT International Search Report & Written Opinion, PCTGB2012050242, pp. 12 (Jan. 22, 2013).

Strickley, Solubilizing Excipients in Oral and Inkectable Formulations Pharaceutical (2004), vol. 21, pp. 21, pp. 201-230.

Wolfgang Grebe, et al., A Multicenter, Randomized, Double-Blind, Double-Dummy, Placebo- and Active-Controlled, Parallel-Group Comparison of Diclofenac-K and Ibuprofen for the Treatment of Adults with Influenza-like Symptoms, Clinical Therapeutics 25(2): 444-459 (2003).

Vane JR et al., Mechanism of action of anti-inflammatory drugs, Int J Tissue React. 1998;20(1):3-15, abstract.

International Preliminary Report on Patentability and Written Opinion PCT/EP2014/050627, Date of Issuance Aug. 4, 2015.

Sharma, et al., "Preparation and Characterization of Meloxicam—Myrj-52 Granules Obtained by Melt Granulation," PharmaTech, (2007).

* cited by examiner

COMPOSITIONS AND METHODS FOR TREATING SEVERE PAIN

This application is a continuation that claims priority pursuant to 35 U.S.C. §120 to U.S. patent application Ser. No. 14/155,080, filed Jan. 14, 2014, which is a continuation-in-part application that claims priority pursuant to 35 U.S.C. §120 to U.S. patent application Ser. No. 13/365,824, filed Feb. 3, 2012, a continuation-in-part application that claims priority to patent application PCT/GB2011/052115, filed Oct. 31, 2011, an international patent application that claims priority to GB 1018289.7, filed Oct. 29, 2010, and claims priority to U.S. patent application Ser. No. 13/365,828, filed Feb. 3, 2012, and claims priority to GB 1113730.4, filed Aug. 10, 2011, GB 1113729.6, filed Aug. 10, 2011, GB 1113728.8, filed Aug. 10, 2011, and GB 1101937.9, filed Feb. 4, 2011, and this continuation-in-part application claims priority pursuant to 35 U.S.C. §119(e) to U.S. Provisional Patent Application 61/752,309, filed Jan. 14, 2013, and U.S. Provisional Patent Application 61/752,356, filed Jan. 14, 2013, each of which is hereby incorporated by reference in its entirety.

Pain is a subjective and very complex perception that signals to an individual that tissue damage has occurred or may be occurring. Pain may be transitory, lasting only until the noxious stimulus causing the pain is removed or the underling damage or pathology has healed or may lasts beyond the healing of an injury, continuing for a period of several months or longer. A pain response has both physiological as well as psychological components. A pain response evokes a wide range of sensations that may be described as a dull, aching sensation, a sharp stabbing sensation, a hot, cold, or icy-hot sensation, a tingling or itchy sensation or a numbness. Pain can be felt in one area of the body, such as your back, abdomen or chest or throughout the body, such as when all the muscles in a body ache from the flu.

Severe pain is the most common reason for an individual to consult a healthcare provider in the United States. It is a major symptom in many medical conditions, and can significantly interfere with a person's quality of life and general functioning. As such, severe pain is a significant and costly healthcare problem.

Current therapies for treating severe pain are limited, often involving the administration of multiple medications with the understanding that pain relief will not be complete and the quality of life may not be restored. These therapies may require frequent dosing, can be associated with undesirable systemic side effects, and typically provide unsatisfactory relief. Therefore, there remains a need for a therapeutic option developed specifically for severe pain that provides sustained relief while minimizing the potential for systemic side effects and drug-drug interactions.

The present specification discloses pharmaceutical compositions and methods for treating an individual suffering from a severe pain condition. The pharmaceutical compositions disclosed herein are essentially a lipid delivery system that enables a therapeutic compound having anti-pain activity to be delivered in a manner that more effectively inhibits a pain response. The end result is an improved treatment for a severe pain condition.

SUMMARY

Aspects of the present specification disclose a pharmaceutical composition comprising a therapeutic compound and a pharmaceutically-acceptable adjuvant. A therapeutic compound may have an anti-pain activity. Other aspects of the present specification disclose a pharmaceutical composition comprising a therapeutic compound disclosed herein, a pharmaceutically-acceptable solvent, and a pharmaceutically-acceptable adjuvant. In other aspects, the pharmaceutical compositions disclosed herein further comprise a pharmaceutically-acceptable stabilizing agent.

Other aspects of the present specification disclose a method of preparing a pharmaceutical composition, the method comprising the step of contacting a therapeutic compound with a pharmaceutically-acceptable adjuvant under conditions which allow the formation of the pharmaceutical composition. Other aspects of the present specification disclose a method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has an anti-pain activity, and b) contacting the solution formed in step (a) with a pharmaceutically-acceptable adjuvant under conditions which allow the formation of the pharmaceutical composition. In other aspects, the method of preparing disclosed herein further comprises c) removing the pharmaceutically-acceptable solvent from the pharmaceutical composition.

Other aspects of the present specification disclose a pharmaceutical composition, the pharmaceutical composition made according to a method comprising the step of contacting a therapeutic compound with a pharmaceutically-acceptable adjuvant under conditions which allow the formation of the pharmaceutical composition. Other aspects of the present specification disclose a pharmaceutical composition, the pharmaceutical composition made according to a method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has an anti-pain activity, and b) contacting the solution formed in step (a) with a pharmaceutically-acceptable adjuvant under conditions which allow the formation of the pharmaceutical composition. In other aspects, the method of making a pharmaceutical composition disclosed herein further comprises c) removing the pharmaceutically-acceptable solvent from the pharmaceutical composition.

Other aspects of the present specification disclose a method of treating an individual with a severe pain condition, the method comprising the step of administering to the individual in need thereof a pharmaceutical composition disclosed herein, wherein administration results in a reduction in a symptom associated with the severe pain condition, thereby treating the individual.

Other aspects of the present specification disclose a use of a pharmaceutical composition disclosed herein in the manufacture of a medicament for the treatment of a severe pain condition.

Other aspects of the present specification disclose a use of a pharmaceutical composition disclosed herein for the treatment of a severe pain condition.

DESCRIPTION

Aspects of the present specification disclose, in part, a composition. A composition disclosed herein is generally administered as a pharmaceutical acceptable composition. As used herein, the term "pharmaceutically acceptable"

refers any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with a therapeutic compound or permitted to dilute or enclose the active compound and can be a solid, semi-solid, or liquid agent. It is understood that a therapeutic compound or other active ingredient can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In one embodiment, a pharmaceutical composition disclosed herein comprises a therapeutic compound having an anti-pain activity and a pharmaceutically-acceptable adjuvant. An anti-pain activity encompasses a deadening or absence of the sense of pain or nociception without loss of consciousness and includes, without limitation, an analgesic activity, and/or a nociceptive activity. In another embodiment, a pharmaceutical composition disclosed herein comprises a therapeutic compound having an anti-pain activity, a pharmaceutically-acceptable solvent, and a pharmaceutically-acceptable adjuvant. In aspects of this embodiment, a pharmaceutical composition disclosed herein may further comprise a pharmaceutically-acceptable stabilizing agent. In other aspects of this embodiment, a pharmaceutical composition disclosed herein may further comprise a pharmaceutically-acceptable carrier, a pharmaceutically-acceptable component, or both pharmaceutically-acceptable carrier and pharmaceutically-acceptable component.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may have an anti-pain activity.

In an embodiment, a therapeutic compound disclosed herein has an anti-pain activity capable of reducing a severe pain response. In aspects of this embodiment, a therapeutic compound disclosed herein has an anti-pain activity capable of reducing a severe pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a severe pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a nociceptive pain response. In aspects of this embodiment, a therapeutic compound disclosed herein has an anti-pain activity capable of reducing a nociceptive pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a nociceptive pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a pain response mediated by a nociceptive receptor. In aspects of this embodiment, a therapeutic compound disclosed herein has an anti-pain activity capable of reducing a pain response mediated by a nociceptive receptor by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a pain response mediated by a nociceptive receptor in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a somatic pain response. In aspects of this embodiment, a therapeutic compound disclosed herein has an anti-pain activity capable of reducing a somatic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a somatic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a visceral pain response. In aspects of this embodiment, a therapeutic compound disclosed herein has an anti-pain activity capable of reducing a visceral pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a visceral pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a pathological pain response. In aspects of this embodiment, a therapeutic compound disclosed herein has an anti-pain activity capable of reducing a pathological pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a pathological pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a neuropathic pain response. In aspects of this embodiment, a therapeutic compound disclosed herein has an anti-pain activity capable of reducing a neuropathic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a neuropathic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a central neuropathic pain response. In aspects of this embodiment, a therapeutic compound disclosed herein has an anti-pain activity capable of reducing a central neuropathic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a central neuropathic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a peripheral neuropathic pain response. In aspects of this embodiment, a therapeutic compound disclosed herein has an anti-pain activity capable of reducing a peripheral neuropathic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a peripheral neuropathic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a mononeuropathic pain response. In aspects of this embodiment, a therapeutic compound disclosed herein has an anti-pain activity capable of reducing a mononeuropathic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a mononeuropathic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a mononeuropathic multiplex pain response. In aspects of this embodiment, a therapeutic compound disclosed herein has an anti-pain activity capable of reducing a mononeuropathic multiplex pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a mononeuropathic multiplex pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a polyneuropathic pain response. In aspects of this embodiment, a therapeutic compound disclosed herein has an anti-pain activity capable of reducing a polyneuropathic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a polyneuropathic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing an autonomic neuropathic pain response. In aspects of this embodiment, a therapeutic compound disclosed herein has an anti-pain activity capable of reducing an autonomic neuropathic pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing an autonomic neuropathic pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a neuralgia pain response. In aspects of this embodiment, a therapeutic compound disclosed herein has an anti-pain activity capable of reducing a neuralgia pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a neuralgia pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a complex regional pain syndrome pain response. In aspects of this embodiment, a therapeutic compound disclosed herein has an anti-pain activity capable of reducing a complex regional pain syndrome pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a complex regional pain syndrome pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a referred pain response. In aspects of this embodiment, a therapeutic compound disclosed herein has an anti-pain activity capable of reducing a referred pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a referred pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a deafferentation pain response. In aspects of this embodiment, a therapeutic compound disclosed herein has an anti-pain activity capable of reducing a deafferentation pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a deafferentation pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a dysfunctional pain response. In aspects of this embodiment, a therapeutic compound disclosed herein has an anti-pain activity capable of reducing a dysfunctional pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a dysfunctional pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a headache pain response. In aspects of this embodiment, a therapeutic compound disclosed herein has an anti-pain activity capable of reducing a headache pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a headache pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a therapeutic compound disclosed herein has an anti-pain activity capable of reducing a migraine pain response. In aspects of this embodiment, a therapeutic compound disclosed herein has an anti-pain activity capable of reducing a migraine pain response by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic compound disclosed herein has an anti-pain activity capable of reducing a migraine pain response in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound disclosed herein may have a log P value indicating that the compound is soluble in an organic solvent. As used herein, the term "log P value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In aspects of this embodiment, a therapeutic compound disclosed herein may have a log P value indicating that the compound is substantially soluble in an organic solvent. In aspects of this embodiment, a therapeutic compound disclosed herein may have a log P value indicating that the compound is, e.g., at least 50% soluble in an organic solvent, at least 60% soluble in an organic solvent, at least 70% soluble in an organic solvent, at least 80% soluble in an organic solvent, or at least 90% soluble in an organic solvent. In aspects of this embodiment, a therapeutic compound disclosed herein may have a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.

In aspects of this embodiment, a therapeutic compound disclosed herein may have a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6. In other aspects of this embodiment, a therapeutic compound disclosed herein may have a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0. In other aspects of this embodiment, a therapeutic compound disclosed herein may have a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0. In still other aspects of this embodiment, a therapeutic compound disclosed herein may have a log P value in the range of, e.g., between 2.0 and 2.5, between 2.0 and 2.7, between 2.0 and 3.0, or between 2.2 and 2.5.

A therapeutic compound disclosed herein may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In aspects of this embodiment, a therapeutic compound disclosed herein may have a polar surface area of, e.g., less than 8.0 nm$^2$, less than 7.0 nm$^2$, less than 6.0 nm$^2$, less than 5.0 nm$^2$, less than 4.0 nm$^2$, or less than 3.0 nm$^2$. In other aspects of this embodiment, a therapeutic compound disclosed herein may have a polar surface area in the range of, e.g., between 3.0 nm$^2$ and 6.5 nm$^2$, between 3.0 nm$^2$ and 6.0 nm$^2$, between 3.0 nm$^2$ and 5.5 nm$^2$, between 3.0 nm$^2$ and 5.0 nm$^2$, between 3.0 nm$^2$ and 4.5 nm$^2$, between 3.5 nm$^2$ and 6.5 nm$^2$, between 3.5 nm$^2$ and 6.0 nm$^2$, between 3.5 nm$^2$ and 5.5 nm$^2$, between 3.5 nm$^2$ and 5.0 nm$^2$, between 3.5 nm$^2$ and 4.5 nm$^2$, between 4.0 nm$^2$ and 6.5 nm$^2$, between 4.0 nm$^2$ and 6.0 nm$^2$, between 4.0 nm$^2$ and 5.5 nm$^2$, or between 4.0 nm$^2$ and 5.0 nm$^2$, between 4.0 nm$^2$ and 4.5 nm$^2$, or between 4.5 nm$^2$ and 5.5 nm$^2$. In yet other aspects of this embodiment, a therapeutic compound disclosed herein may have a polar surface area in the range of, e.g., between 2.0 nm$^2$ and 6.5 nm$^2$, between 2.0 nm$^2$ and 6.0 nm$^2$, between 2.0 nm$^2$ and 5.5 nm$^2$, between 2.0 nm$^2$ and 5.0 nm$^2$, between 2.0 nm$^2$ and 4.5 nm$^2$, between 2.5 nm$^2$ and 6.5 nm$^2$, between 2.5 nm$^2$ and 6.0 nm$^2$, between 2.5 nm$^2$ and 5.5 nm$^2$, between 2.5 nm$^2$ and 5.0 nm$^2$, or between 2.5 nm$^2$ and 4.5 nm$^2$.

A therapeutic compound disclosed herein may be a non-steroidal anti-inflammatory drug (NSAID). NSAIDs are a large group of therapeutic compounds with analgesic, anti-pain, and anti-pyretic properties. NSAIDs include, without limitation, Aceclofenac, Acemetacin, Actarit, Alcofenac, Alminoprofen, Amfenac, Aloxipirin, Aminophenazone, Antraphenine, Aspirin, Azapropazone, Benorilate, Benoxaprofen, Benzydamine, Butibufen, Celecoxib, Chlorthenoxacin, Choline Salicylate, Clometacin, Dexketoprofen, Diclofenac, Diflunisal, Emorfazone, Epirizole; Etodolac, Etoricoxib, Feclobuzone, Felbinac, Fenbufen, Fenclofenac, Flurbiprofen, Glafenine, Hydroxylethyl salicylate, Ibuprofen, Indometacin, Indoprofen, Ketoprofen, Ketorolac, Lactyl phenetidin, Loxoprofen, Lumiracoxib, Mefenamic acid, Meloxicam, Metamizole, Metiazinic acid, Mofebutazone, Mofezolac, Nabumetone, Naproxen, Nifenazone, Niflumic acid, Oxametacin, Phenacetin, Pipebuzone, Pranoprofen, Propyphenazone, Proquazone, Protizinic acid, Rofecoxib, Salicylamide, Salsalate, Sulindac, Suprofen, Tiaramide, Tinoridine, Tolfenamic acid, Valdecoxib, and Zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, and a selective cyclooxygenase 2 (COX 2) inhibitor. A NSAID may be a profen. Examples of a suitable salicylate derivative NSAID include, without limitation, Acetylsalicylic acid (asprin), Diflunisal, and Salsalate. Examples of a suitable p-amino phenol derivative NSAID include, without limitation, Paracetamol and Phenacetin. Examples of a suitable propionic acid derivative NSAID include, without limitation, Alminoprofen, Benoxaprofen, Dexketoprofen, Fenoprofen, Flurbiprofen, Ibuprofen, Indoprofen, Ketoprofen, Loxoprofen, Naproxen, Oxaprozin, Pranoprofen, and Suprofen. Examples of a suitable acetic acid derivative NSAID include, without limitation, Aceclofenac, Acemetacin, Actarit, Alcofenac, Amfenac, Clometacin, Diclofenac, Etodolac, Felbinac, Fenclofenac, Indometacin, Ketorolac, Metiazinic acid, Mofezolac, Nabumetone, Naproxen, Oxametacin, Sulindac, and Zomepirac. Examples of a suitable enolic acid (Oxicam) derivative NSAID include, without limitation, Droxicam, Isoxicam, Lornoxicam, Meloxicam, Piroxicam, and Tenoxicam. Examples of a suitable fenamic acid derivative NSAID include, without limitation, Flufenamic acid, Mefenamic acid, Meclofenamic acid, and Tolfenamic acid. Examples of a suitable selective COX-2 inhibitors include, without limitation, Celecoxib, Etoricoxib, Firocoxib, Lumiracoxib, Meloxicam, Parecoxib, Rofecoxib, and Valdecoxib.

A therapeutic compound disclosed herein may be a PPARγ agonist. Examples of a suitable PPARγ agonist include, without limitation, Benzbromarone, a cannabidiol, Cilostazol, Curcumin, Delta(9)-tetrahydrocannabinol, glycyrrhetinic acid, Indomethacin, Irbesartan, Monascin, mycophenolic acid, Resveratrol, 6-shogaol, Telmisartan, a thiazolidinedione like Rosiglitazone, Pioglitazone, and Troglitazone, a NSAID, and a fibrate. Other suitable PPARγ agonists are described in Masson and Caumont-Bertrand, PPAR Agonist Compounds, Preparation and Uses, US 2011/0195993, which is hereby incorporated by reference in its entirety.

A therapeutic compound disclosed herein may be a nuclear receptor binding agent. Examples of a suitable nuclear receptor binding agent include, without limitation, a Retinoic Acid Receptor (RAR) binding agent, a Retinoid X Receptor (RXR) binding agent, a Liver X Receptor (LXR) binding agent and a Vitamin D binding agent.

A therapeutic compound disclosed herein may be an anti-hyperlipidemic agent. There are several classes of anti-hyperlipidemic agents (also known as hypolipidemic agents). They may differ in both their impact on the cholesterol profile and adverse effects. For example, some may lower low density lipoprotein (LDL), while others may preferentially increase high density lipoprotein (HDL). Clinically, the choice of an agent will depend on the cholesterol profile of an individual, cardiovascular risk of an individual, and/or the liver and kidney functions of an individual. Examples of a suitable anti-hyperlipidemic agent include, without limitation, a fibrate, a statin, a tocotrienol, a niacin, a bile acid sequestrants (resin), a cholesterol absorption inhibitor, a pancreatic lipase inhibitor, and a sympathomimetic amine.

A therapeutic compound disclosed herein may be a fibrate. Fibrates are a class of amphipathic carboxylic acids with lipid level modifying properties. These therapeutic compounds are used for a range of metabolic disorders. One non-limiting use is as an anti-hyperlipidemic agent where it may lower levels of, e.g., triglycerides and LDL as well as increase levels of HDL. Examples of a suitable fibrate include, without limitation, Bezafibrate, Ciprofibrate, Clofibrate, Gemfibrozil, and Fenofibrate.

A therapeutic compound disclosed herein may be a statin. Statins (or HMG-CoA reductase inhibitors) are a class of therapeutic compounds used to lower LDL and/or cholesterol levels by inhibiting the enzyme HMG-CoA reductase, which plays a central role in the production of cholesterol in the liver. To compensate for the decreased cholesterol availability, synthesis of hepatic LDL receptors is increased, resulting in an increased clearance of LDL particles from the blood. Examples of a suitable statin include, without limitation, Atorvastatin, Fluvastatin, Lovastatin, Pitavastatin, Pravastatin, Rosuvastatin, and Simvastatin.

A therapeutic compound disclosed herein may be a tocotrienol. Tocotrienols are anotehr class of HMG-CoA reductase inhibitors and may be used to lower LDL and/or cholesterol levels by inducing hepatic LDL receptor up-regulation and/or decreasing plasma LDL levels. Examples of a suitable tocotrienol include, without limitation, a γ-tocotrienol and a δ-tocotrienol.

A therapeutic compound disclosed herein may be a niacin. Niacins are a class of therapeutic compounds with lipid level modifying properties. For example, a niacin may lower LDL by selectively inhibiting hepatic diacyglycerol acyltransferase 2, reduce triglyceride synthesis, and VLDL secretion through a receptor HM74 and HM74A or GPR109A. These therapeutic compounds are used for a range of metabolic disorders. One non-limiting use is as an anti-hyperlipidemic agent where it may inhibit the breakdown of fats in adipose tissue. Because a niacin blocks the breakdown of fats, it causes a decrease in free fatty acids in the blood and, as a consequence, decreases the secretion of very-low-density lipoproteins (VLDL) and cholesterol by the liver. By lowering VLDL levels, a niacin may also increase the level of HDL in blood. Examples of a suitable niacin include, without limitation, acipimox, niacin, nicotinamide, and vitamin B3.

A therapeutic compound disclosed herein may be a bile acid sequestrant. Bile acid sequestrants (also known as resins) are a class of therapeutic compounds used to bind certain components of bile in the gastrointestinal tract. They disrupt the enterohepatic circulation of bile acids by sequestering them and preventing their reabsorption from the gut. Bile acid sequestrants are particularly effective for lowering LDL and cholesterol by sequestering the cholesterol-containing bile acids released into the intestine and preventing their reabsorption from the intestine. In addition, a bile acid sequestrant may also raise HDL levels. Examples of a suitable bile acid sequestrant include, without limitation, Cholestyramine, Colesevelam, and Colestipol.

A therapeutic compound disclosed herein may be a cholesterol absorption inhibitor. Cholesterol absorption inhibitors are a class of therapeutic compounds that inhibits the absorption of cholesterol from the intestine. Decreased cholesterol absorption leads to an upregulation of LDL-receptors on the surface of cells and an increased LDL-cholesterol uptake into these cells, thus decreasing levels of LDL in the blood plasma. Examples of a suitable cholesterol absorption inhibitor include, without limitation, Ezetimibe, a phytosterol, a sterol and a stanol.

A therapeutic compound disclosed herein may be a fat absorption inhibitor. Fat absorption inhibitors are a class of therapeutic compounds that inhibits the absorption of fat from the intestine. Decreased fat absorption reduces caloric intake. In one aspect, a fat absorption inhibitor inhibits pancreatic lipase, an enzyme that breaks down triglycerides in the intestine. Examples of a suitable fat absorption inhibitor include, without limitation, Orlistat.

A therapeutic compound disclosed herein may be a sympathomimetic amine. Sympathomimetic amines are a class of therapeutic compounds that mimic the effects of transmitter substances of the sympathetic nervous system such as catecholamines, epinephrine (adrenaline), norepinephrine (noradrenaline), and/or dopamine. A sympathomimetic amine may act as an α-adrenergic agonist, a β-adrenergic agonist, a dopaminergic agonist, a monoamine oxidase (MAO) inhibitor, and a COMT inhibitor. Such therapeutic compounds, among other things, are used to treat cardiac arrest, low blood pressure, or even delay premature labor. Examples of a suitable sympathomimetic amine include, without limitation, Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, and propylhexedrine.

A therapeutic compound disclosed herein may be an ester of a therapeutic compound. An ester of a therapeutic compound increases the log P value relative to the same therapeutic compound, but without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively inhibits a pro-inflammatory response as long as the compound is combined with an adjuvant disclosed herein. In one embodiment, a therapeutic compound may be reacted with ethyl ester in order to form an ethyl ester of the therapeutic compound.

In another embodiment, a pharmaceutical composition disclosed herein does not comprise a pharmaceutically-acceptable solvent disclosed herein. In an aspect of this embodiment, a pharmaceutical composition comprises a therapeutic compound and a pharmaceutically-acceptable adjuvant, but does not comprise a pharmaceutically-acceptable solvent disclosed herein.

A pharmaceutical composition disclosed herein may comprise a therapeutic compound in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

Aspects of the present specification disclose, in part, a pharmaceutically-acceptable solvent. A solvent is a liquid, solid, or gas that dissolves another solid, liquid, or gaseous (the solute), resulting in a solution. Solvents useful in the pharmaceutical compositions disclosed herein include, without limitation, a pharmaceutically-acceptable polar aprotic solvent, a pharmaceutically-acceptable polar protic solvent and a pharmaceutically-acceptable non-polar solvent. A pharmaceutically-acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically -acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically-acceptable non-polar solvent includes, without limitation, pentane, cyclopentane, hexane, cyclohexane, benzene, toluene, 1,4-Dioxane, chloroform, n-methyl- pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30')/0 (v/v), about 8% (v/v) to 20% (v/v), about 8% (v/v) to 15')/0 (v/v), or about 8% (v/v) to 12% (v/v).

In one embodiment, a solvent may comprise a pharmaceutically-acceptable alcohol. As used herein, the term "alcohol" refers to an organic molecule comprising a hydroxyl functional group (—OH) bond to a carbon atom, where the carbon atom is saturated. In aspects of this embodiment, the alcohol may be, e.g., a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-l, and prop-2-in-1-ol. Examples of an alicyclic alcohol include, without limitation, cyclohexane-1,2,3,4,5,6-hexol and 2-(2-propyl)-5-methyl-cyclohexane-1-ol.

In another embodiment, a solvent may comprise an ester of pharmaceutically-acceptable alcohol and an acid. Suitable pharmaceutically-acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically-acceptable glycol ether. Glycol ethers are a group of solvents based on alkyl ethers of ethylene glycol. Non-limiting examples include diethylene glycol monomethyl ether (2-(2-methoxyethoxy)ethanol), diethylene glycol monoethyl ether (2-(2-ethoxyethoxy)ethanol), diethylene glycol monopropyl ether (2-(2-propoxyethoxy)ethanol), diethylene glycol monoisopropyl ether (2-(2-isopropoxyethoxy)ethanol), and diethylene glycol mono-n-butyl ether (2-(2-butoxyethoxy)ethanol). Diethylene glycol monoethyl ether (2-(2-ethoxyethoxy)ethanol) is commercially available as TRANSCUTOL®.

In another embodiment, a solvent may comprise a pharmaceutically-acceptable diol. A diol or double alcohol is a chemical compound containing two hydroxyl groups (—OH groups).

In another embodiment, a solvent may comprise a pharmaceutically-acceptable propylene glycol. Propylene glycol, also called 1,2-propanediol or propane-1,2-diol, is an organic compound with formula $C_3H_8O_2$ or HO—$CH_2$—CHOH—$CH_3$.

In another embodiment, a solvent may comprise a pharmaceutically-acceptable dipropylene glycol. Dipropylene glycol is a mixture of three isomeric chemical compounds, 4-oxa-2,6-heptandiol, 2-(2-Hydroxy-propoxy)-propan-1-ol, and 2-(2-Hydroxy-1-methyl-ethoxy)-propan-1-ol.

In another embodiment, a solvent may comprise a pharmaceutically-acceptable polypropylene glycol (PPG) polymer. PPG polymers polymersg, also known as polypropylene oxide (PPO) polymers or polyoxypropylene (POP) polymers, are prepared by polymerization of propylene oxide and are commercially available over a wide range of molecular weights from 100 g/mol to 10,000,000 g/mol. PPG polymers with a low molecular mass are liquids or low-melting solids, whereas PPG polymers of a higher molecular mass are solids. A PPG polymer include, without limitation, PPG 100, PPG 200, PPG 300, PPG 400, PPG 500, PPG 600, PPG 700, PPG 800, PPG 900, PPG 1000, PPG 1100, PPG 1200, PPG 1300, PPG 1400, PPG 1500, PPG 1600, PPG 1700, PPG 1800, PPG 1900, PPG 2000, PPG 2100, PPG 2200, PPG 2300, PPG 2400, PPG 2500, PPG 2600, PPG 2700, PPG 2800, PPG 2900, PPG 3000, PPG 3250, PPG 3350, PPG 3500, PPG 3750, PPG 4000, PPG 4250, PPG 4500, PPG 4750, PPG 5000, PPG 5500, PPG 6000, PPG 6500, PPG 7000, PPG 7500, PPG 8000, PPG 8500, PPG 9000, PPG 9500, PPG 10,000, PPG 11,000, PPG 12,000, PPG 13,000, PPG 14,000, PPG 15,000, PPG 16,000, PPG 17,000, PPG 18,000, PPG 19,000, or PPG 20,000.

In another embodiment, a solvent may comprise a pharmaceutically-acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically-acceptable glyceride. Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically-acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically-acceptable solid solvent includes, without limitation, menthol and PEG polymers above about 20,000 g/mol.

Aspects of the present specification disclose, in part, a pharmaceutically-acceptable adjuvant. An adjuvant is a pharmacological agent that modifies the effect of other agents, such as, e.g., a therapeutic compound disclosed herein. In addition, an adjuvant disclosed herein may be used as a solvent that dissolves a therapeutic compound disclosed herein, forming a adjuvant solution. An adjuvant disclosed herein facilitates delivery of a therapeutic compound in a manner that more effectively inhibits a pro-inflammatory response. In one embodiment, an adjuvant disclosed herein facilitates the delivery of a therapeutic compound disclosed herein into macrophages.

A pharmaceutical composition disclosed herein may comprise a pharmaceutically-acceptable adjuvant in an amount sufficient to mix with a solution disclosed herein or an emulsion disclosed herein. In other aspects of this embodiment, a pharmaceutical composition disclosed herein may comprise an adjuvant in an amount of, e.g., at least 10% (v/v), at least 20% (v/v), at least 30% (v/v), at least 35% (v/v), at least 40% (v/v), at least 45% (v/v), at least 50% (v/v), at least 55% (v/v), at least 60% (v/v), at least 65% (v/v), at least 70% (v/v), at least 75% (v/v), at least 80% (v/v), at least 85% (v/v), at least 90% (v/v), at least 95% (v/v), or at least 99% (v/v). In other aspects of this embodiment, a pharmaceutical composition disclosed herein may comprise an adjuvant in an amount in a range of, e.g., about 30% (v/v) to about 99% (v/v), about 35% (v/v) to about 99% (v/v), about 40% (v/v) to about 99% (v/v), about 45% (v/v) to about 99% (v/v), about 50% (v/v) to about 99% (v/v), about 30% (v/v) to about 98% (v/v), about 35% (v/v) to about 98% (v/v), about 40% (v/v) to about 98% (v/v), about 45% (v/v) to about 98% (v/v), about 50% (v/v) to about 98% (v/v), about 30% (v/v) to about 95% (v/v), about 35% (v/v) to about 95% (v/v), about 40% (v/v) to about 95% (v/v), about 45% (v/v) to about 95% (v/v), or about 50% (v/v) to about 95% (v/v). In yet other aspects of this embodiment, a pharmaceutical composition disclosed herein may comprise an adjuvant in an amount in a range of, e.g., about 70% (v/v) to about 97% (v/v), about 75% (v/v) to about 97% (v/v), about 80% (v/v) to about 97% (v/v), about 85% (v/v) to about 97% (v/v), about 88% (v/v) to about 97% (v/v), about 89% (v/v) to about 97% (v/v), about 90% (v/v) to about 97% (v/v), about 75% (v/v) to about 96% (v/v), about 80% (v/v) to about 96% (v/v), about 85% (v/v) to about 96% (v/v), about 88% (v/v) to about 96% (v/v), about 89% (v/v) to about 96% (v/v), about 90% (v/v) to about 96% (v/v), about 75% (v/v) to about 93% (v/v), about 80% (v/v) to about 93% (v/v), about 85% (v/v) to about 93% (v/v), about 88% (v/v) to about 93% (v/v), about 89% (v/v) to about 93% (v/v), or about 90% (v/v) to about 93% (v/v).

In one embodiment, an adjuvant may be a pharmaceutically-acceptable lipid. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids (like monoglycerides, diglycerides, and triglycerides), phospholipids, sphingolipids, sterol lipids, prenol lipids, saccharolipids, and polyketides. A pharmaceutical composition disclosed herein may comprise a lipid such as, e.g. an oil, an oil-based liquid, a fat, a fatty acid, a wax, a fatty acid ester, a fatty acid salt, a fatty alcohol, a glyceride (mono-, di- or triglyceride), a partially hydrolyzed glycerolipid, a phospholipids, a glycol ester, a sucrose ester, a glycerol oleate derivative, a medium chain triglyceride, or a mixture thereof. Other examples of pharmaceutically-acceptable lipids useful as adjuvants are described in, e.g., U.S. Pat. No. 6,923,988, U.S. Pat. No. 6,451,339, U.S. Pat. No. 6,383,471, U.S. Pat. No. 6,294,192, and U.S. Pat. No. 6,267,985, each of which is hereby incorporated by reference in its entirety.

A lipid useful in the pharmaceutical compositions disclosed herein may be a pharmaceutically-acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, Capryllic acid (8:0), pelargonic acid (9:0), Capric acid (10:0), Undecylic acid (11:0), Lauric acid (12:0), Tridecylic acid (13:0), Myristic acid (14:0), Myristoleic acid (14:1), Pentadecyclic acid (15:0), Palmitic acid (16:0), Palmitoleic acid (16:1), Sapienic acid (16:1), Margaric acid (17:0), Stearic acid (18:0), Oleic acid (18:1), Elaidic acid (18:1), Vaccenic acid (18:1), Linoleic acid (18:2), Linoelaidic acid (18:2), α-Linolenic acid (18:3), γ-Linolenic acid (18:3), Stearidonic acid (18:4), Nonadecylic acid (19:0), Arachidic acid (20:0), Eicosenoic acid (20:1), Dihomo-γ-linolenic acid (20:3), Mead acid (20:3), Arachidonic acid (20:4), Eicosapentaenoic acid (20:5), Heneicosylic acid (21:0), Behenic acid (22:0), Erucic acid (22:1), Docosahexaenoic acid (22:6), Tricosylic acid (23:0), Lignoceric acid (24:0), Nervonic acid (24:1), Pentacosylic acid (25:0), Cerotic acid (26:0), Heptacosylic acid (27:0), Montanic acid (28:0), Nonacosylic acid (29:0), Melissic acid (30:0), Henatriacontylic acid (31:0), Lacceroic acid (32:0), Psyllic acid (33:0), Geddic acid (34:0), Ceroplastic acid (35:0), and Hexatriacontylic acid (36:0).

A lipid useful in the pharmaceutical compositions disclosed herein may be a pharmaceutically-acceptable partially hydrogenated lipid. The process of hydrogenation adds hydrogen atoms to unsaturated lipid, eliminating double bonds and making them into partially or completely saturated lipid. Partial hydrogenation is a chemical rather than enzymatic, that converts a part of cis-isomers into trans-unsaturated lipids instead of hydrogenating them completely. In the first reaction step, one hydrogen is added, with the other, coordinatively unsaturated, carbon being attached to the catalyst. The second step is the addition of hydrogen to the remaining carbon, producing a saturated fatty acid. The first step is reversible, such that the hydrogen is readsorbed on the catalyst and the double bond is re-formed. The intermediate with only one hydrogen added contains no double bond and can freely rotate. Thus, the double bond can re-form as either cis or trans, of which trans is favored, regardless the starting material.

In an embodiment, an adjuvant may be a pharmaceutically-acceptable saturated or unsaturated fatty acid. In aspects of this embodiment, a saturated or unsaturated fatty acid comprises, e.g., at least 8, at least 10, at least 12, at least 14, at least 16, at least 18, at least 20, at least 22, at least 24, at least 26, at least 28, or at least 30 carbon atoms, In other aspects of this embodiment, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

In aspects of this embodiment, a pharmaceutically-acceptable saturated or unsaturated fatty acid is liquid at room temperature. The melting point of a fatty acid is largely determined by the degree of saturation/unsaturation of the hydrocarbon chain. In aspects of this embodiment, a saturated or unsaturated fatty acid has a melting point temperature of, e.g., 20° C. or below, 15° C. or below, 10° C. or below, 5° C. or below, 0° C. or below, −5° C. or below, −10° C. or below, −15° C. or below, or −20° C. or below. In other aspects of this embodiment, a saturated or unsaturated fatty acid has a melting point temperature in the range of, e.g., about −20° C. to about 20° C., about −20° C. to about 18° C., about −20° C. to about 16° C., about −20° C. to about 12° C., about −20° C. to about 8° C., about −20° C. to about 4° C., about −20° C. to about 0° C., about −15° C. to about 20° C., about −15° C. to about 18° C., about −15° C. to about 16° C., about −15° C. to about 12° C., about −15° C. to about 8° C., about −15° C. to about 4° C., about −15° C. to about 0° C.

In another embodiment, an adjuvant may comprise one kind of pharmaceutically-acceptable fatty acid. In aspects of this embodiment, an adjuvant may comprise only palmitic acid, only stearic acid, only oleic acid, only linoleic acid, or only linolenic acid.

In another embodiment, an adjuvant may comprise a plurality of different pharmaceutically-acceptable fatty acids. In aspects of this embodiment, an adjuvant may comprise, e.g., two or more different fatty acids, three or more different fatty acids, four or more different fatty acids, five or more different fatty acids, or six or more different fatty acids.

In other aspects of this embodiment, an adjuvant may comprise two or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid and/or stearic acid and/or oleic acid:linolenic acid and/or linoleic acid of, e.g., at least 2:1, at least 3:1, at least 4:1, at least 5:1, at least 6:1, at least 7:1, at least 8:1, at least 9:1, at least 10:1, at least 15:1, or at least 20:1. In yet other aspects of this embodiment, an adjuvant may comprise a ratio of palmitic acid and/or stearic acid and/or oleic acid:linolenic acid and/or linoleic acid in a range of, e.g., about 1:1 to about 20:1, about 2:1 to about 15:1, about 4:1 to about 12:1, or about 6:1 to about 10:1.

In other aspects of this embodiment, an adjuvant may comprise four or more different pharmaceutically-acceptable fatty acids including at least palmitic acid, stearic acid, oleic acid, linoleic acid and/or linolenic acid, and any combination thereof. In other aspects of this embodiment, an adjuvant may comprise a ratio of palmitic acid;stearic acid: linolenic acid:linoleic acid of, e.g., 10:10:1:1, 9:9:1:1, 8:8: 1:1, 7:7:1:1, 6:6:1:1, 5:5:1:1, 4:4:1:1, 3:3:1:1, 2:2:1:1, or 1:1:1:1. In other aspects of this embodiment, an adjuvant may comprise a ratio of palmitic acid;stearic acid:linolenic acid:linoleic acid in a range of, e.g., about 10:10:1:1 to about 6:6:1:1, about 8:8:1:1 to about 4:4:1:1, or about 5:5:1:1 to about 1:1:1:1.

A lipid useful in the pharmaceutical compositions disclosed herein may be a pharmaceutically-acceptable omega fatty acid. Non-limiting examples of an omega fatty acid include omega-3, omega-6, omega-7, and omega-9. Omega-3 fatty acids (also known as n-3 fatty acids or ω-3 fatty acids) are a family of essential unsaturated fatty acids that have in common a final carbon-carbon double bond in the n-3 position, that is, the third bond, counting from the methyl end of the fatty acid. The omega-3 fatty acids are "essential" fatty acids because they are vital for normal metabolism and cannot be synthesized by the human body.

An omega-3 fatty acid includes, without limitation, Hexadecatrienoic acid (16:3), α-Linolenic acid (18:3), Stearidonic acid (18:4), Eicosatrienoic acid (20:3), Eicosatetraenoic acid (20:4), Eicosapentaenoic acid (20:5), Heneicosapentaenoic acid (21:5), Docosapentaenoic acid (Clupanodonic acid) (22:5), Docosahexaenoic acid (22:6), Tetracosapentaenoic acid (24:5), Tetracosahexaenoic acid (Nisinic acid) (24:6).

Omega-6 fatty acids (also known as n-6 fatty acids or ω-6 fatty acids) are a family of unsaturated fatty acids that have in common a final carbon-carbon double bond in the n-6 position, that is, the sixth bond, counting from the methyl end of the fatty acid. An omega-6 fatty acid includes, without limitation, Linoleic acid (18:2), γ-linolenic acid (18:3), Calendic acid (18:3), Eicosadienoic acid (20:2), Dihomo-γ-linolenic acid (20:3), Arachidonic acid (20:4), Docosadienoic acid (22:2), Adrenic acid (22:4), Docosapentaenoic acid (22:5), Tetracosatetraenoic acid (24:4), and Tetracosapentaenoic acid (24:5).

Omega-7 fatty acids (also known as n-7 fatty acids or ω-7 fatty acids) are a family of unsaturated fatty acids that have in common a final carbon-carbon double bond in the n-7 position, that is, the seventh bond, counting from the methyl end of the fatty acid. An omega-7 fatty acid includes, without limitation, 5-Dodecenoic acid (12:1), 7-Tetradecenoic acid (14:1), 9-Hexadecenoic acid (Palmitoleic acid) (16:1), 11-Decenoic acid (Vaccenic acid) (18:1), 9Z,11E conjugated Linoleic acid (Rumenic acid)(18:2), 13-Eicosenoic acid (Paullinic acid) (20:1), 15-Docosenoic acid (22:1), and 17-Tetracosenoic acid (24:1).

Omega-9 fatty acids (also known as n-9 fatty acids or w-9 fatty acids) are a family of unsaturated fatty acids that have in common a final carbon-carbon double bond in the n-9 position, that is, the ninth bond, counting from the methyl end of the fatty acid. An omega-9 fatty acid includes, without limitation, Oleic acid (18:1), Elaidic acid (18:1), Eicosenoic acid (20:1), Mead acid (20:3), Erucic acid (22:1), Nervonic acid (24:1), and Ricinoleic acid.

A lipid useful in the pharmaceutical compositions disclosed herein may be a pharmaceutically-acceptable fat. Also known as a hard fat or solid fat, a fat includes any fatty acid that is solid at normal room temperature, such as, e.g. about 20° C. Fats consist of a wide group of compounds that are generally soluble in organic solvents and generally insoluble in water. A fat suitable as a lipid useful in the pharmaceutical compositions disclosed herein, may be a triglyceride, a triester of glycerol or any of several fatty acids.

A lipid useful in the pharmaceutical compositions disclosed herein may be a pharmaceutically-acceptable oil. An oil, also known as a liquid fat, includes any fatty acid that is liquid at normal room temperature, such as, e.g. about 20° C. An oil suitable as a lipid useful in the pharmaceutical compositions disclosed herein, may be a natural oil, a vegetable oil or any substance that does not mix with water and has a greasy feel. Examples of suitable natural oils include, without limitation, mineral oil, triacetin, ethyl oleate, a hydrogenated natural oil, or a mixture thereof. Examples of suitable vegetable oils include, without limitation, almond oil, arachis oil, avocado oil, canola oil, castor oil, coconut oil, corn oil, cottonseed oil, grape seed oil, hazelnut oil, hemp oil, linseed oil (flax seed oil), olive oil, palm oil, peanut oil, rapeseed oil, rice bran oil, safflower oil, sesame oil, soybean oil, soya oil, sunflower oil, theobroma oil (cocoa butter), walnut oil, wheat germ oil, or a mixture thereof. Each of these oils is commercially available from a number of sources well recognized by those skilled in the art.

An oil is typically a mixture of various fatty acids. For example, Rapeseed oil, obtained from the seeds of Brassica napus, includes both omega-6 and omega-3 fatty acids in a ratio of about 2:1. As another example, linseed oil, obtained from the seeds of Linum usitatissimum, includes abut 7% palmitic acid, about 3.4-4.6% stearic acid, about 18.5-22.6% oleic acid, about 14.2-17% linoleic acid, and about 51.9-55.2% α-linolenic acid. As another example, theobroma oil, obtained from the seeds of Theobroma cacao, includes glycerides derived from palmitic acid, stearic acid, oleic acid, linoleic acid, and arichidic acid, with melting point of 34-38° C. In aspects of this embodiment, a pharmaceutical composition comprises an oil including at least two different fatty acids, at least three different fatty acids, at least four different fatty acids, at least five different fatty acids, or at least six different fatty acids.

A lipid useful in the pharmaceutical compositions disclosed herein may be a pharmaceutically-acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid disclosed herein to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides. One group of glycerolipids is the glycerides, where one, two, or all three hydroxyl groups of glycerol have sugar residues attached via a glycosidic linkage.

A lipid useful in the pharmaceutical compositions disclosed herein may be a pharmaceutically-acceptable partially hydrolyzed glycerolipid. In an aspect of this embodiment, a pharmaceutically-acceptable partially hydrolyzed glycerolipid is a triglyceride partially hydrolyzed into a mixture of mono-, di-, and triglycerides.

A lipid useful in the pharmaceutical compositions disclosed herein may be a pharmaceutically-acceptable glycol fatty acid ester. A pharmaceutically-acceptable glycol fatty acid ester can be a monoester of a glycol, a diester of a glycol, or a triester of a glycol. A glycol fatty acid ester include, without limitation, a ethylene glycol fatty acid ester, a diethylene glyol fatty acid ester, a propylene glycol fatty acid ester, and a dipropylene fatty acid ester. Non-limiting examples of glycol fatty acid esters include, e.g., ethelene glycol caprylate, ethelene glycol pelagonate, ethelene glycol caprate, ethelene glycol undecylate, ethelene glycol laurate, ethelene glycol tridecylate, ethelene glycol myristate, ethelene glycol myristolate, ethelene glycol pentadecylate, ethelene glyol palmitate, ethelene glycol palmitoleate, ethelene glycol sapienate, ethelene glycol margarate, ethelene glycol stearate, ethelene glycol palmitosterate, ethelene glycol oleate, ethelene glycol elaidate, ethelene glycol vaccinate, ethelene glycol linoleate, ethelene glycol linoelaidate, ethelene glycol α-linolenate, ethelene glycol γ-linolenate, ethelene glycol stearidonate, ethelene glycol capprylocaprate, ethelene glycol dicapprylocaprate, diethylene glycol caprylate, diethelene glycol petagonate, diethelene glycol caprate, diethelene glycol undecylate, diethelene glycol laurate, diethelene glycol tridecylate, diethelene glycol myristate, diethelene glycol myristolate, diethelene glycol pentadecyclate, diethelene glycol palmitate, diethelene glycol palmitoleate, diethelene glycol sapienate, diethelene glycol margarate, diethelene glycol stearate, diethelene glycol palmitostearate, diethelene glycol oleate, diethelene glycol elaidate, diethelene glycol vaccinate, diethelene glycol linoleate, diethelene glycol linoelaidate, diethelene glycol α-linolenate, diethelene glycol γ-linolenate, diethelene glycol stearidonate, diethelene glycol caprylocaprate, diethelene glycol dicappyrlocaprate, propylene glycol caprylate, propylene glycol pelagonate, propylene glycol caprate, propylene glycol undecylate, propylene glycol laurate, propylene glycol tridecylate, propylene glycol myristate, propylene glycol myristolate, propylene glycol pentadecyclate, propylene glycol palmitate, propylene glycol palmitoleate, propylene glycol sapienate, propylene glycol margarate, propylene glycol stearate, propylene glycol palmitostearate, propylene glycol oleate, propylene glycol elaidate, propylene glycol vaccinate, propylene glycol linoleate, propylene glycol linoelaidate, propylene glycol α-linolenate, propylene glycol γ-linolenate, propylene glycol stearidonate, propylene glycol capprylocaprate, propylene glycol dicapprylocaprate, dipropylene glycol caprylate, dipropylene glycol pelagonate, dipropylene glycol caprate, dipropylene glycol undecylate, dipropylene glycol laurate, dipropylene glycol tridecylate, dipropylene glycol myristate, dipropylene glycol myristolate, dipropylene glycol pentadecylate, dipropylene glycol palmitate, dipropylene glycol palmitoleate, dipropylene glycol sapienate, dipropylene glycol margarate, dipropylene glycol stearate, dipropylene glycol palmitostearate, dipropylene glycol oleate, dipropylene glycol elaidate, dipropylene glycol vaccinate, dipropylene glycol linoleate, dipropylene glycol linoelaidate, dipropylene glycol α-linolenate, dipropylene glycol γ-linolenate, dipropylene glycol stearidonate, dipropylene glycol capprylocaprate, diprpoylene glycol dicapprylocaprate, or any combination thereof.

A lipid useful in the pharmaceutical compositions disclosed herein may be a pharmaceutically-acceptable polyether fatty acid ester. A pharmaceutically-acceptable polyether fatty acid ester can be a mono-fatty acid ester of a polyether, a di-fatty acid ester of a polyether, or a tri-fatty acid ester of a polyether. A polyether fatty acid ester includes, without limitation, a PEG fatty acid ester, a PEG glyceryl fatty acid, a PEG fatty acid ester glyceride, a PPG fatty acid ester, a PPG glyceryl fatty acid, and a PPG fatty acid ester glyceride. A PEG or PPG may be a molecular mass of, e.g., 5-20,000. Non-limiting examples of polyether fatty acid esters include, e.g., a PEG caprylate, a PEG pelargonate, a PEG caprate, a PEG undecylate, a PEG laurate, a PEG tridecylate, a PEG myristate, a PEG myristolate, a PEG pentadecylate, a PEG palmitate, a PEG palmitoleate, a PEG sapienate, a PEG margarate, a PEG stearate, a PEG palmitostearate, PEG oleate, PEG elaidate, PEG vaccinate, PEG linoleate, PEG linoelaidate, PEG α-linolenate, PEG γ-linolenate, PEG stearidonate, PEG capprylocaprate, PEG dicapprylocaprate, a PEG glyceryl caprylate, a PEG glyceryl pelargonate, a PEG glyceryl caprate, a PEG glyceryl undecylate, a PEG glyceryl laurate, a PEG glyceryl tridecylate, a PEG glyceryl myristate, a PEG glyceryl myristolate, a PEG glyceryl pentadecyclate, a PEG glyceryl palmitate, a PEG glyceryl palmitoleate, a PEG glyceryl sapienate, a PEG glyceryl margarate, a PEG glyceryl stearate, a PEG glyceryl palmitostearate, PEG glyceryl oleate, PEG glyceryl elaidate, PEG glyceryl vaccinate, PEG glyceryl linoleate, PEG glyceryl linoelaidate, PEG glyceryl α-linolenate, PEG glyceryl γ-linolenate, PEG glyceryl stearidonate, PEG glyceryl capprylocaprate, PEG glyceryl dicapprylocaprate, a capryloyl PEG glyceride, a pelargonoyl PEG glyceride, a caproyl PEG glyceride, an undecyloyl PEG glyceride, a lauroyl PEG glyceride, a tridecyloyl PEG glyceride, a myristoyl PEG glyceride, a myristoloyl PEG glyceride, a pentadecycloyl PEG glyceride, a palmitoyl PEG glyceride, a palmitoleoyl PEG glyceride, a sapienoyl PEG glyceride, a margaroyl PEG glyceride, a stearoyl PEG glyceride, a palmitostearoyl PEG glyceride, an oleoyl PEG glyceride, an elaidoyl PEG glyceride, a vaccinoyl PEG glyceride, a linoleoyl PEG glyceride, a linoelaidoyl PEG glyceride, an α-linolenoyl PEG glyceride, a γ-linolenoyl PEG glyceride, a stearidonoyl PEG glyceride, a capprylocaproyl PEG glyceride, a dicapprylocaproyl PEG glyceride, a PPG caprylate, a PPG pelargonate, a PPG caprate, a PPG undecylate, a PPG laurate, a PPG tridecylate, a PPG myristate, a PPG myristolate, a PPG pentadecyclate, a PPG palmitate, a PPG palmitoleate, a PPG sapienate, a PPG margarate, a PPG stearate, a PPG palmitostearate, a PPG oleate, a PPG elaidate, a PPG vaccinate, a PPG linoleate, a PPG linoelaidate, a PPG α-linolenate, a PPG γ-linolenate, a PPG stearidonate, a PPG capprylocaprate, a PPG dicapprylocaprate, a PPG glyceryl caprylate, a PPG glyceryl pelargonate, a PPG glyceryl caprate, a PPG glyceryl undecylate, a PPG glyceryl laurate, a PPG glyceryl tridecylate, a PPG glyceryl myristate, a PPG glyceryl myristolate, a PPG glyceryl pentadecyclate, a PPG glyceryl palmitate, a PPG glyceryl palmitoleate, a PPG glyceryl sapienate, a PPG glyceryl margarate, a PPG glyceryl stearate, a PPG glyceryl palmitostearate, a PPG glyceryl oleate, a PPG glyceryl elaidate, a PPG glyceryl vaccinate, a PPG glyceryl linoleate, a PPG glyceryl linoelaidate, a PPG glyceryl α-linolenate, a PPG glyceryl γ-linolenate, a PPG glyceryl stearidonate, a PPG glyceryl capprylocaprate, a PPG glyceryl dicapprylocaprate, a capryloyl PPG glyceride, a pelargonoyl PPG glyceride, a caproyl PPG glyceride, an undecyloyl PPG glyceride, a lauroyl PPG glyceride, a tridecyloyl PPG glyceride, a myristoyl PPG glyceride, a myristoloyl PPG glyceride, a pentadecycloyl PPG glyceride, a palmitoyl PPG glyceride, a palmitoleoyl PPG glyceride, a sapienoyl PPG glyceride, a margaroyl PPG glyceride, a stearoyl PPG glyceride, a palmitostearoyl PPG glyceride, an oleoyl PPG glyceride, an elaidoyl PPG glyceride, a vaccinoyl PPG glyceride, a linoleoyl PPG glyceride, a linoelaidoyl PPG glyceride, an α-linolenoyl PPG glyceride, a γ-linolenoyl PPG glyceride, a stearidonoyl PPG glyceride, a capprylocaproyl PPG glyceride, a dicapprylocaproyl PPG glyceride, or any combination thereof.

Comercially available pharmaceutically-acceptable polyether fatty acid esters include, without limitation, caprylocaproyl macrogol-8 glycerides (LABRASOL®), propylene glycol monopalmitostearate (MONOSTEOL®), glyceryl dibehenate (COMPRITOL® 888), glycerol behenate (COMPRITOL® E ATO), behenoyl pollyoxyl-8 glycerides (COMPRITOL® HD5 ATO), triglycerol diisostearate (PLUROL® Diisostearique), PEG-8 beeswax (APIFIL®), lauroyl macrogol-32 glycerides (GELUCIRE 44/14), stearoyl macrogol-32 glycerides (GELUCIRE 50.13), propylene glycol dicaprylocaprate (LABRAFAC® PG), polyglycerol-3 dioleate (PLUROL® Oleique CC 497), propylene glycol monolaurate (type I) (LAUROGLYCOL® FCC), propylene glycol monolaurate (type II) (LAUROGLYCOL® 90), propylene glycol monocaprylate (type I) (CAPRYOL® PGMC), propylene glycol monocaprylate (type II) (CAPRYOL® 90), linoleoyl macrogol-6 glycerides (LABRAFIL® M2125CS), oleoyl macrogol-6 glycerides (LABRAFIL® M1944CS), lauroyl macrogol-6 glycerides (LABRAFIL® M2130CS), glycerol dipalmitostearate (Biogapress Vegetal BM297ATO), glycerol distearate (type I) (PRECIROL® ATO 5), and glycerol monolinoleate (MAISINE™ 35-1).

A lipid useful in the pharmaceutical compositions disclosed herein may be a mixture of pharmaceutically-acceptable lipids. Examples of mixtures of pharmaceutically-acceptable lipids include, without limitation, a mixture of one or more glycerolipids disclosed herein, a mixture of one or more glycol fatty acid esters disclosed herein, a mixture of more polyether fatty acid esters disclosed herein, a mixture of more glycerides disclosed herein.

In aspects of this embodiment, a mixture of pharmaceutically-acceptable lipids includes a mixture of mono-, di-, and/or triglycerides having a melting point of, e.g., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., about 50° C. In aspects of this embodiment, a mixture of pharmaceutically-acceptable lipids includes a mixture of mono-, di-, and/or triglycerides having a melting point of, e.g., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

In other aspects of this embodiment, a mixture of pharmaceutically-acceptable lipids includes a mixture PEG fatty acid esters having a melting point of, e.g., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., about 50° C. In aspects of this embodiment, a mixture of pharmaceutically-acceptable lipids includes a mixture PEG fatty acid esters having a melting point of, e.g., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

In other aspects of this embodiment, a mixture of pharmaceutically-acceptable lipids includes a mixture of mono-, di-, and/or triglycerides and PEG fatty acid esters having a melting point of, e.g., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., about 50° C. In aspects of this embodiment, a mixture of pharmaceutically-acceptable lipids includes a mixture of mono-, di-, and/or triglycerides and PEG fatty acid esters having a melting point of, e.g., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

Commercially available mixtures of pharmaceutically-acceptable lipids include, without limitation, mixtures of PEG-6 sterate and ethylene glycol palmitostearate and PEG-32 stearate (TEFOSE® 1500; TEFOSE® 63), mixtures of triceteareth-4 phosphate and ethylene glycol palmitostearate and diethylene glycol palmitostearate (SEDEFOS® 75), mixtures of glycerol monostearate and PEG-75 stearate (GELOT®), mixtures of cetyl alcohol and ethoxylated fatty alcohols (seteth-2-, steareth-20) (EMULCIRE®), mixtures of saturated $C_{10}$-$C_{18}$ triglycerides having a melting point around 33° C. (GELUCIRE® 33/01), mixtures of saturated $C_{10}$-$C_{18}$ triglycerides having a melting point around 39° C. (GELUCIRE® 39/01), mixtures of saturated $C_{10}$-$C_{18}$ triglycerides having a melting point around 43° C. (GELUCIRE® 43/01), mixtures of glycerol monostearate 40-55 (type I) and diglycerides (GELEOL® Mono and Diglycerides), and mixtures of medium-chain triglycerides (LABRAFAC® Lipophile WL 1349).

Aspects of the present specification disclose, in part, a pharmaceutically-acceptable stabilizing agent. A stabilizing agent reduces or eliminates formation of esters of a therapeutic compound that may result as a unwanted reaction with the particular solvent used. A stabilizing agent include, without limitation, water, a sacrificial acid comprising a fatty acid component and acetic acid, ethyl acetate, a sodium acetate/acetic acid (E262), a monoglyceride, an acetylated monoglyceride, a diglyceride, an acetylated monoglyceride, an acetylated diglyceride, a fatty acid, and a fatty acid salt.

In one embodiment, a pharmaceutically-acceptable stabilizing agent may comprise a pharmaceutically-acceptable emulsifying agent. An emulsifying agent (also known as an emulgent) is a substance that stabilizes an emulsion comprising a liquid dispersed phase and a liquid continuous phase by increasing its kinetic stability. Thus, in situations where the solvent and adjuvant used to make a pharmaceutical composition disclosed herein are normally immiscible, an emulsifying agent disclosed herein is used to create a homogenous and stable emulsion. An emulsifying agent includes, without limitation, a surfactant, a polysaccharide, a lectin, and a phospholipid.

In an aspect of this embodiment, an emulsifying agent may comprise a surfactant. As used hereon, the term "surfactant" refers to a natural or synthetic amphiphilic compound. A surfactant can be non-ionic, zwitterionic, or ionic. Non-limiting examples of surfactants include polysorbates like polysorbate 20 (TWEEN® 20), polysorbate 40 (TWEEN® 40), polysorbate 60 (TWEEN® 60), polysorbate 61 (TWEEN® 61), polysorbate 65 (TWEEN® 65), polysorbate 80 (TWEEN® 80), and polysorbate 81 (TWEEN® 81); poloxamers (polyethylene-polypropylene copolymers), like Poloxamer 124 (PLURONIC® L44), Poloxamer 181 (PLURONIC® L61), Poloxamer 182 (PLURONIC® L62), Poloxamer 184 (PLURONIC® L64), Poloxamer 188 (PLURONIC® F68), Poloxamer 237 (PLURONIC® F87), Poloxamer 338 (PLURONIC® L108), Poloxamer 407 (PLURONIC® F127), polyoxyethyleneglycol dodecyl ethers, like BRIJ® 30, and BRIJ® 35; 2-dodecoxyethanol (LUBROL®-PX); polyoxyethylene octyl phenyl ether (TRITON® X-100); sodium dodecyl sulfate (SDS); 3-[(3-Cholamidopropyl)dimethylammonio]-1-propanesulfonate (CHAPS); 3-[(3-Cholamidopropyl)dimethylammonio]-2-hydroxy-1-propanesulfonate (CHAPSO); sucrose monolaurate; and sodium cholate. Other non-limiting examples of surfactant excipients can be found in, e.g., Ansel, supra, (1999); Gennaro, supra, (2000); Hardman, supra, (2001); and Rowe, supra, (2003), each of which is hereby incorporated by reference in its entirety.

In an aspect of this embodiment, an emulsifying agent may comprise a polysaccharide. Non-limiting examples of polysaccharides include guar gum, agar, alginate, calgene, a dextran (like dextran 1K, dextran 4K, dextran 40K, dextran 60K, and dextran 70K), dextrin, glycogen, inulin, starch, a starch derivative (like hydroxymethyl starch, hydroxyethyl starch, hydroxypropyl starch, hydroxybutyl starch, and hydroxypentyl starch), hetastarch, cellulose, FICOLL, methyl cellulose (MC), carboxymethyl cellulose (CMC), hydroxyethyl cellulose (HEC), hydroxypropyl cellulose (HPC), hydroxyethyl methyl cellulose (NEMC), hydroxypropyl methyl cellulose (HPMC); polyvinyl acetates (PVA); polyvinyl pyrrolidones (PVP), also known as povidones, having a K-value of less than or equal to 18, a K-value greater than 18 or less than or equal to 95, or a K-value greater than 95, like PVP 12 (KOLLIDON® 12), PVP 17 (KOLLIDON® 17), PVP 25 (KOLLIDON® 25), PVP 30 (KOLLIDON® 30), PVP 90 (KOLLIDON® 90); and polyethylene imines (PEI).

In an aspect of this embodiment, an emulsifying agent may comprise a lectin. Lectins are sugar-binding proteins that are highly specific for their sugar moieties. Lectins may be classified according to the sugar moiety that they bind to, and include, without limitation, mannose-binding lectins, galactose/N-acetylgalactosamine-binding lectins, N-acetylgluxosamine-binding lectins, N-acetylneuramine-binding lectins, N-acetylneuraminic acid-binding lectins, and fucose-binding lectins. Non-limiting examples of surfactants include concanavain A, lentil lectin, snowdrop lectin, Roin, peanut agglutinin, jacain, hairy vetch lectin, wheat germ agglutinin, elderberry lectin, *Maackia anurensis leukoagglutinin, Maackia anurensis hemoagglutinin, Ulex europaeus agglutinin,* and *Aleuria aurantia lectin.*

In an aspect of this embodiment, an emulsifying agent may comprise a phospholipid. The structure of the phospholipid generally comprises a hydrophobic tail and a hydrophilic head and is amphipathic in nature. Most phospholipids contain a diglyceride, a phosphate group, and a simple organic molecule such as choline; one exception to this rule is sphingomyelin, which is derived from sphingosine instead of glycerol. Phospholipids include, without limitation, diacylglycerides and phosphosphingolipids. Non-limiting examples of diacylglycerides include a phosphatidic acid (phosphatidate) (PA), a phosphatidylethanolamine (cephalin) (PE), a phosphatidylcholine (lecithin) (PC), a phosphatidylserine (PS), and a phosphoinositide including phosphatidylinositol (PI), phosphatidylinositol phosphate (PIP), phosphatidylinositol bisphosphate (PIP2), and phosphatidylinositol triphosphate (PIP3). Non-limiting examples of phosphosphingolipids include a ceramide phosphorylcholine (sphingomyelin) (SPH), ceramide phosphorylethanolamine (sphingomyelin) (Cer-PE), and ceramide phosphorylglycerol.

In one embodiment, a pharmaceutically-acceptable stabilizing agent does not comprise a pharmaceutically-acceptable emulsifying agent.

In another embodiment, a pharmaceutical composition does not comprise a pharmaceutically-acceptable emulsifying agent.

The pharmaceutical compositions disclosed herein act as a delivery system that enable a therapeutic compound disclosed herein to be more effectively delivered or targeted to a cell type, tissue, organ, or region of the body in a manner that more effectively inhibits a pain response. This inhibition results in an improved treatment of a severe pain. For example, a pharmaceutical composition disclosed herein may facilitate the delivery of a therapeutic compound disclosed herein into macrophages. One possible mechanism that achieves this selective biodistribution is that the pharmaceutical compositions disclosed herein may be designed to take advantage of the activity of chylomicrons. Chylomicrons are relatively large lipoprotein particles having a diameter of 75 nm to 1,200 nm. Comprising triglycerides (85-92%), phospholipids (6-12%), cholesterol (1-3%) and apolipoproteins (1-2%), chylomicrons transport dietary lipids from the intestines to other locations in the body. Chylomicrons are one of the five major groups of lipoproteins, the others being VLDL, IDL, low-density lipoproteins (LDL), high-density lipoproteins (HDL), that enable fats and cholesterol to move within the water-based solution of the bloodstream.

During digestion, fatty acids and cholesterol undergo processing in the gastrointestinal tract by the action of pancreatic juices including lipases and emulsification with bile salts to generate micelles. These micelles allow the absorption of lipid as free fatty acids by the absorptive cells of the small intestine, known as enterocytes. Once in the enterocytes, triglycerides and cholesterol are assembled into nascent chylomicrons. Nascent chylomicrons are primarily composed of triglycerides (85%) and contain some cholesterol and cholesteryl esters. The main apolipoprotein component is apolipoprotein B-48 (APOB48). These nascent chylomicrons are released by exocytosis from enterocytes into lacteals, lymphatic vessels originating in the villi of the small intestine, and are then secreted into the bloodstream at the thoracic duct's connection with the left subclavian vein.

While circulating in lymph and blood, chylomicrons exchange components with HDL. The HDL donates apolipoprotein C-II (APOC2) and apolipoprotein E (APOE) to the nascent chylomicron and thus converts it to a mature chylomicron (often referred to simply as "chylomicron"). APOC2 is the cofactor for lipoprotein lipase (LPL) activity. Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown into lipoproteins (VLDL, LDL and HDL). These lipoproteins are processed and stored by competent cells, including, e.g., hepatocytes, adipocytes and macrophages. Thus, without wishing to be limited by any theory, upon oral administration, a pharmaceutical composition disclosed herein can be processed into micelles while in the gastrointestinal tract, absorbed by enterocytes and assembled into nascent chylomicrons, remain associated with chylomicron remnants taken up by the liver, and ultimately loaded into macrophages which are present in tissues experiencing pain.

As another example, a pharmaceutical composition disclosed herein may facilitate the delivery of a therapeutic compound disclosed herein into dentritic cells. One possible mechanism to achieve selective biodistribution of the pharmaceutical compositions disclosed herein may be to take advantage of the endocytotic/phagocytotic activity of dentritic cells. Dendritic cells are immune cells forming part of the mammalian immune system. The main function of dendritic cells is to process antigen material and present it on the surface to other cells of the immune system. Thus, dendritic cells function as antigen-presenting cells that act as messengers between innate and adaptive immunity. Dendritic cells are present in tissues in contact with the external environment, such as, e.g., the skin (where there is a specialized dendritic cell type called Langerhans cells) and the inner lining of the nose, lungs, stomach and intestines. These cells can also be found in an immature state in the blood. Once activated, they migrate to the lymph nodes where they interact with T cells and B cells to initiate and shape the adaptive immune response. Dendritic cells are known to endocytose and phagocytose lipid particles as part of their environmental monitoring and antigen presentation processes. Without wishing to be limited by any theory, upon topical or inhalatory administration, a pharmaceutical composition disclosed herein can penetrate into the skin or inner lining of the nose, lungs, stomach and intestines, be endocytosed/phagocytosed by dentritic cells, and ultimately loaded into T cells and/or B cells which are present in tissues experiencing pain.

Aspects of the present specification disclose, in part, a method of preparing a pharmaceutical composition disclosed herein. A method disclosed herein comprises the step of contacting a pharmaceutically-acceptable adjuvant disclosed herein with a therapeutic compound disclosed herein under conditions which allow the therapeutic compound to dissolve in the pharmaceutically-acceptable adjuvant, thereby forming a pharmaceutical composition disclosed herein.

Aspects of the present specification disclose, in part, a method of preparing a pharmaceutical composition disclosed herein. A method disclosed herein comprises the steps of a) contacting a pharmaceutically-acceptable solvent disclosed herein with a therapeutic compound disclosed herein under conditions which allow the therapeutic compound to dissolve in the pharmaceutically-acceptable solvent, thereby forming a solution; and b) contacting the solution formed in step (a) with a pharmaceutically-acceptable adjuvant disclosed herein under conditions which allow the formation of a pharmaceutical composition. The methods of preparing disclosed herein may further comprise a step (c) of removing the pharmaceutically-acceptable solvent from the pharmaceutical composition.

The amount of a therapeutic compound that is contacted with the pharmaceutically-acceptable solvent in step (a) of the method may be in any amount desired. Factors used to determine the amount of a therapeutic compound used include, without limitation, the final amount the therapeutic compound desired in the pharmaceutical composition, the desired concentration of a therapeutic compound in the solution, the hydrophobicity of the therapeutic compound, the lipophobicity of the therapeutic compound, the temperature under which the contacting step (a) is performed, and the time under which the contacting step (a) is performed, the particular formulation desired, and the particular route of delivery of the pharmaceutical compound.

The volume of a pharmaceutically-acceptable solvent used in step (a) of the method may be any volume desired. Factors used to determine the volume of a pharmaceutically-acceptable solvent used include, without limitation, the final amount of a pharmaceutical composition desired, the desired concentration of a therapeutic compound in the solution, the hydrophobicity of the therapeutic compound, and the lipophobicity of the therapeutic compound, the particular formulation desired, and the particular route of delivery of the pharmaceutical compound.

In aspects of this embodiment, the amount of a therapeutic compound that is contacted with the solvent in step (a) may be, e.g., at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In other aspects of this embodiment, the amount of a therapeutic compound that is contacted with the solvent in step (a) may be in the range of, e.g., about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In other aspects of this embodiment, the amount of a therapeutic compound that is dissolved in the solvent in step (a) may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, or about 200 mg to about 1,500 mg.

Step (a) may be carried out at room temperature, in order to allow a therapeutic compound to dissolve fully in the pharmaceutically-acceptable solvent. However, in other embodiments of the method, Step (a) may be carried out at a temperature that is greater than room temperature. In aspects of this embodiment, Step (a) may be carried out at a temperature that is, e.g., greater than 21° C., greater than 25° C., greater than 30° C., greater than 35° C. or greater than 37° C., greater than 40° C., greater than 42° C., greater than 45° C., greater than 50° C., greater than 55° C., or greater than 60° C. In aspects of this embodiment, Step (a) may be carried out at a temperature that is between, e.g., about 20° C. to about 30° C., about 25° C. to about 35° C., about 30° C. to about 40° C., about 35° C. to about 45° C., about 40° C. to about 50° C., about 45° C. to about 55° C., or about 50° C. to about 60° C. In certain cases, Step (a) may be carried out at temperatures below room temperature, in order to allow a therapeutic compound to dissolve fully in solvent. However, in other embodiments of the method, step (a) may be carried out at a temperature that is less than room temperature, e.g., less than 10° C., greater than 5° C., greater than 0° C., greater than −10° C. or greater than −20° C. The contacting in Step (a) may comprise mixing the therapeutic compound and the pharmaceutically-acceptable solvent, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the therapeutic compound is fully dissolved in the solvent.

After contacting, the concentration of a therapeutic compound disclosed herein in the solution may be in any concentration desired. In aspects of this embodiment, the concentration of a therapeutic compound disclosed herein in the solution may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the concentration of a therapeutic compound disclosed herein in the solution may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

The volume of a pharmaceutically-acceptable adjuvant used in step (b) of the method may be any volume desired. Factors used to determine the volume of a pharmaceutically-acceptable adjuvant used include, without limitation, the final amount of a pharmaceutical composition desired, the desired concentration of a therapeutic compound in the pharmaceutical composition, the ratio of solvent:adjuvant used, and the miscibility of solvent and adjuvant, the particular formulation desired, and the particular route of delivery of the pharmaceutical compound.

In aspects of this embodiment, the ratio of solution:adjuvant may be, e.g., at least 5:1, at least 4:1, at least 3:1, at least 2:1, at least 0:1, at least 1:1, at least 1:2, at least 1:3, at least 1:4, at least 1:5, at least 1:6, at least 1:7, at least 1:8, at least 1:9, at least 1:10, at least 1:15, at least 1:20, or at least 1:25. In other aspects of this embodiment, the ratio of solution:adjuvant may be in a range of, e.g., about 5:1 to about 1:25, about 4:1 to about 1:25, about 3:1 to about 1:25, about 2:1 to about 1:25, about 0:1 to about 1:25, about 1:1 to about 1:25, about 1:2 to about 1:25, about 1:3 to about 1:25, about 1:4 to about 1:25, about 1:5 to about 1:25, about 5:1 to about 1:20, about 4:1 to about 1:20, about 3:1 to about 1:20, about 2:1 to about 1:20, about 0:1 to about 1:20, about 1:1 to about 1:20, about 1:2 to about 1:20, about 1:3 to about 1:20, about 1:4 to about 1:20, about 1:5 to about 1:20, about 5:1 to about 1:15, about 4:1 to about 1:15, about 3:1 to about 1:15, about 0:1 to about 1:15, about 2:1 to about 1:15, about 1:1 to about 1:15, about 1:2 to about 1:15, about 1:3 to about 1:15, about 1:4 to about 1:15, about 1:5 to about 1:15, about 5:1 to about 1:12, about 4:1 to about 1:12, about 3:1 to about 1:12, about 2:1 to about 1:12, about 0:1 to about 1:12, about 1:1 to about 1:12, about 1:2 to about 1:12, about 1:3 to about 1:12, about 1:4 to about 1:12, about 1:5 to about 1:12, about 1:6 to about 1:12, about 1:7 to about 1:12, about 1:8 to about 1:12, about 5:1 to about 1:10, about 4:1 to about 1:10, about 3:1 to about 1:10, about 2:1 to about 1:10, about 0:1 to about 1:10, about 1:1 to about 1:10, about 1:2 to about 1:10, about 1:3 to about 1:10, about 1:4 to about 1:10, about 1:5 to about 1:10, about 1:6 to about 1:10, about 1:7 to about 1:10, or about 1:8 to about 1:10.

Step (b) may be carried out at room temperature, in order to allow the solution comprising the therapeutic compound to form the pharmaceutical composition. However, in other embodiments of the method, Step (b) may be carried out at a temperature that is greater than room temperature. In aspects of this embodiment, Step (b) may be carried out at a temperature that is, e.g., greater than 21° C., greater than 25° C., greater than 30° C., greater than 35° C. or greater than 37° C., greater than 40° C., greater than 42° C., greater than 45° C., greater than 50° C., greater than 55° C., or greater than 60° C. In aspects of this embodiment, Step (a)

may be carried out at a temperature that is between, e.g., about 20° C. to about 30° C., about 25° C. to about 35° C., about 30° C. to about 40° C., about 35° C. to about 45° C., about 40° C. to about 50° C., about 45° C. to about 55° C., or about 50° C. to about 60° C. In certain cases, Step (b) may be carried out at temperatures below room temperature, in order to allow a therapeutic compound to dissolve fully in a pharmaceutically-acceptable solvent. However, in other embodiments of the method, step (b) may be carried out at a temperature that is less than room temperature, e.g., less than 10° C., greater than 5° C., greater than 0° C., greater than −10° C. or greater than −20° C. The contacting in Step (b) may comprise mixing the solution and the pharmaceutically-acceptable adjuvant, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the pharmaceutical composition is formed.

In certain embodiments, a rapid cooling step may be used to reduce the temperature of a pharmaceutical composition disclosed herein after its formation. For example, a rapid cooling step may be used in procedures were temperatures greater than room temperature are used to allow a therapeutic compound to dissolve fully in the pharmaceutically-acceptable solvent and/or to allow the solution comprising the therapeutic compound to form the pharmaceutical composition. In aspects of this embodiment, a rapid cooling step results in a temperature decrease of, e.g., about 30° C. in 20 minutes, about 25° C. in 20 minutes, about 20° C. in 20 minutes, about 15° C. in 20 minutes, about 30° C. in 15 minutes, about 25° C. in 15 minutes, about 20° C. in 15 minutes, about 15° C. in 15 minutes, about 30° C. in 10 minutes, about 25° C. in 10 minutes, about 20° C. in 10 minutes, about 15° C. in 10 minutes, about 30° C. in 5 minutes, about 25° C. in 5 minutes, about 20° C. in 5 minutes, about 15° C. in 5 minutes. In other aspects of this embodiment, a rapid cooling step results in a temperature decrease of, e.g., about 20° C. to about 30° C. in 20 minutes, about 20° C. to about 30° C. in 15 minutes, about 20° C. to about 30° C. in 10 minutes, about 20° C. to about 30° C. in 5 minutes, about 15° C. to about 25° C. in 20 minutes, about 15° C. to about 25° C. in 15 minutes, about 15° C. to about 25° C. in 10 minutes, about 15° C. to about 25° C. in 5 minutes, about 10° C. to about 20° C. in 20 minutes, about 10° C. to about 20° C. in 15 minutes, about 10° C. to about 20° C. in 10 minutes, or about 10° C. to about 20° C. in 5 minutes.

In yet aspects of this embodiment, a rapid cooling step results in a temperature decrease of, e.g., about 2.0° C./minute, about 1.9° C./minute, about 1.8° C./minute, about 1.7° C./minute, about 1.6° C./minute, about 1.5° C./minute, about 1.4° C./minute, about 1.3° C./minute, about 1.2° C./minute, about 1.1° C./minute, about 1.0° C./minute, about 0.9° C./minute, about 0.8° C./minute, about 0.7° C./minute, about 0.6° C./minute, about 0.5° C./minute, about 0.4° C./minute, about 0.3° C./minute, about 0.2° C./minute, or about 0.1° C./minute. In still aspects of this embodiment, a rapid cooling step results in a temperature decrease of, e.g., about 0.1° C. to about 0.4° C./minute, about 0.2° C. to about 0.6° C./minute, about 0.4° C. to about 0.8° C./minute, about 0.6° C. to about 1.0° C./minute, about 0.8° C. to about 1.2° C./minute, about 1.0° C. to about 1.4° C./minute, about 1.2° C. to about 1.6° C./minute, about 1.4° C. to about 1.8° C./minute, about 1.6° C. to about 2.0° C./minute, about 0.1° C. to about 0.5° C./minute, about 0.5° C. to about 1.0° C./minute, about 1.0° C. to about 1.5° C./minute, about 1.5° C. to about 2.0° C./minute, about 0.5° C. to about 1.5° C./minute, or about 1.0° C. to about 2.0° C./minute.

In some embodiments, temperatures greater than room temperature employed in either Step (a) or Step (b) or both may be used to remove the solvent from a pharmaceutical composition. In other embodiment, removal of solvent from a pharmaceutical composition requires a separate Step (c). In Step (c), the solvent removal from a pharmaceutical composition may be accomplished using one of a variety of procedures known in the art, including, without limitation, evaporation, dialyzation, distillation, lypholization, and filtration. These removal procedures may be done under conditions of ambient atmosphere, under low pressure, or under a vacuum and either at ambient temperature or at temperatures requiring heating.

In one embodiment, Step (c) may result in the complete removal of a pharmaceutically-acceptable solvent from the pharmaceutical composition disclosed herein. In aspects of this embodiment, Step (c) may result in, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 93%, at least 95%, at least 97%, or at least 99% removal of a pharmaceutically-acceptable solvent from the pharmaceutical composition disclosed herein.

Step (c) is conducted at a temperature that allows for the evaporation of a pharmaceutically-acceptable solvent disclosed herein, and as such, an evaporation temperature is solvent dependant. Factors which influence an evaporation temperature of a solvent disclosed herein include, without limitation, the particular solvent used, the amount of solvent present, the particular therapeutic compound present, the particular adjuvant present, the stability of the therapeutic compound present, the reactivity of the therapeutic compound present, the particular atmospheric pressure used, the time desired for complete evaporation. Generally, a pharmaceutical composition will require heating if the evaporation step is conducted at ambient pressure, e.g., 1 atm. However, under high vacuum conditions, the evaporation step may be conducted at temperatures below ambient temperature, e.g., less than 22° C.

In one embodiment, removal of solvent from the pharmaceutical composition disclosed herein may be carried out at ambient atmospheric pressure and at a temperature above ambient temperature. In aspects of this embodiment, removal of solvent from the pharmaceutical composition disclosed herein may be carried out at ambient atmospheric pressure and at a temperature of, e.g., more than 25° C., more than 30° C., more than 35° C., more than 40° C., more than 45° C., more than 50° C., more than 55° C., more than 60° C., more than 65° C., more than 70° C., more than 80° C., or more than 25° C. In other aspects of this embodiment, removal of solvent from the pharmaceutical composition disclosed herein may be carried out at ambient atmospheric pressure and at a temperature in a range of, e.g., about 25° C. to about 100° C., about 25° C. to about 95° C., about 25° C. to about 90° C., about 25° C. to about 85° C., about 25° C. to about 80° C., about 25° C. to about 75° C., about 25° C. to about 70° C., about 25° C. to about 65° C., or about 25° C. to about 60° C.

In another embodiment, removal of solvent from the pharmaceutical composition disclosed herein may be carried out under vacuum and at a temperature below ambient temperature. In aspects of this embodiment, removal of solvent from the pharmaceutical composition disclosed herein may be carried out under vacuum and at a temperature of, e.g., less than 20° C., less than 18° C., less than 16° C., less than 14° C., less than 12° C., less than 10° C., less than 8° C., less than 6° C., less than 4° C., less than 2° C., or less than 0° C. In other aspects of this embodiment, removal of solvent from the pharmaceutical composition disclosed herein may be carried out under vacuum and at a temperature in a range of, e.g., about −20° C. to about 20° C., about −20° C. to about 18° C., about −20° C. to about 16° C., about −20° C. to about 14° C., about −20° C. to about 12° C., about −20° C. to about 10° C., about −20° C. to about 8° C., about −20° C. to about 6° C., about −20° C. to about 4° C., about −20° C. to about 2° C., about −20° C. to about 0° C., about −15° C. to about 20° C., about −10° C. to about 20° C., about −5° C. to about 20° C., about 0° C. to about 20° C., about −10° C. to about 20° C., about −10° C. to about 18° C., about −10° C. to about 16° C., about −10° C. to about 14° C., about −10° C. to about 12° C., about −10° C. to about 10° C., about −10° C. to about 8° C., about −10° C. to about 6° C., about −10° C. to about 4° C., about −10° C. to about 2° C., or about −10° C. to about 0° C.

The final concentration of a therapeutic compound disclosed herein in a pharmaceutical composition disclosed herein may be of any concentration desired. In an aspect of this embodiment, the final concentration of a therapeutic compound in a pharmaceutical composition may be a therapeutically effective amount. In other aspects of this embodiment, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

A pharmaceutical composition produced using the methods disclosed herein may be formulated for either local or systemic delivery using topical, enteral or parenteral routes of administration. Additionally, a therapeutic compound disclosed herein may be formulated by itself in a pharmaceutical composition, or may be formulated together with one or more other therapeutic compounds disclosed herein in a single pharmaceutical composition.

A pharmaceutical composition produced using the methods disclosed herein may be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phase, such as, e.g., an emulsion. A pharmaceutical composition disclosed herein intended for such administration may be prepared according to any method known to the art for the manufacture of pharmaceutical compositions. Semi-solid formulations suitable for topical administration include, without limitation, ointments, creams, salves, and gels.

A liquid formulation can be formed by using various lipids like oils of other fatty acids that remain as liquids in the temperature range desired. In an embodiment, a pharmaceutical composition disclosed herein is liquid at room temperature. In aspects of this embodiment, a pharmaceutical composition disclosed herein may be formulated to be a liquid at a temperature of, e.g., about 25° C. or higher, about 23° C. or higher, about 21° C. or higher, about 19° C. or higher, about 17° C. or higher, about 15° C. or higher, about 12° C. or higher, about 10° C. or higher, about 8° C. or higher, about 6° C. or higher, about 4° C. or higher, or about 0° C. or higher.

In liquid and semi-solid formulations, a concentration of a therapeutic compound disclosed herein typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In semi-solid and solid formulations, an amount of a therapeutic compound disclosed herein typically may be between about 0.01% to about 45% by weight. In aspects of this embodiment, an amount of a therapeutic compound disclosed herein may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

In one embodiment, a liquid formulation comprises a therapeutic compound, a glycol ether, a partially-hydrogenated fat, an oil, and an alcohol. In an aspect of this embodiment, a liquid formulation comprises about 15% to about 35% by weight of therapeutic compound, about 5% to about 25% by weight of glycol ether, about 15% to about 40% by weight of partially-hydrogenated fat, about 15% to about 40% of an oil, and about 1% to about 15% of an alcohol. In another aspect of this embodiment, a liquid formulation comprises about 20% to about 30% by weight of therapeutic compound, about 10% to about 20% by weight of glycol ether, about 20% to about 35% by weight of partially-hydrogenated fat, about 20% to about 35% of an oil, and about 2% to about 10% of an alcohol. In yet another aspect of this embodiment, a liquid formulation comprises about 23% to about 27% by weight of therapeutic compound, about 13% to about 17% by weight of glycol ether, about 25% to about 30% by weight of partially-hydrogenated fat, about 25% to about 30% of an oil, and about 4% to about 8% of an alcohol. In still another aspect of this embodiment, a liquid formulation comprises about 24% to about 26% by weight of therapeutic compound, about 14% to about 16% by weight of glycol ether, about 26% to about 28% by weight of partially-hydrogenated fat, about 26% to about 28% of an oil, and about 5% to about 7% of an alcohol. In other aspects of this embodiment, an oil is rapeseed oil or theobroma oil.

In another embodiment, a liquid formulation comprises a therapeutic compound, a glycol ether, a glyceryl monolinoleate, an oil, and an alcohol. In an aspect of this embodiment, a liquid formulation comprises about 15% to about 35% by weight of therapeutic compound, about 5% to about 25% by weight of glycol ether, about 15% to about 40% by weight of glyceryl monolinoleate, about 15% to about 40% of an oil, and about 1% to about 15% of an alcohol. In another aspect of this embodiment, a liquid formulation comprises about 20% to about 30% by weight of therapeutic compound, about 10% to about 20% by weight of glycol ether, about 20% to about 35% by weight of glyceryl monolinoleate, about 20% to about 35% of an oil, and about 2% to about 10% of an alcohol. In yet another aspect of this embodiment, a liquid formulation comprises about 23% to about 27% by weight of therapeutic compound, about 13% to about 17% by weight of glycol ether, about 25% to about 30% by weight of glyceryl monolinoleate, about 25% to about 30% of an oil, and about 4% to about 8% of an alcohol. In still another aspect of this embodiment, a liquid formulation comprises about 24% to about 26% by weight of therapeutic compound, about 14% to about 16% by weight of glycol ether, about 26% to about 28% by weight of glyceryl monolinoleate, about 26% to about 28% of an oil, and about 5% to about 7% of an alcohol. In other aspects of this embodiment, an oil is rapeseed oil or theobroma oil.

In another embodiment, a liquid formulation comprises an ibuprofen, a diethylene glycol monoethyl ether, a glyceryl monolinoleate, an oil, and an alcohol. In an aspect of this embodiment, a liquid formulation comprises about 15% to about 35% by weight of an ibuprofen, about 5% to about 25% by weight of diethylene glycol monoethyl ether, about 15% to about 40% by weight of glyceryl monolinoleate, about 15% to about 40% of an oil, and about 1% to about 15% of an alcohol. In another aspect of this embodiment, a liquid formulation comprises about 20% to about 30% by weight of an ibuprofen, about 10% to about 20% by weight of diethylene glycol monoethyl ether, about 20% to about 35% by weight of glyceryl monolinoleate, about 20% to about 35% of an oil, and about 2% to about 10% of an alcohol. In yet another aspect of this embodiment, a liquid formulation comprises about 23% to about 27% by weight of an ibuprofen, about 13% to about 17% by weight of diethylene glycol monoethyl ether, about 25% to about 30% by weight of glyceryl monolinoleate, about 25% to about 30% of an oil, and about 4% to about 8% of an alcohol. In still another aspect of this embodiment, a liquid formulation comprises about 24% to about 26% by weight of an ibuprofen, about 14% to about 16% by weight of diethylene glycol monoethyl ether, about 26% to about 28% by weight of glyceryl monolinoleate, about 26% to about 28% of an oil, and about 5% to about 7% of an alcohol. In other aspects of this embodiment, an ibuprofen may be a free acid of a salt of ibuprofen. In other aspects of this embodiment, an oil is rapeseed oil or theobroma oil.

In one embodiment, a liquid formulation comprises a therapeutic compound, an ester of an alcohol, and an oil. In an aspect of this embodiment, a liquid formulation comprises about 1% to about 10% by weight of therapeutic compound, about 1% to about 10% by weight of an ester of an alcohol, and about 80% to about 98% of an oil. In another aspect of this embodiment, a liquid formulation comprises about 2% to about 8% by weight of therapeutic compound, about 1% to about 7% by weight of an ester of an alcohol, and about 85% to about 97% of an oil. In yet another aspect of this embodiment, a liquid formulation comprises about 3% to about 7% by weight of therapeutic compound, about 2% to about 6% by weight of an ester of an alcohol, and about 87% to about 95% of an oil. In still another aspect of this embodiment, a liquid formulation comprises about 4% to about 6% by weight of therapeutic compound, about 3% to about 5% by weight of an ester of an alcohol, and about 90% to about 92% of an oil. In other aspects of this embodiment, an oil is rapeseed oil or theobroma oil.

In another embodiment, a liquid formulation comprises a therapeutic compound, an ethyl acetate, and an oil. In an aspect of this embodiment, a liquid formulation comprises about 1% to about 10% by weight of therapeutic compound, about 1% to about 10% by weight of an ethyl acetate, and about 80% to about 98% of an oil. In another aspect of this embodiment, a liquid formulation comprises about 2% to about 8% by weight of therapeutic compound, about 1% to about 7% by weight of an ethyl acetate, and about 85% to about 97% of an oil. In yet another aspect of this embodiment, a liquid formulation comprises about 3% to about 7% by weight of therapeutic compound, about 2% to about 6% by weight of an ethyl acetate, and about 87% to about 95% of an oil. In still another aspect of this embodiment, a liquid formulation comprises about 4% to about 6% by weight of therapeutic compound, about 3% to about 5% by weight of an ethyl acetate, and about 90% to about 92% of an oil. In other aspects of this embodiment, an oil is rapeseed oil or theobroma oil.

In another embodiment, a liquid formulation comprises an ibuprofen, an ethyl acetate, and an oil. In an aspect of this embodiment, a liquid formulation comprises about 1% to about 10% by weight of an ibuprofen, about 1% to about 10% by weight of an ethyl acetate, and about 80% to about 98% of an oil. In another aspect of this embodiment, a liquid formulation comprises about 2% to about 8% by weight of an ibuprofen, about 1% to about 7% by weight of an ethyl acetate, and about 85% to about 97% of an oil. In yet another aspect of this embodiment, a liquid formulation comprises about 3% to about 7% by weight of an ibuprofen, about 2% to about 6% by weight of an ethyl acetate, and about 87% to about 95% of an oil. In still another aspect of this embodiment, a liquid formulation comprises about 4% to about 6% by weight of an ibuprofen, about 3% to about 5% by weight of an ethyl acetate, and about 90% to about 92% of an oil. In other aspects of this embodiment, an ibuprofen may be a free acid of a salt of ibuprofen. In other aspects of this embodiment, an oil is rapeseed oil or theobroma oil.

In one embodiment, a solid or semi-solid formulation disclosed herein is formulated without a hydrophilic solvent like water. Such formulations result in the formation of co-crystals of the lipids and therapeutic compound. Stated another way, such formulations do not form liposomal emulsions and/or micellular particles, which require hydrophilic solvent.

In one embodiment, a solid formulation comprises a therapeutic compound, a hard fat, a partially-hydrogenated fat, and a polyethylene glycol. In an aspect of this embodiment, a solid formulation comprises about 1% to about 30% by weight of therapeutic compound, about 8% to about 70% by weight of hard fat, about 2% to about 65% by weight of partially-hydrogenated fat, and about 1% to about 15% of polyethylene glycol. In another aspect of this embodiment, a solid formulation comprises about 10% to about 30% by weight of therapeutic compound, about 20% to about 50% by weight of hard fat, about 10% to about 30% by weight of partially-hydrogenated fat, and about 5% to about 15% of polyethylene glycol. In yet another aspect of this embodiment, a solid formulation comprises about 20% to about 30% by weight of therapeutic compound, about 30% to about 50% by weight of hard fat, about 10% to about 30% by weight of partially-hydrogenated fat, and about 7% to about 13% of polyethylene glycol. In still another aspect of this embodiment, a solid formulation comprises about 20% to about 30% by weight of therapeutic compound, about 35% to about 50% by weight of hard fat, about 15% to about 25% by weight of partially-hydrogenated fat, and about 7% to about 13% of polyethylene glycol. In a further aspect of this embodiment, a solid formulation comprises about 23% to about 27% by weight of therapeutic compound, about 41% to about 47% by weight of hard fat, about 18% to about 22% by weight of partially-hydrogenated fat, and about 9% to about 11% of polyethylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a therapeutic compound, a mixture of mono-, di-, and triglycerides and PEG fatty acid esters, a glyceryl monolinoleate, and a polyethylene glycol. In an aspect of this embodiment, a solid formulation comprises about 1% to about 30% by weight of therapeutic compound, about 8% to about 70% by weight of a mixture of mono-, di-, and triglycerides and PEG fatty acid esters, about 2% to about 65% by weight of a glyceryl monolinoleate, and about 1% to about 15% of polyethylene glycol. In another aspect of this embodiment, a solid formulation comprises about 10% to about 30% by weight of therapeutic compound, about 20% to about 50% by weight of a mixture of mono-, di-, and triglycerides and PEG fatty acid esters, about 10% to about 30% by weight of a glyceryl monolinoleate, and about 5% to about 15% of polyethylene glycol. In yet another aspect of this embodiment, a solid formulation comprises about 20% to about 30% by weight of therapeutic compound, about 30% to about 50% by weight of a mixture of mono-, di-, and triglycerides and PEG fatty acid esters, about 10% to about 30% by weight of a glyceryl monolinoleate, and about 7% to about 13% of polyethylene glycol. In still another aspect of this embodiment, a solid formulation comprises about 20% to about 30% by weight of therapeutic compound, about 35% to about 50% by weight of a mixture of mono-, di-, and triglycerides and PEG fatty acid esters, about 15% to about 25% by weight of a glyceryl monolinoleate, and about 7% to about 13% of polyethylene glycol. In a further aspect of this embodiment, a solid formulation comprises about 23% to about 27% by weight of therapeutic compound, about 41% to about 47% by weight of a mixture of mono-, di-, and triglycerides and PEG fatty acid esters, about 18% to about 22% by weight of a glyceryl monolinoleate, and about 9% to about 11% of polyethylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises an ibuprofen, a mixture of mono-, di-, and triglycerides and PEG fatty acid esters, a glyceryl monolinoleate, and a polyethylene glycol. In an aspect of this embodiment, a solid formulation comprises about 1% to about 30% by weight of an ibuprofen, about 8% to about 70% by weight of a mixture of mono-, di-, and triglycerides and PEG fatty acid esters, about 2% to about 65% by weight of a glyceryl monolinoleate, and about 1% to about 15% of polyethylene glycol. In another aspect of this embodiment, a solid formulation comprises about 10% to about 30% by weight of an ibuprofen, about 20% to about 50% by weight of a mixture of mono-, di-, and triglycerides and PEG fatty acid esters, about 10% to about 30% by weight of a glyceryl monolinoleate, and about 5% to about 15% of polyethylene glycol. In yet another aspect of this embodiment, a solid formulation comprises about 20% to about 30% by weight of an ibuprofen, about 30% to about 50% by weight of a mixture of mono-, di-, and triglycerides and PEG fatty acid esters, about 10% to about 30% by weight of a glyceryl monolinoleate, and about 7% to about 13% of polyethylene glycol. In still another aspect of this embodiment, a solid formulation comprises about 20% to about 30% by weight of an ibuprofen, about 35% to about 50% by weight of a mixture of mono-, di-, and triglycerides and PEG fatty acid esters, about 15% to about 25% by weight of a glyceryl monolinoleate, and about 7% to about 13% of polyethylene glycol. In a further aspect of this embodiment, a solid formulation comprises about 23% to about 27% by weight of an ibuprofen, about 41% to about 47% by weight of a mixture of mono-, di-, and triglycerides and PEG fatty acid esters, about 18% to about 22% by weight of a glyceryl monolinoleate, and about 9% to about 11% of polyethylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a therapeutic compound, a hard fat, a partially-hydrogenated fat, a polyethylene glycol, and a propylene glycol. In an aspect of this embodiment, a solid formulation comprises about 1% to about 30% by weight of therapeutic compound, about 8% to about 70% by weight of hard fat, about 2% to about 65% by weight of partially-hydrogenated fat, about 1% to about 15% of polyethylene glycol, and about 1% to about 15% of propylene glycol. In another aspect of this embodiment, a solid formulation comprises about 10% to about 30% by weight of therapeutic compound, about 20% to about 50% by weight of hard fat, about 10% to about 30% by weight of partially-hydrogenated fat, about 5% to about 15% of polyethylene glycol, and about 5% to about 15% of propylene glycol. In yet another aspect of this embodiment, a solid formulation comprises about 20% to about 30% by weight of therapeutic compound, about 30% to about 50% by weight of hard fat, about 10% to about 30% by weight of partially-hydrogenated fat, about 7% to about 13% of polyethylene glycol, and about 7% to about 13% of propylene glycol. In still another aspect of this embodiment, a solid formulation comprises about 20% to about 30% by weight of therapeutic compound, about 35% to about 50% by weight of hard fat, about 15% to about 25% by weight of partially-hydrogenated fat, about 7% to about 13% of polyethylene glycol, and about 7% to about 13% of propylene glycol. In a further aspect of this embodiment, a solid formulation comprises about 23% to about 27% by weight of therapeutic compound, about 41% to about 47% by weight of hard fat, about 18% to about 22% by weight of partially-hydrogenated fat, about 9% to about 11% of polyethylene glycol, and about 9% to about 11% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises a therapeutic compound, a mixture of mono-, di-, and triglycerides and PEG fatty acid esters, a glyceryl monolinoleate, a polyethylene glycol, and a propylene glycol. In an aspect of this embodiment, a solid formulation comprises about 1% to about 30% by weight of therapeutic compound, about 8% to about 70% by weight of a mixture of mono-, di-, and triglycerides and PEG fatty acid esters, about 2% to about 65% by weight of a glyceryl monolinoleate, about 1% to about 15% of polyethylene glycol, and about 1% to about 15% of propylene glycol. In another aspect of this embodiment, a solid formulation comprises about 10% to about 30% by weight of therapeutic compound, about 20% to about 50% by weight of a mixture of mono-, di-, and triglycerides and PEG fatty acid esters, about 10% to about 30% by weight of a glyceryl monolinoleate, about 5% to about 15% of polyethylene glycol, and about 5% to about 15% of propylene glycol. In yet another aspect of this embodiment, a solid formulation comprises about 20% to about 30% by weight of therapeutic compound, about 30% to about 50% by weight of a mixture of mono-, di-, and triglycerides and PEG fatty acid esters, about 10% to about 30% by weight of a glyceryl monolinoleate, and about 7% to about 13% of polyethylene glycol, and about 7% to about 13% of propylene glycol. In still another aspect of this embodiment, a solid formulation comprises about 20% to about 30% by weight of therapeutic compound, about 35% to about 50% by weight of a mixture of mono-, di-, and triglycerides and PEG fatty acid esters, about 15% to about 25% by weight of a glyceryl monolinoleate, about 7% to about 13% of polyethylene glycol, and about 7% to about 13% of propylene glycol. In a further aspect of this embodiment, a solid formulation comprises about 23% to about 27% by weight of therapeutic compound, about 41% to about 47% by weight of a mixture of mono-, di-, and triglycerides and PEG fatty acid esters, about 18% to about 22% by weight of a glyceryl monolinoleate, about 9% to about 11% of polyethylene glycol, and about 9% to about 11% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a solid formulation comprises an ibuprofen, a mixture of mono-, di-, and triglycerides and PEG fatty acid esters, a glyceryl monolinoleate, a polyethylene glycol, and a propylene glycol. In an aspect of this embodiment, a solid formulation comprises about 1% to about 30% by weight of an ibuprofen, about 8% to about 70% by weight of a mixture of mono-, di-, and triglycerides and PEG fatty acid esters, about 2% to about 65% by weight of a glyceryl monolinoleate, about 1% to about 15% of polyethylene glycol, and about 1% to about 15% of propylene glycol. In another aspect of this embodiment, a solid formulation comprises about 10% to about 30% by weight of an ibuprofen, about 20% to about 50% by weight of a mixture of mono-, di-, and triglycerides and PEG fatty acid esters, about 10% to about 30% by weight of a glyceryl monolinoleate, about 5% to about 15% of polyethylene glycol, and about 5% to about 15% of propylene glycol. In yet another aspect of this embodiment, a solid formulation comprises about 20% to about 30% by weight of an ibuprofen, about 30% to about 50% by weight of a mixture of mono-, di-, and triglycerides and PEG fatty acid esters, about 10% to about 30% by weight of a glyceryl monolinoleate, and about 7% to about 13% of polyethylene glycol, and about 7% to about 13% of propylene glycol. In still another aspect of this embodiment, a solid formulation comprises about 20% to about 30% by weight of an ibuprofen, about 35% to about 50% by weight of a mixture of mono-, di-, and triglycerides and PEG fatty acid esters, about 15% to about 25% by weight of a glyceryl monolinoleate, about 7% to about 13% of polyethylene glycol, and about 7% to about 13% of propylene glycol. In a further aspect of this embodiment, a solid formulation comprises about 23% to about 27% by weight of an ibuprofen, about 41% to about 47% by weight of a mixture of mono-, di-, and triglycerides and PEG fatty acid esters, about 18% to about 22% by weight of a glyceryl monolinoleate, about 9% to about 11% of polyethylene glycol, and about 9% to about 11% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a hard fat, a partially-hydrogenated fat, a polyethylene glycol, and a propylene glycol. In an aspect of this embodiment, a semi-solid formulation comprises about 15% to about 55% by weight of therapeutic compound, about 7% to about 20% by weight of hard fat, about 20% to about 50% by weight of partially-hydrogenated fat, about 7% to about 20% of polyethylene glycol, and about 1% to about 8% of propylene glycol. In another aspect of this embodiment, a semi-solid formulation comprises about 20% to about 50% by weight of therapeutic compound, about 8% to about 18% by weight of hard fat, about 25% to about 45% by weight of partially-hydrogenated fat, about 8% to about 18% of polyethylene glycol, and about 2% to about 6% of propylene glycol. In another aspect of this embodiment, a semi-solid formulation comprises about 20% to about 50% by weight of therapeutic compound, about 10% to about 16% by weight of hard fat, about 25% to about 45% by weight of partially-hydrogenated fat, about 10% to about 16% of polyethylene glycol, and about 2% to about 6% of propylene glycol. In yet another aspect of this embodiment, a semi-solid formulation comprises about 20% to about 50% by weight of therapeutic compound, about 11% to about 15% by weight of hard fat, about 30% to about 40% by weight of partially-hydrogenated fat, about 11% to about 15% of polyethylene glycol, and about 3% to about 5% of propylene glycol. In still another aspect of this embodiment, a semi-solid formulation comprises about 25% to about 44% by weight of therapeutic compound, about 12% to about 14% by weight of hard fat, about 32% to about 39% by weight of partially-hydrogenated fat, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a mixture of mono-, di-, and triglycerides and PEG fatty acid esters, a glyceryl monolinoleate, a polyethylene glycol, and a propylene glycol. In an aspect of this embodiment, a semi-solid formulation comprises about 15% to about 55% by weight of therapeutic compound, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 20% to about 50% by weight of therapeutic compound, about 8% to about 18% by weight of a mixture of mono-, di-, and triglycerides and PEG fatty acid esters, about 25% to about 45% by weight of a glyceryl monolinoleate, about 8% to about 18% of polyethylene glycol, and about 2% to about 6% of propylene glycol. In another aspect of this embodiment, a semi-solid formulation comprises about 20% to about 50% by weight of therapeutic compound, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 20% to about 50% by weight of therapeutic compound, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 25% to about 44% by weight of therapeutic compound, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises an ibuprofen, a mixture of mono-, di-, and triglycerides and PEG fatty acid esters, a glyceryl monolinoleate, a polyethylene glycol, and a propylene glycol. In an aspect of this embodiment, a semi-solid formulation comprises about 15% to about 55% by weight of an ibuprofen, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 20% to about 50% by weight of an ibuprofen, about 8% to about 18% by weight of a mixture of mono-, di-, and triglycerides and PEG fatty acid esters, about 25% to about 45% by weight of a glyceryl monolinoleate, about 8% to about 18% of polyethylene glycol, and about 2% to about 6% of propylene glycol. In another aspect of this embodiment, a semi-solid formulation comprises about 20% to about 50% by weight of an ibuprofen, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 20% to about 50% by weight of an ibuprofen, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 25% to about 44% by weight of an ibuprofen, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a hard fat, a partially-hydrogenated fat, a polyethylene glycol, and a propylene glycol. In an aspect of this embodiment, a semi-solid formulation comprises about 10% to about 35% by weight of a free acid of a therapeutic compound, about 1% to about 30% by weight of a salt of a therapeutic compound, about 7% to about 20% by weight of hard fat, about 20% to about 50% by weight of partially-hydrogenated fat, about 7% to about 20% of polyethylene glycol, and about 1% to about 8% of propylene glycol. In another aspect of this embodiment, a semi-solid formulation comprises about 15% to about 30% by weight of a free acid of a therapeutic compound, about 1% to about 25% by weight of a salt of a therapeutic compound, about 10% to about 16% by weight of hard fat, about 25% to about 45% by weight of partially-hydrogenated fat, about 10% to about 16% of polyethylene glycol, and about 2% to about 6% of propylene glycol. In yet another aspect of this embodiment, a semi-solid formulation comprises about 15% to about 30% by weight of a free acid of a therapeutic compound, about 1% to about 25% by weight of a salt of a therapeutic compound, about 11% to about 15% by weight of hard fat, about 30% to about 40% by weight of partially-hydrogenated fat, about 11% to about 15% of polyethylene glycol, and about 3% to about 5% of propylene glycol. In still another aspect of this embodiment, a semi-solid formulation comprises about 20% to about 24% by weight of a free acid of a therapeutic compound, about 5% to about 20% by weight of a salt of a therapeutic compound, about 12% to about 14% by weight of hard fat, about 32% to about 39% by weight of partially-hydrogenated fat, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises a therapeutic compound, a mixture of mono-, di-, and triglycerides and PEG fatty acid esters, a glyceryl monolinoleate, a polyethylene glycol, and a propylene glycol. In an aspect of this embodiment, a semi-solid formulation comprises about 10% to about 35% by weight of a free acid of a therapeutic compound, about 1% to about 30% by weight of a salt of a therapeutic compound, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 15% to about 30% by weight of a free acid of a therapeutic compound, about 1% to about 25% by weight of a salt of a therapeutic compound, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 15% to about 30% by weight of a free acid of a therapeutic compound, about 1% to about 25% by weight of a salt of a therapeutic compound, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 20% to about 24% by weight of a free acid of a therapeutic compound, about 5% to about 20% by weight of a salt of a therapeutic compound, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

In another embodiment, a semi-solid formulation comprises an ibuprofen, a mixture of mono-, di-, and triglycerides and PEG fatty acid esters, a glyceryl monolinoleate, a polyethylene glycol, and a propylene glycol. In an aspect of this embodiment, a semi-solid formulation comprises about 10% to about 35% by weight of a free acid of an ibuprofen, about 1% to about 30% by weight of a salt of an ibuprofen, about 7% to about 20% by weight of a mixture of mono-, di-, and triglycerides and PEG fatty acid esters, about 20% to about 50% by weight of a glyceryl monolinoleate, about 7% to about 20% of polyethylene glycol, and about 1% to about 8% of propylene glycol. In another aspect of this embodiment, a semi-solid formulation comprises about 15% to about 30% by weight of a free acid of an ibuprofen, about 1% to about 25% by weight of a salt of an ibuprofen, about 10% to about 16% by weight of a mixture of mono-, di-, and triglycerides and PEG fatty acid esters, about 25% to about 45% by weight of a glyceryl monolinoleate, about 10% to about 16% of polyethylene glycol, and about 2% to about 6% of propylene glycol. In yet another aspect of this embodiment, a semi-solid formulation comprises about 15% to about 30% by weight of a free acid of an ibuprofen, about 1% to about 25% by weight of a salt of an ibuprofen, about 11% to about 15% by weight of a mixture of mono-, di-, and triglycerides and PEG fatty acid esters, about 30% to about 40% by weight of a glyceryl monolinoleate, and about 11% to about 15% of polyethylene glycol, and about 3% to about 5% of propylene glycol. In still another aspect of this embodiment, a semi-solid formulation comprises about 20% to about 24% by weight of a free acid of an ibuprofen, about 5% to about 20% by weight of a salt of an ibuprofen, about 12% to about 14% by weight of a mixture of mono-, di-, and triglycerides and PEG fatty acid esters, about 32% to about 39% by weight of a glyceryl monolinoleate, about 12% to about 14% of polyethylene glycol, and about 4% of propylene glycol. In other aspects of this embodiment, a polyethylene glycol is, e.g., a PEG 100, a PEG 200, a PEG 300, a PEG 400, a PEG 500, a PEG 600, or a PEG 700.

A solid or semi-solid formulation disclosed herein takes advantage of the different melting point temperatures of the various adjuvants like fatty acids. Formation of a solid or semi-solid dosage form can be by modifying the respective concentrations of the fatty acids comprising a pharmaceutical composition disclosed herein. For example, linolenic acid has a melting point temperature ($T_m$) of about −11° C., linoleic acid has a $T_m$ of about −5° C., oleic acid has a $T_m$ of about 16° C., palmitic acid has a $T_m$ of about 61-62° C., and Stearic acid has a $T_m$ of about 67-72° C. Increasing the proportion(s) of palmitic, stearic or oleic acid would increase the overall melting temperature of a composition, while, conversely, increasing the proportion(s) of linoleic and linolenic acid would decrease the melting temperature of a composition. Thus, by controlling the types and amounts of the adjuvant components added, a pharmaceutical composition disclosed herein can be made that is substantially solid or semi-solid at room temperature, but melts when it is ingested, and reaches body temperature. The resulting melted composition readily forms micelles which are absorbed by the intestine, assembled into chylomicrons, and ultimately absorbed by macrophages. The solid dosage form may be a powder, granule, tablet, capsule or suppository.

In an embodiment, a pharmaceutical composition disclosed herein is solid at room temperature. In aspects of this embodiment, a pharmaceutical composition disclosed herein may be formulated to be a solid at a temperature of, e.g., about 35° C. or lower, about 33° C. or lower, about 31° C. or lower, about 29° C. or lower, about 27° C. or lower, about 25° C. or lower, about 23° C. or lower, about 21° C. or lower, about 19° C. or lower, about 17° C. or lower, about 15° C. or lower, about 12° C. or lower, about 10° C. or lower, about 8° C. or lower, about 6° C. or lower, about 4° C. or lower, or about 0° C. or lower.

In other aspects of this embodiment, a pharmaceutical composition disclosed has a melting point temperature of, e.g., 5° C. or higher, 10° C. or higher, 15° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, or 35° C. or higher. In other aspects of this embodiment, a pharmaceutical composition disclosed has a melting point temperature in the range of, e.g., about 5° C. to about 24° C., about 10° C. to about 24° C. about 22° C. to about 24° C., about 23° C. to about 25° C., about 24° C. to about 26° C., about 25° C. to about 27° C., about 26° C. to about 28° C., about 27° C. to about 29° C., about 28° C. to about 30° C., about 29° C. to about 31° C., about 30° C. to about 32° C., about 31° C. to about 33° C., about 32° C. to about 34° C., or about 33° C. to about 35° C. In other aspects of this embodiment, a pharmaceutical composition disclosed has a melting point temperature in the range of, e.g., about 22° C. to about 26° C., about 24° C. to about 28° C., about 26° C. to about 30° C., about 28° C. to about 32° C., or about 30° C. to about 34° C.

Aspects of the present specification disclose, in part, a method of treating an individual with a severe pain condition. In one embodiment, the method comprises the step of administering to an individual in need thereof a pharmaceutical composition disclosed herein, wherein administration reduces a symptom associated with the severe pain, thereby treating the individual.

Aspects of the present specification disclose, in part, treating an individual suffering from a severe pain condition. As used herein, the term "treating," refers to reducing or eliminating in an individual a clinical symptom of a severe pain condition; or delaying or preventing in an individual the onset of a clinical symptom of a severe pain condition. For example, the term "treating" can mean reducing a symptom of a condition characterized by a severe pain condition by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a severe pain condition are well known and can be determined by a person of ordinary skill in the art by taking into account factors, including, without limitation, the location of the severe pain condition, the cause of the severe pain condition, the severity of the severe pain condition, and/or the tissue or organ affected by the severe pain condition. Those of skill in the art will know the appropriate symptoms or indicators associated with a specific type of severe pain condition and will know how to determine if an individual is a candidate for treatment as disclosed herein.

Pain may be measured using one or more pain thresholds. Pain thresholds are measured by gradually increasing the intensity of a stimulus such as electric current or heat applied to the body. The pain perception threshold is the point at which the stimulus begins to hurt, and the pain tolerance threshold is reached when the individual acts to stop the pain.

Pain may be measured using one or more pain scale questionnaires. Although a self-reported questionaire by an individual suffering from a severe pain condition tend to be the most reliable measure of pain, reports from health care professionals may also be used. A number of pain measurement scales have been developed including, without limitation, Alder Hey Triage Pain Score, Behavioral Pain Scale (BPS), Brief Pain Inventory (BPI), Checklist of Nonverbal Pain Indicators (CNPI), Critical-Care Pain Observation Tool (CPOT), COMFORT scale, Dallas Pain Questionnaire, Descriptor differential scale (DDS), Disease-Specific Pain Scale (DSPI), Dolorimeter Pain Index (DPI), Faces Pain Scale-Revised (FPS-R), Face Legs Activity Cry Consolability scale, Lequesne algofunctional index, Original index, McGill Pain Questionnaire (MPQ), Multidimensional Pain Inventory (MPI), Neck Pain and Disability Scale—NPAD, Numerical 11 point box (BS-11), Numeric Rating Scale (NRS-11), Pediatric Pain Questionnaire (PPQ), Roland-Morris Back Pain Questionnaire, Visual analog scale (VAS), and Wong-Baker FACES Pain Rating Scale. As one example, a NRS-11 scale is an 11-point scale for patient self-reporting that ranks the pain being experienced on a scale of 0 to 10, with 0 being no pain at all, 1-3 being mild pain that interferes little with activities of daily life, 4-6 being moderate pain that interferes significantly with activities of daily life, and 7-10 being severe pain that completely interferes with activities of daily life. Quality can be established by having the individual complete the McGill Pain Questionnaire indicating which words best describe their pain.

Severe pain condition symptoms include, without limitation, a coldness, a numbness, an itching, a paresthesias, an electric shock sensation, a burning sensation, an ice-burn sensation, dysesthesia, allodynia, hyperalgesia, hyperpathia, a somatic pain sensation, and a visceral pain sensation. The actual symptoms associated with a severe pain condition are well known and can be determined by a person of ordinary skill in the art by taking into account factors, including, without limitation, the location of the severe pain, the cause of the severe pain, the severity of the severe pain, the tissue or organ affected, and the associated disorder.

A pharmaceutical composition disclosed herein are useful to treat severe pain. Pain is any unpleasant sensory and/or emotional experience associated with actual or potential tissue damage, or described in terms of such damage. Pain may occur in varying degrees of severity and is usually a consequence of an injury, a disease, or an emotional disorder, although the underlying cause may or may not be apparent to a healthcare provider. A severe pain is one where the severity of the pain response significantly interferes or prevents an individual from performing one or more activities of daily life. An activity of daily life (ADL) is an activity an individual normally does such as feeding, bathing, dressing, grooming, work, homemaking, and leisure. ADLs may be categorized based on whether the activity is a basic, an instrumental, or an occupational one. Basic ADLs (BADLs) comprise self-care tasks, including, e.g., personal hygiene and grooming, dressing and undressing, self feeding, functional transfers (getting into and out of bed or wheelchair, getting onto or off toilet, etc.), bowel and bladder management, and ambulation (walking with or without use of an assistive device (walker, cane, or crutches) or using a wheelchair). Instrumental ADLs (IADLs) are not necessary for fundamental functioning, but let an individual live independently in a community. IADLs include, e.g., performing housework, taking medications as prescribed, managing money, shopping for groceries or clothing, using communication devices, using technology, using transportation within the community. Occupational ADLs (OADLs) are generally optional in nature and may be delegated to others. OADLs include, e.g., caring of others (including selecting and supervising caregivers), caring of pets, child rearing, using of communication devices, community mobility, financial management, health management and maintenance, meal preparation and cleanup, and safety procedures and emergency responses.

As used herein, the term "severe pain" comprises any acute, subacute, chronic nociceptive, pathological pain, or psychological pain. In aspects of this embodiment, a severe pain is not an inflammatory pain or a pain whose primary origin is due to an inflammatory response.

A severe pain condition may be classified according to duration and pattern of occurrence, such as, e.g., acute pain, subacute pain, and chronic pain. Acute pain is an organic pain state that is typically transitory and of sudden onset, lasting only until the noxious stimulus is removed and/or the underlying damage or pathology has healed. Chronic pain is an organic pain state that is persistent and extends beyond the expected period of healing and may be present continuously or intermediately. Subacute pain is an organic pain state that refers to a pain that is somewhere in between acute pain and chronic pain. Although somewhat arbitrary, the distinction between acute, subacute, and chronic pain may be defined based on the interval of time from onset. Thus, an acute pain is one that lasts less then one month, a subacute pain is one that lasts from one to six months, and a chronic pain is one that lasts six months or more.

A severe pain condition may also be classified as 1) a nociceptive pain; 2) a pathological pain; and 3) an inflammatory pain.

In one embodiment, a severe pain condition comprises a nociceptive pain. Nociceptive pain is a severe pain condition where an organic pain state is caused by a noxious insult or injury of peripheral nerve fibers that respond only to stimuli approaching or exceeding harmful intensity (nociceptors), and is commonly described as an aching pain. This type of pain is associated with damage to non-neural tissue, such as skin, muscles, visceral organs, joints, tendons, or bones, and is represented by a normally functioning somatosensory nervous system. Nociceptive pain may be classified according to the mode of noxious stimulation, such as, e.g., thermal pain, mechanical pain, and chemical pain, or according to the location of the pain, such as, e.g., somatic pain or visceral pain.

In one embodiment, a severe pain condition comprises a somatic pain. Somatic pain is a nociceptive pain that originates from ligaments, tendons, bones, blood vessels, and even nerves themselves. It is detected with somatic nociceptors. The scarcity of pain receptors in these areas produces a dull, poorly-localized pain of longer duration than cutaneous pain. Non-limiting examples of somatic pain include 1) excessive muscle tension can be caused, for example, by a sprain or a strain; 2) repetitive motion disorders can result from overuse of the hands, wrists, elbows, shoulders, neck, back, hips, knees, feet, legs, or ankles; 3) muscle disorders causing somatic pain include, for example, a polymyositis, a dermatomyositis, a lupus, a fibromyalgia, a polymyalgia rheumatica, and a rhabdomyolysis; 4) myalgia including, e.g., muscle pain caused by overuse, over-stretching, viral infection, metabolic myopathy, a nutritional deficiency, or chronic fatigue syndrome; 5) infections including, e.g., an abscess, a trichinosis, an influenza, a Lyme disease, a malaria, a Rocky Mountain spotted fever, Avian influenza, the common cold, community-acquired pneumonia, meningitis, monkeypox, Severe Acute Respiratory Syndrome, toxic shock syndrome, trichinosis, typhoid fever, and upper respiratory tract infection; and 6) drugs including, e.g., cocaine, a statin for lowering cholesterol (such as atorvastatin, simvastatin, and lovastatin), and an ACE inhibitor for lowering blood pressure (such as enalapril and captopril). Somatic pain may be classified as a superficial somatic pain or a deep somatic pain. Superficial somatic pain is initiated by activation of nociceptors in the skin or other superficial tissue, and is sharp, well-defined and clearly located. Examples of injuries that produce superficial somatic pain include minor wounds and minor (first degree) burns. Deep somatic pain is initiated by stimulation of nociceptors in ligaments, tendons, bones, blood vessels, fasciae and muscles, and is dull, aching, poorly localized pain. Examples include sprains and broken bones.

In one embodiment, a severe pain condition comprises a visceral pain. Visceral pain is a nociceptive pain that is initiated by stimulation of nociceptors in the body's organs and internal cavities typically caused by stretching or ischemia. Visceral pain is a diffuse, poorly localized pain and may be described as aching pain, sickening pain, dull pain, squeezing pain, and/or deep pain, and it may be accompanied by nausea and vomiting. Visceral pain is extremely difficult to localize, and several injuries to visceral tissue may exhibit "referred" pain, where the sensation is localized to an area completely unrelated to the site of injury. The even greater scarcity of nociceptors in these areas produces pain that is usually more aching and of a longer duration than somatic pain. Non-limiting examples of somatic pain include 1) functional visceral pain including, e.g., an irritable bowel syndrome and a chronic functional abdominal pain (CFAP), a functional constipation and a functional dyspepsia, a non-cardiac chest pain (NCCP) and a chronic abdominal pain; 2) chronic gastrointestinal inflammation including, e.g., a gastritis, an inflammatory bowel disease, like, e.g., a Crohn's disease, an ulcerative colitis, a microscopic colitis, a diverticulitis and a gastroenteritis; an interstitial cystitis; an intestinal ischemia; a cholecystitis; an appendicitis; a gastroesophageal reflux; an ulcer, a nephrolithiasis, an urinary tract infection, a pancreatitis and a hernia; 3) autoimmune pain including, e.g., a sarcoidosis and a vasculitis; 4) organic visceral pain including, e.g., pain resulting from a traumatic, inflammatory or degenerative lesion of the gut or produced by a tumor impinging on sensory innervation; and 5) treatment-induced visceral pain including, e.g., a pain attendant to chemotherapy therapy or a pain attendant to radiation therapy.

In one embodiment, a severe pain condition comprises a pathological pain. Damage A pathological pain is a severe pain condition where an organic pain state caused by disease or damage to any part of the nervous system or by caused by an abnormal functioning of the nervous system. This type of pain is associated with damage to neural tissue and an abnormally functioning somatosensory nervous system, rather than stimulation of pain receptors. Non-limiting examples of a pathological pain include neuropathic pain and dysfunctional pain.

In one embodiment, a severe pain condition comprises a neuropathic pain. Damage Neuropathic pain is a pathological pain where an organic pain state is caused by damage or disease of the somatosensory nervous system, resulting in abnormal sensory firing from the peripheral nervous system, central nervous systems, or both. Neuropathic pain may involve spontaneous or evoked pain, and may have continuous and/or episodic (paroxysmal) components. Neuropathic pain may be associated with dysesthesia (abnormal pain responses), such as, e.g., allodynia (a painful response to a stimulus that normally is not painful), hyperalgesia (an accentuated response to a painful stimulus that usually causes only a mild discomfort), and hyperpathia (where a short discomfort becomes a prolonged severe pain). Painful sensations can be described as a coldness, numbness, itching, paresthesias (tingling or "pins and needles" sensation), an electric shock, and a burning or ice-burn pain. Non-limiting examples of a neuropathic pain include central neuropathic pain, peripheral neuropathic pain, and deafferentation pain.

In one embodiment, a severe pain condition comprises a central neuropathic pain. Damage or disease affecting nerves of the central nervous system is referred to as a central neuropathic pain. Typically, the damage or disease occurs as cerebral lesions, predominantly thalamic but may involve suprathalamic and infrathalamic regions. Generally, the onset of central neuropathic pain is usually delayed after the occurrence of the initial episode that results in damage to the central nervous system; onset of pain may occur during the phase of recovery from neurologic deficits. Central neuropathic pain may be present in post-stroke conditions including, e.g., thalamic infarction, brainstem infarction, or subarachnoid hemorrhage, cerebral venous thrombosis, cerebral tumors compressing the thalamus or brainstem, cerebral abscesses compressing the thalamus or brainstem, traumatic brain injury, post-surgical pain following brain or spine surgery, complications following brain surgery including thalamotomy for movement disorders, multiple sclerosis, and Parkinson disease, spinal cord injury, complications following spinal surgery including anterolateral cordotomy and commissural myelotomy, ischemic lesions including anterior spinal artery syndrome and Wallenberg syndrome, syringomyelia, radiation myelopathy, HIV myelopathy.

In one embodiment, a severe pain condition comprises a peripheral neuropathic pain. Damage or disease affecting sensory, motor, and/or autonomic nerves of the peripheral nervous system is referred to as a peripheral neuropathic pain. Peripheral neuropathic pain occurs when peripheral nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Symptoms also depend on whether the condition affects the whole body or just one nerve. Risk factors for neuropathy include diabetes, heavy alcohol use, exposure to certain chemicals and drugs, prolonged pressure on a nerve. Some people have a hereditary predisposition for peripheral neuropathy. The four cardinal patterns of peripheral neuropathic pain are mononeuropathy, mononeuropathic multiplex, polyneuropathy, and autonomic neuropathy.

In one embodiment, a severe pain condition comprises a mononeuropathic. A mononeuropathy is a peripheral neuropathy involving functional loss or pathological change affecting a single nerve or nerve group. Mononeuropathy is most often caused by damage to a local area resulting from injury or trauma, although occasionally systemic disorders may cause isolated nerve damage. The usual causes are direct trauma, prolonged pressure on the nerve, and compression of the nerve by swelling or injury to nearby body structures. The damage includes destruction of the myelin sheath (covering) of the nerve or of part of the nerve cell (the axon). This damage slows or prevents conduction of impulses through the nerve. Mononeuropathy may involve any part of the body. Mononeuropathic pain is associated with, e.g., a sciatic nerve dysfunction, a common peroneal nerve dysfunction. a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome or other focal entrapment neuropathy, and a sixth (abducent) nerve palsy In one embodiment, a severe pain condition comprises a mononeuropathic multiplex. A mononeuropathic multiplex is a peripheral neuropathy involving functional loss or pathological change that sequentially or simultaneously affects several non-contiguous nerves in an asymmetric manner. A neuropathic pain based on mononeuropathy multiplex may develop over days to years and typically presents with acute or subacute loss of sensory and motor function of individual nerves. The pattern of involvement is asymmetric; however, as the disease progresses deficit(s) becomes more confluent and symmetrical, making it difficult to differentiate from polyneuropathy. Mononeuropathic multiplex may also cause pain characterized as deep, aching pain that is worse at night, and frequently present in the lower back, hip, or leg. Mononeuropathic multiplex may also cause pain characterized as acute, unilateral, severe limb pain followed by anterior muscle weakness and loss of knee reflex. Mononeuropathic multiplex pain is associated with, e.g., diabetes mellitus, infections, such as, e.g., leprosy, lyme disease, HIV, and toxicity.

In one embodiment, a severe pain condition comprises a polyneuropathy. A polyneuropathy is a peripheral neuropathy involving functional loss or pathological change affecting multiple nerves throughout the body in a symmetric manner. A polyneuropathy may be acute and appear without warning, or chronic and develop gradually over a longer period of time. Many polyneuropathies have both motor and sensory involvement, and some also involve dysfunction of the autonomic nervous system. These disorders are often symmetrical, and usually due to various systematic illnesses and disease processes that affect the peripheral nervous system in its entirety. A polyneuropathy frequently affect the feet and hands, causing weakness, loss of sensation, pins-and-needle sensations or burning pain. Polyneuropathies can be classified in different ways, such as by cause, by speed of progression, or by the parts of the body involved. Classes of polyneuropathy are also distinguished by which part of the nerve cell is mainly affected: the axon, the myelin sheath, or the cell body.

In one embodiment, a severe pain condition comprises a distal axonopathy. Distal axonopathy, or "dying-back neuropathy", is the result of some metabolic or toxic derangement of a neuron. They may be caused by metabolic diseases such as diabetes, renal failure, deficiency syndromes such as malnutrition and alcoholism, or the effects of toxins or drugs such as chemotherapy. The most common cause of distal axonopathy is diabetes, and the most common distal axonopathy is diabetic neuropathy. They can be divided according to the type of axon affected: large-fiber, small-fiber, or both. The most distal portions of axons are usually the first to degenerate, and axonal atrophy advances slowly towards the nerve's cell body. If the cause is removed, regeneration is possible, though the prognosis depends on the duration and severity of the stimulus. People with distal axonopathies usually present with sensorimotor disturbances that have a symmetrical "stocking and glove" distribution. Deep tendon reflexes and autonomic nervous system functions are also lost or diminished in affected areas.

In one embodiment, a severe pain condition comprises a myelinopathy. Myelinopathy, or "demyelinating polyneuropathy", is due to a loss of myelin (or of the Schwann cells that make and contain it). This demyelination leaves the axon intact, but slows down or completely blocks the conduction of action potentials through the axon of the nerve cell. The most common cause is acute inflammatory demyelinating polyneuropathy (AIDP, the most common form of Guillain-Barré syndrome), though other causes include chronic inflammatory demyelinating polyneuropathy (CIDP), genetic metabolic disorders (e.g., leukodystrophy), and toxins.

In one embodiment, a severe pain condition comprises a neuronopathy. Neuronopathy is the result of destruction of peripheral nervous system neurons. They may be caused by motor neuron diseases, sensory neuronopathies (e.g., Herpes zoster), toxins or autonomic dysfunction. Neurotoxins may cause neuronopathies, such as the chemotherapy agent vincristine. A person with neuronopathy may present in different ways, depending on the cause, the way it affects the nerve cells, and the type of nerve cell that is most affected.

There are numerous conditions that can cause polyneuropathy. Peripheral neuropathic pain include, without limitation, neuropathies associated with systemic disease like diabetic neuropathy, neuropathies associated with metabolic conditions like alcoholic neuropathy and burning feet syndrome, neuropathies associated with viral infections like herpes zoster and HIV, neuropathies associated with nutritional deficiencies, neuropathies associated with toxins, neuropathies associated with tumor compression, neuropathies associated with remote manifestations of malignancies, neuropathies associated with drugs like chemotherapy, neuropathies associated with radiation, neuropathies associated with immune mediated disorders, and neuropathies associated with physical trauma to a nerve trunk. Polyneuropathic pain, includes, without limitation, post-polio syndrome, postmastectomy syndrome, diabetic neuropathy, alcohol neuropathy, amyloid, toxins, AIDS, hypothyroidism, uremia, vitamin deficiencies, chemotherapy-induced pain, 2',3'-didexoycytidine (ddC) treatment, Guillain-Barre syndrome or Fabry's disease.

In one embodiment, a severe pain condition comprises an autonomic neuropathy. An autonomic neuropathy is a peripheral neuropathy involving functional loss or pathological change affecting the non-voluntary, non-sensory nervous system (i.e., the autonomic nervous system). Autonomic neuropathy is a form of polyneuropathy which affects mostly the internal organs such as the bladder, muscles, the cardiovascular system, the digestive tract, and the genital organs.

Peripheral neuropathic pain may be present in systemic diseases, metabolic disorders, nutrient disorders, drug-induced disorders, traumatic injury, traumatic and entrapment syndromes, post-surgical pain surgery, complications following surgery, HIV sensory neuropathy, demyelinating polyradiculoneuropathy, postherpetic neuralgia, nerve root avulsions, cranial neuralgias like trigeminal neuralgia, neuropathic cancer pain, compression of peripheral nerves, nerve plexuses, and nerve roots, paraneoplastic peripheral neuropathy, ganglionopathy, complication of cancer therapies like chemotherapy, radiation, and surgery, and complex regional pain syndrome like Type 1 and Type 2.

In one embodiment, a severe pain condition comprises a neuralgia. A neuralgia is a peripheral neuropathic pain that radiates along the course of one or more specific nerves usually without any demonstrable pathological change in the nerve structure. The affected nerves are responsible for sensing touch, temperature and pressure. Simple stimuli such as eating, talking, washing the face, or any light touch or sensation can trigger an attack (even the sensation of a gentle breeze). The attacks can occur in clusters or as an isolated attack. Generally, a neuralgia causes short episodes of excruciating pain, usually for less than two minutes. However, in the atypical forms of neuralgia, the pain can also present as merely aching to severe pain and last for extended periods. Symptoms include sharp, stabbing pain or constant, burning pain located anywhere, usually on or near the surface of the body, in the same location for each episode; pain along the path of a specific nerve; impaired function of affected body part due to pain, or muscle weakness due to concomitant motor nerve damage; increased sensitivity of the skin or numbness of the affected skin area; and any touch or pressure is interpreted as pain. Movement may also be painful. A neuralgia, includes, without limitation, a trigeminal neuralgia, a glossopharyngeal neuralgia, a post-herpetic neuralgia (caused by, e.g., herpesvirus, syphilis and Lyme disease), a carpal tunnel syndrome, a meralgia paresthetica, a sciatica and an atypical facial pain.

In one embodiment, a severe pain condition comprises a Complex Regional Pain Syndrome (CRPS). A CRPS is a neuropathy resulting from sympathetically-maintained pain. Although unknown, mechanisms probably involve abnormal sympathetic-somatic nerve connections (ephapses), local inflammatory changes, and changes in the spinal cord. CRPS presents in two forms. CRPS 1 (reflex sympathetic dystrophy syndrome) is a chronic nerve disorder that occurs most often in the arms or legs after a minor or major injury. CRPS 1 is associated with severe pain; changes in the nails, bone, and skin; and an increased sensitivity to touch in the affected limb. CRPS 2 (causalgia) is caused by an identified injury to the nerve and results in a syndrome of sustained burning pain, allodynia, and hyperpathia after a traumatic nerve lesion, often combined with vasomotor and sudomotor dysfunction and later trophic changes.

In one embodiment, a severe pain condition comprises a referred pain. Referred pain arises from pain localized to an area separate from the site of pain stimulation. Often, referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot). Relieving the pressure on the nerve root may ameliorate the referred pain, provided that permanent nerve damage has not occurred. Myocardial ischaemia (the loss of blood flow to a part of the heart muscle tissue) is possibly the best known example of referred pain; the sensation can occur in the upper chest as a restricted feeling, or as an ache in the left shoulder, arm or even hand.

In one embodiment, a severe pain condition comprises a deafferentation pain. Damage or disease affecting peripheral or central afferent neural activity is referred to as a deafferentation pain. Deafferentation pain is due to partial or complete loss of the sensory input from a portion of the body, and can be caused by interruption of either peripheral sensory fibres or nerves from the central nervous system. The mechanism underlying this type of pain is unknown but may involve sensitization of central neurons, with lower activation thresholds and expansion of receptive fields. A deafferentation pain syndrome, includes, without limitation, a phantom pain, a brain injury, a spinal cord injury, a lumbar radiculopathy, a post-stroke pain, a paraplegia, avulsion of the brachial plexus or other types of lesions of peripheral nerves, a pathology of the central nervous system.

In one embodiment, a severe pain condition comprises a dysfunctional pain. Dysfunctional pain is a pathological pain where an organic pain state is caused by abnormal function of the somatosensory nervous system, but which are not initiated by an identifiable lesion of any part of the nervous system. Similar to neuropathic pain, dysfunctional pain is commonly described as a burning pain, a coldness, an electric shock, a "pins and needles" sensation, numbness and itching.

In one embodiment, a severe pain condition comprises a headache. A severe pain condition may be a headache (medically known as cephalgia) is a condition of mild to severe pain in the head; sometimes neck or upper back pain may also be interpreted as a headache. It may indicate an underlying local or systemic disease or be a disorder in itself. A headache includes, without limitation, a muscular/myogenic headache, a vascular headache, a traction headache, inflammatory headache, a chronic sinusitis headache, a hormone headache, a rebound headache, an organic headache, and an ictal headache.

In one embodiment, a severe pain condition comprises a muscular/myogenic headache. Muscular/myogenic headaches appear to involve the tightening or tensing of facial and neck muscles; they may radiate to the forehead. Tension headache is the most common form of myogenic headache. A tension headache is a condition involving pain or discomfort in the head, scalp, or neck, usually associated with muscle tightness in these areas. Tension headaches result from the contraction of neck and scalp muscles. One cause of this muscle contraction is a response to stress, depression or anxiety. Any activity that causes the head to be held in one position for a long time without moving can cause a headache. Such activities include typing or use of computers, fine work with the hands, and use of a microscope. Sleeping in a cold room or sleeping with the neck in an abnormal position may also trigger this type of headache. A tension-type headache, includes, without limitation, an episodic tension headache and a chronic tension headache.

In one embodiment, a severe pain condition comprises a vascular headache. The most common type of vascular headache is migraine. Other kinds of vascular headaches include cluster headaches, which cause repeated episodes of intense pain, and headaches resulting from high blood pressure.

In one embodiment, a severe pain condition comprises a migraine headache. A migraine is a heterogeneous disorder that generally involves recurring headaches. Migraines are different from other headaches because they occur with other symptoms, such as, e.g., nausea, vomiting, or sensitivity to light. In most people, a throbbing pain is felt only on one side of the head. Clinical features such as type of aura symptoms, presence of prodromes, or associated symptoms such as vertigo, may be seen in subgroups of patients with different underlying pathophysiological and genetic mechanisms. A migraine headache, includes, without limitation, a migraine without aura (common migraine), a migraine with aura (classic migraine), a menstrual migraine, a migraine equivalent (acephalic headache), a complicated migraine, an abdominal migraine and a mixed tension migraine.

In one embodiment, a severe pain condition comprises a cluster headache. Cluster headaches affect one side of the head (unilateral) and may be associated with tearing of the eyes and nasal congestion. They occurs in clusters, happening repeatedly every day at the same time for several weeks and then remitting.

In one embodiment, a severe pain condition comprises a sinusitis headache. Sinusitis is inflammation, either bacterial, fungal, viral, allergic or autoimmune, of the paranasal sinuses. Chronic sinusitis is one of the most common complications of the common cold. Symptoms include: Nasal congestion; facial pain; headache; fever; general malaise; thick green or yellow discharge; feeling of facial 'fullness' worsening on bending over. In a small number of cases, chronic maxillary sinusitis can also be brought on by the spreading of bacteria from a dental infection. Chronic hyperplastic eosinophilic sinusitis is a noninfective form of chronic sinusitis.

In one embodiment, a severe pain condition comprises a traction headache. Traction and inflammatory headaches are usually symptoms of other disorders, ranging from stroke to sinus infection.

In one embodiment, a severe pain condition comprises a rebound headache. Rebound headaches, also known as medication overuse headaches, occur when medication is taken too frequently to relieve headache. Rebound headaches frequently occur daily and can be very painful.

In one embodiment, a severe pain condition comprises a ictal headache. Idal headaches are headaches associated with seizure activity.

In one embodiment, a severe pain condition comprises a psychogenic pain. Psychogenic pain, also called psychalgia or somatoform pain, is pain caused, increased, or prolonged by mental, emotional, or behavioral factors. Headache, back pain, and stomach pain are sometimes diagnosed as psychogenic. Sufferers are often stigmatized, because both medical professionals and the general public tend to think that pain from a psychological source is not "real". However, specialists consider that it is no less actual or hurtful than pain from any other source. Individuals with long term pain frequently display psychological disturbance.

In one embodiment, a severe pain condition comprises an inflammatory pain. An inflammatory pain is a severe pain condition where an organic pain state is caused by the release of mediators at a site of tissue inflammation which activate and sensitize the nociceptive pain pathway. This type of pain is associated with any tissue damage caused by a chronic inflammatory response. Inflammatory pain may be associate with an arthritic disorder, an autoimmune disease, a connective tissue disorder, an injury, an infection, and a neuritis.

In one embodiment, a severe pain condition does not comprise an inflammatory pain.

In one embodiment, a severe pain condition is not caused by an inflammatory response.

A pharmaceutical composition disclosed herein is administered to an individual. An individual is typically a human being. Typically, any individual who is a candidate for a conventional severe pain treatment is a candidate for a severe pain treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to treating a severe pain condition refers to the minimum dose of a therapeutic compound disclosed herein necessary to achieve the desired therapeutic effect and includes a dose sufficient to reduce a symptom associated with a severe pain condition. The effectiveness of a therapeutic compound disclosed herein in treating a severe pain condition can be determined by observing an improvement in an individual based upon one or more clinical symptoms, and/or physiological indicators associated with the condition. An improvement in a severe pain condition also can be indicated by a reduced need for a concurrent therapy.

The appropriate effective amount of a therapeutic compound disclosed herein to be administered to an individual for a particular severe pain condition can be determined by a person of ordinary skill in the art by taking into account factors, including, without limitation, the type of the severe pain condition, the location of the severe pain condition, the cause of the severe pain condition, the severity of the severe pain condition, the degree of relief desired, the duration of relief desired, the particular therapeutic compound used, the rate of excretion of the therapeutic compound used, the pharmacodynamics of the therapeutic compound used, the nature of the other compounds to be included in the composition, the particular formulation, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

In aspects of this embodiment, a therapeutically effective amount of a therapeutic compound disclosed herein reduces a symptom associated with a severe pain condition by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a severe pain condition by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a severe pain condition by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic compound disclosed herein generally is in the range of about 0. 001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

Dosing can be single dosage or cumulative (serial dosing), and can be readily determined by one skilled in the art. For instance, treatment of a severe pain condition may comprise a one-time administration of an effective dose of a pharmaceutical composition disclosed herein. Alternatively, treatment of a severe pain condition may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Various routes of administration can be useful for administering a therapeutic compound disclosed herein, according to a method of treating a severe pain condition disclosed herein. A pharmaceutical composition may be administered to an individual by any of a variety of means depending, e.g., on the type of the severe pain condition to be treated, the location of the severe pain condition to be treated, the specific therapeutic compound or composition used, or other compound to be included in the composition, and the history, risk factors and symptoms of the individual. As such, topical, enteral or parenteral routes of administration may be suitable for of treating a severe pain condition disclosed herein and such routes include both local and systemic delivery of a therapeutic compound or composition disclosed herein. Compositions comprising either a single therapeutic compound disclosed herein, or two or more therapeutic compounds disclosed herein are intended for inhaled, topical, intranasal, sublingual, injection, infusion, instillation, rectal and/or vaginal use may be prepared according to any method known to the art for the manufacture of pharmaceutical compositions.

In one embodiment, upon administration to an individual, a pharmaceutical composition comprising a therapeutic compound disclosed herein results in a bio-distribution of the therapeutic compound different than a bio-distribution of the therapeutic compound included in the same pharmaceutical composition, except without an adjuvant disclosed herein.

In another embodiment, upon administration to an individual, a therapeutic compound of the pharmaceutical composition disclosed herein is delivered to a macrophage. Macrophages are one of the key cell types believed to be involved in the control of the inflammation response. The resultant high level of a therapeutic compound having anti-pain activity present in the macrophages results in a clinically effective treatment of a severe pain condition. In an aspect of this embodiment, upon administration to an individual, a therapeutically effective amount of a therapeutic compound of the pharmaceutical composition disclosed herein is preferentially delivered to a macrophage. In other aspect of this embodiment, upon administration to an individual, a therapeutic compound of the pharmaceutical composition disclosed herein is substantially delivered to a macrophage. In yet other aspect of this embodiment, upon administration to an individual, the amount of a therapeutic compound of the pharmaceutical composition disclosed herein delivered to a macrophage is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a macrophage is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a therapeutic compound of the pharmaceutical composition disclosed herein is delivered to a dentritic cell. Dendritic cells are one of the key cell types believed to coordinate the interplay between innate and adaptive immunity. The resultant high level of a therapeutic compound having anti-pain activity present in the dentritic cells results in a clinically effective treatment of a severe pain condition. In an aspect of this embodiment, upon administration to an individual, a therapeutically effective amount of a therapeutic compound of the pharmaceutical composition disclosed herein is preferentially delivered to a dentritic cell. In other aspect of this embodiment, upon administration to an individual, a therapeutic compound of the pharmaceutical composition disclosed herein is substantially delivered to a dentritic cell. In yet other aspect of this embodiment, upon administration to an individual, the amount of a therapeutic compound of the pharmaceutical composition disclosed herein delivered to a dentritic cell is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a dentritic cell is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a pharmaceutical composition disclosed herein reduces gastric irritation. In an aspect of this embodiment, a pharmaceutical composition disclosed herein substantially reduces gastric irritation. In yet another embodiment, upon administration to an individual, a pharmaceutical composition disclosed herein reduces gastric irritation when compared to the same pharmaceutical composition disclosed herein, except without the pharmaceutically-acceptable adjuvant. In an aspect of this embodiment, a pharmaceutical composition disclosed herein substantially reduces gastric irritation when compared to the same pharmaceutical composition disclosed herein, except without the pharmaceutically-acceptable adjuvant. In other aspects of this embodiment, a pharmaceutical composition disclosed herein reduces gastric irritation by, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In yet other aspects of this embodiment, a pharmaceutical composition disclosed herein reduces gastric irritation in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70%.

In another embodiment, upon administration to an individual, a pharmaceutical composition disclosed herein reduces intestinal irritation. In an aspect of this embodiment, a pharmaceutical composition disclosed herein substantially reduces intestinal irritation. In yet another embodiment, upon administration to an individual, a pharmaceutical composition disclosed herein reduces intestinal irritation when compared to the same pharmaceutical composition disclosed herein, except without the pharmaceutically-acceptable adjuvant. In an aspect of this embodiment, a pharmaceutical composition disclosed herein substantially reduces intestinal irritation when compared to the same pharmaceutical composition disclosed herein, except without the pharmaceutically-acceptable adjuvant. In other aspects of this embodiment, a pharmaceutical composition disclosed herein reduces intestinal irritation by, e.g., at least 5%, at least 10%, at least 20%, at least 30%, at least 40%, at least 50%, at least 60%, at least 70%, at least 80%, at least 90%, or at least 100% when compared to the same pharmaceutical composition disclosed herein, except without the pharmaceutically-acceptable adjuvant. In yet other aspects of this embodiment, a pharmaceutical composition disclosed herein reduces intestinal irritation by, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% when compared to the same pharmaceutical composition disclosed herein, except without the pharmaceutically-acceptable adjuvant.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present invention can also be described as follows:

1. A pharmaceutical composition comprising: a) a therapeutic compound, wherein the therapeutic compound has an anti-pain activity; and b) a pharmaceutically-acceptable adjuvant.
2. The pharmaceutical composition according to embodiment 1, wherein the composition further comprises a pharmaceutically-acceptable solvent.
3. A pharmaceutical composition comprising: a) a therapeutic compound, wherein the therapeutic compound has an anti-pain activity; b) a pharmaceutically-acceptable solvent; and c) a pharmaceutically-acceptable adjuvant.
4. A pharmaceutical composition comprising: a) a therapeutic compound, wherein the therapeutic compound has an anti-pain activity; b) a pharmaceutically-acceptable solvent; and c) a pharmaceutically-acceptable adjuvant, wherein the ratio of the pharmaceutically-acceptable solvent to pharmaceutically-acceptable adjuvant is in a range from about 0:1 to about 1:25.
5. The pharmaceutical composition according to embodiment 2 or 3, wherein the ratio of the pharmaceutically-acceptable solvent to pharmaceutically-acceptable adjuvant is in a range from about 0:1 to about 1:25.
6. The pharmaceutical composition according to embodiments 1-5, wherein the anti-pain activity reduces a severe pain response.
7. The pharmaceutical composition according to embodiment 6, wherein the anti-pain activity reduces a severe pain response by at least 10%.

8. The pharmaceutical composition according to embodiments 1-7, wherein the anti-pain activity reduces a nociceptive pain response.
9. The pharmaceutical composition according to embodiment 8, wherein the anti-pain activity reduces a nociceptive pain response by at least 10%.
10. The pharmaceutical composition according to embodiments 1-7, wherein the anti-pain activity reduces a pain response mediated by a nociceptive receptor.
11. The pharmaceutical composition according to embodiment 10, wherein the anti-pain activity reduces a pain response mediated by a nociceptive receptor by at least 10%.
12. The pharmaceutical composition according to embodiments 1-7, wherein the anti-pain activity reduces a somatic pain response.
13. The pharmaceutical composition according to embodiment 12, wherein the anti-pain activity reduces a somatic pain response by at least 10%.
14. The pharmaceutical composition according to embodiments 1-7, wherein the anti-pain activity reduces a visceral pain response.
15. The pharmaceutical composition according to embodiment 14, wherein the anti-pain activity reduces a visceral pain response by at least 10%.
16. The pharmaceutical composition according to embodiments 1-7, wherein the anti-pain activity reduces a pathological pain response.
17. The pharmaceutical composition according to embodiment 16, wherein the anti-pain activity reduces a pathological pain response by at least 10%.
18. The pharmaceutical composition according to embodiments 1-7, wherein the anti-pain activity reduces a neuropathic pain response.
19. The pharmaceutical composition according to embodiment 18, wherein the anti-pain activity reduces a neuropathic pain response by at least 10%.
20. The pharmaceutical composition according to embodiments 1-7, wherein the anti-pain activity reduces a central neuropathic pain response.
21. The pharmaceutical composition according to embodiment 20, wherein the anti-pain activity reduces a central neuropathic pain response by at least 10%.
22. The pharmaceutical composition according to embodiments 1-7, wherein the anti-pain activity reduces a peripheral neuropathic pain response.
23. The pharmaceutical composition according to embodiment 22, wherein the anti-pain activity reduces a peripheral neuropathic pain response by at least 10%.
24. The pharmaceutical composition according to embodiments 1-7, wherein the anti-pain activity reduces a mononeuropathic pain response.
25. The pharmaceutical composition according to embodiment 24, wherein the anti-pain activity reduces a mononeuropathic pain response by at least 10%.
26. The pharmaceutical composition according to embodiments 1-7, wherein the anti-pain activity reduces a mononeuropathic multiplex pain response.
27. The pharmaceutical composition according to embodiment 26, wherein the anti-pain activity reduces a mononeuropathic multiplex pain response by at least 10%.
28. The pharmaceutical composition according to embodiments 1-7, wherein the anti-pain activity reduces a polyneuropathic pain response.
29. The pharmaceutical composition according to embodiment 28, wherein the anti-pain activity reduces a polyneuropathic pain response by at least 10%.
30. The pharmaceutical composition according to embodiments 1-7, wherein the anti-pain activity reduces an autonomic neuropathic pain response.
31. The pharmaceutical composition according to embodiment 30, wherein the anti-pain activity reduces an autonomic neuropathic pain response by at least 10%.
32. The pharmaceutical composition according to embodiments 1-7, wherein the anti-pain activity reduces a neuralgia pain response.
33. The pharmaceutical composition according to embodiment 32, wherein the anti-pain activity reduces a neuralgia pain response by at least 10%.
34. The pharmaceutical composition according to embodiments 1-7, wherein the anti-pain activity reduces a complex regional pain syndrome pain response.
35. The pharmaceutical composition according to embodiment 34, wherein the anti-pain activity reduces a complex regional pain syndrome pain response by at least 10%.
36. The pharmaceutical composition according to embodiments 1-7, wherein the anti-pain activity reduces a referred pain response.
37. The pharmaceutical composition according to embodiment 36, wherein the anti-pain activity reduces a referred pain response by at least 10%.
38. The pharmaceutical composition according to embodiments 1-7, wherein the anti-pain activity reduces a deafferentation pain response.
39. The pharmaceutical composition according to embodiment 38, wherein the anti-pain activity reduces a deafferentation pain response by at least 10%.
40. The pharmaceutical composition according to embodiments 1-7, wherein the anti-pain activity reduces a dysfunctional pain response.
41. The pharmaceutical composition according to embodiment 38, wherein the anti-pain activity reduces a dysfunctional pain response by at least 10%.
42. The pharmaceutical composition according to embodiments 1-7, wherein the anti-pain activity reduces a headache pain response.
43. The pharmaceutical composition according to embodiment 42, wherein the anti-pain activity reduces a headache pain response by at least 10%.
44. The pharmaceutical composition according to embodiments 1-7, wherein the anti-pain activity reduces a migraine pain response.
45. The pharmaceutical composition according to embodiment 44, wherein the anti-pain activity reduces a migraine pain response by at least 10%.
46. The pharmaceutical composition according to embodiments 1-45, wherein the therapeutic compound has a log P value indicating that the compound is soluble in an organic solvent.
47. The pharmaceutical composition according to embodiments 1-46, wherein the therapeutic compound has a log P value of more than 1.0.
48. The pharmaceutical composition according to embodiments 1-46, wherein the therapeutic compound has a log P value of more than 2.0.
49. The pharmaceutical composition according to embodiments 1-48, wherein the therapeutic compound has a polar surface area that is hydrophobic.
50. The pharmaceutical composition according to embodiments 1-49, wherein the therapeutic compound has a polar surface area that is less than 8.0 nm$^2$.

51. The pharmaceutical composition according to embodiments 1-49, wherein the therapeutic compound has a polar surface area that is less than 6.0 nm$^2$.

52. The pharmaceutical composition according to embodiments 1-51, wherein the therapeutic compound comprises a non-steroidal anti-pain drug (NSAID).

53. The pharmaceutical composition according to embodiment 52, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor or a combination thereof.

54. The pharmaceutical composition according to embodiments 1-53, wherein the therapeutic compound comprises a PPARγ agonist.

55. The pharmaceutical composition according to embodiment 54, wherein the PPARγ agonist comprises Monascin, Irbesartan, Telmisartan, mycophenolic acid, Resveratrol, Delta(9)-tetrahydrocannabinol, a cannabidiol, Curcumin, Cilostazol, Benzbromarone, 6-shogaol, glycyrrhetinic acid, a thiazolidinedione, a NSAID, a fibrate, or a combination thereof.

56. The pharmaceutical composition according to embodiments 1-55, wherein the therapeutic compound comprises a nuclear receptor binding agent.

57. The pharmaceutical composition according to embodiment 56, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.

58. The pharmaceutical composition according to embodiments 1-57, wherein the therapeutic compound comprises an anti-hyperlipidemic agent.

59. The pharmaceutical composition according to embodiment 58, wherein the anti-hyperlipidemic agent comprises a fibrate, a statin, a tocotrienol, a niacin, a bile acid sequestrants (resin), a cholesterol absorption inhibitor, a pancreatic lipase inhibitor, a sympathomimetic amine, or a combination thereof.

60. The pharmaceutical composition according to embodiment 59, wherein the fibrate comprises Bezafibrate, Ciprofibrate, Clofibrate, Gemfibrozil, Fenofibrate, or a combination thereof.

61. The pharmaceutical composition according to embodiment 59, wherein the statin comprises Atorvastatin, Fluvastatin, Lovastatin, Pitavastatin, Pravastatin, Rosuvastatin, Simvastatin, or a combination thereof.

62. The pharmaceutical composition according to embodiment 59, wherein the niacin comprises acipimox, niacin, nicotinamide, vitamin B3, or a combination thereof.

63. The pharmaceutical composition according to embodiment 59, wherein the bile acid sequestrant comprises Cholestyramine, Colesevelam, Colestipol, or a combination thereof.

64. The pharmaceutical composition according to embodiment 59, wherein the cholesterol absorption inhibitor comprises Ezetimibe, a phytosterol, a sterol, a stanol, or a combination thereof.

65. The pharmaceutical composition according to embodiment 59, wherein the fat absorption inhibitor comprises Orlistat 66. The pharmaceutical composition according to embodiment 59, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.

67. The pharmaceutical composition according to embodiments 1-66, wherein the therapeutic compound comprises an ester of a therapeutic compound.

68. The pharmaceutical composition according to embodiments 1-67, wherein the therapeutic compound comprises an ester of a therapeutic compound according to embodiments 52-66.

69. The pharmaceutical composition according to embodiments 1-68, wherein the pharmaceutically-acceptable solvent is less than about 20% (v/v).

70. The pharmaceutical composition according to embodiments 1-69, wherein the pharmaceutically-acceptable solvent comprises a pharmaceutically-acceptable polar aprotic solvent, a pharmaceutically-acceptable polar protic solvent, a pharmaceutically-acceptable non-polar solvent, or a combination thereof.

71. The pharmaceutical composition according to embodiments 1-70, wherein the pharmaceutically-acceptable solvent comprises a pharmaceutically-acceptable alcohol.

72. The pharmaceutical composition according to embodiment 71, wherein the pharmaceutically-acceptable alcohol comprises an acyclic alcohol, a monohydric alcohol, a polyhydric alcohol, an unsaturated aliphatic alcohol, an alicyclic alcohol, or a combination thereof.

73. The pharmaceutical composition according to embodiment 71, wherein the pharmaceutically-acceptable alcohol comprises a $C_{1-20}$ alcohol.

74. The pharmaceutical composition according to embodiment 71, wherein the pharmaceutically-acceptable alcohol comprises methanol, ethanol, propanol, butanol, pentanol, 1-hexadecanol, or a combination thereof.

75. The pharmaceutical composition according to embodiments 1-74, wherein the pharmaceutically-acceptable solvent comprises a pharmaceutically-acceptable ester of pharmaceutically-acceptable alcohol and an acid.

76. The pharmaceutical composition according to embodiment 75, wherein the pharmaceutically-acceptable ester comprises methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate, or a combination thereof.

77. The pharmaceutical composition according to embodiments 1-76, wherein the pharmaceutically-acceptable solvent comprises a pharmaceutically-acceptable glycol ether, a pharmaceutically-acceptable diol, a pharmaceutically-acceptable propylene glycol, a pharmaceutically-acceptable dipropylene glycol, a pharmaceutically-acceptable polypropylene glycol (PPG) polymer, a pharmaceutically-acceptable polyethylene glycol (PEG) polymer, or any combination thereof.

78. The pharmaceutical composition according to embodiment 77, wherein the pharmaceutically-acceptable glycol ether comprises diethylene glycol monomethyl ether (2-(2-methoxyethoxy)ethanol), diethylene glycol monoethyl ether (2-(2-ethoxyethoxy)ethanol), diethylene glycol monopropyl ether (2-(2-propoxyethoxy)ethanol), diethylene glycol monoisopropyl ether (2-(2-isopropoxyethoxy) ethanol), diethylene glycol mono-n-butyl ether (2-(2-butoxyethoxy)ethanol), or any combination thereof.

79. The pharmaceutical composition according to embodiment 77, wherein the pharmaceutically-acceptable polypropylene glycol (PPG) polymer or the pharmaceutically-acceptable polyethylene glycol (PEG) polymer is less than about 2,000 g/mol.

80. The pharmaceutical composition according to embodiment 77, wherein the pharmaceutically-acceptable polypropylene glycol (PPG) polymer or the pharmaceutically-acceptable polyethylene glycol (PEG) polymer is more than about 2,000 g/mol.

81. The pharmaceutical composition according to embodiments 1-51, wherein the pharmaceutically-acceptable solvent comprises a pharmaceutically-acceptable glyceride.

82. The pharmaceutical composition according to embodiment 81, wherein the pharmaceutically-acceptable glyceride comprises a monoglyceride, a diglyceride, a triglyceride, an acetylated monoglyceride, an acetylated diglyceride, an acetylated triglyceride, or a combination thereof.

83. The pharmaceutical composition according to embodiments 1-82, wherein the pharmaceutically-acceptable solvent is a liquid at 20° C. or wherein the pharmaceutically-acceptable solvent is a solid at 20° C.

84. The pharmaceutical composition according to embodiment 83, wherein the pharmaceutically-acceptable solid solvent comprises menthol.

85. The pharmaceutical composition according to embodiments 1-84, wherein the adjuvant is at least 80% (v/v).

86. The pharmaceutical composition according to embodiments 1-85, wherein the pharmaceutically-acceptable adjuvant is a liquid at 20° C.

87. The pharmaceutical composition according to embodiments 1-86, wherein the pharmaceutically-acceptable adjuvant is a solid at 20° C.

88. The pharmaceutical composition according to embodiments 1-87, wherein the pharmaceutically-acceptable adjuvant comprises a pharmaceutically-acceptable lipid.

89. The pharmaceutical composition according to embodiment 88, wherein the pharmaceutically-acceptable lipid comprises a saturated fatty acid, an unsaturated fatty acid, or a combination thereof.

90. The pharmaceutical composition according to embodiment 88 or 89, wherein the pharmaceutically-acceptable lipid comprises two or more saturated or unsaturated fatty acids.

91. The pharmaceutical composition according to embodiment 90, wherein the two or more saturated or unsaturated fatty acids includes palmitic acid, stearic acid, oleic acid, linoleic acid, linolenic acid, or a combination thereof.

92. The pharmaceutical composition according to embodiments 89-91, wherein the unsaturated fatty acid has a melting point temperature of 20° C. or below or wherein the unsaturated fatty acid is a solid at 20° C.

93. The pharmaceutical composition according to embodiments 89-91, wherein the unsaturated fatty acid comprises an omega fatty acid.

94. The pharmaceutical composition according to embodiment 88, wherein the pharmaceutically-acceptable lipid comprises a pharmaceutically-acceptable oil.

95. The pharmaceutical composition according to embodiment 94, wherein the pharmaceutically-acceptable oil comprises almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, theobroma oil, walnut oil, wheat germ oil, or a combination thereof.

96. The pharmaceutical composition according to embodiment 88, wherein the pharmaceutically-acceptable lipid comprises a pharmaceutically-acceptable glycerolipid, a pharmaceutically-acceptable glycol fatty acid ester, a pharmaceutically-acceptable polyether fatty acid ester, a mixture of pharmaceutically-acceptable lipids, or any combination thereof.

97. The pharmaceutical composition according to embodiments 1-96, wherein the pharmaceutical composition further comprises a pharmaceutically-acceptable stabilizing agent.

98. The pharmaceutical composition according to embodiment 97, wherein the pharmaceutically-acceptable stabilizing agent comprises water, a sacrificial acid comprising a fatty acid component and acetic acid, ethyl acetate, sodium acetate/acetic acid, a monoglyceride, an acetylated monoglyceride, a diglyceride, an acetylated diglyceride, a fatty acid, a fatty acid salt, or a combination thereof.

99. The pharmaceutical composition according to embodiment 97, wherein the pharmaceutically-acceptable stabilizing agent comprises a pharmaceutically-acceptable emulsifying agent.

100. The pharmaceutical composition according to embodiment 99, wherein the pharmaceutically-acceptable emulsifying agent comprises a surfactant, a polysaccharide, a lectin, a phospholipid, or a combination thereof.

101. The pharmaceutical composition according to embodiments 1-100, wherein the pharmaceutical composition does not comprise a pharmaceutically-acceptable emulsifying agent.

102. A method of preparing a pharmaceutical composition, the method comprising the step of contacting a therapeutic compound with a pharmaceutically-acceptable adjuvant under conditions which allow the formation of the pharmaceutical composition.

103. A method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-pain activity, and b) contacting the solution formed in step (a) with a pharmaceutically-acceptable adjuvant under conditions which allow the formation of the pharmaceutical composition.

104. A method of preparing a pharmaceutical composition, the method comprising the steps: a) contacting a pharmaceutically-acceptable solvent with a therapeutic compound under conditions which allow the therapeutic compound to dissolve in the pharmaceutically-acceptable solvent, thereby forming a solution, wherein the therapeutic compound has anti-pain activity, and b) contacting the solution formed in step (a) with a pharmaceutically-acceptable adjuvant under conditions which allow the formation of the pharmaceutical composition, wherein the ratio of the pharmaceutically-acceptable solvent to pharmaceutically-acceptable adjuvant is in a range from about 0:1 to about 1:25.

105. The method according to embodiments 102-104, wherein the therapeutic compound has a log P value indicating that the compound is soluble in an organic solvent.

106. The method according to embodiment 102-105, wherein the therapeutic compound has a log P value of more than 1.0.
107. The method according to embodiment 102-105, wherein the therapeutic compound has a log P value of more than 2.0.
108. The method according to embodiments 102-107, wherein the therapeutic compound has a polar surface area that is hydrophobic.
109. The method according to embodiments 102-108, wherein the therapeutic compound has a polar surface area that is less than 8.0 nm$^2$.
110. The method according to embodiments 102-108, wherein the therapeutic compound has a polar surface area that is less than 6.0 nm$^2$.
111. The method according to embodiments 102-110, wherein the therapeutic compound comprises a non-steroidal anti-pain drug (NSAID).
112. The method according to embodiment 111, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a combination thereof.
113. The method according to embodiments 102-112, wherein the therapeutic compound comprises a PPARγ agonist.
114. The method according to embodiment 113, wherein the PPARγ agonist comprises Monascin, Irbesartan, Telmisartan, mycophenolic acid, Resveratrol, Delta(9)-tetrahydrocannabinol, a cannabidiol, Curcumin, Cilostazol, Benzbromarone, 6-shogaol, glycyrrhetinic acid, a thiazolidinedione, a NSAID, a fibrate, or a combination thereof.
115. The method according to embodiments 102-114, wherein the therapeutic compound comprises a nuclear receptor binding agent.
116. The method according to embodiment 115, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.
117. The method according to embodiments 102-116, wherein the therapeutic compound comprises an anti-hyperlipidemic agent.
118. The method according to embodiment 117, wherein the anti-hyperlipidemic agent comprises a fibrate, a statin, a tocotrienol, a niacin, a bile acid sequestrants (resin), a cholesterol absorption inhibitor, a pancreatic lipase inhibitor, a sympathomimetic amine, or a combination thereof.
119. The method according to embodiment 118, wherein the fibrate comprises Bezafibrate, Ciprofibrate, Clofibrate, Gemfibrozil, Fenofibrate, or a combination thereof.
120. The method according to embodiment 118, wherein the statin comprises Atorvastatin, Fluvastatin, Lovastatin, Pitavastatin, Pravastatin, Rosuvastatin, Simvastatin, or a combination thereof.
121. The method according to embodiment 118, wherein the niacin comprises acipimox, niacin, nicotinamide, vitamin B3, or a combination thereof.
122. The method according to embodiment 118, wherein the bile acid sequestrant comprises Cholestyramine, Colesevelam, Colestipol, or a combination thereof.
123. The method according to embodiment 118, wherein the cholesterol absorption inhibitor comprises Ezetimibe, a phytosterol, a sterol, a stanol, or a combination thereof.
124. The method according to embodiment 118, wherein the fat absorption inhibitor comprises Orlistat
125. The method according to embodiment 118, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.
126. The method according to embodiments 102-125, wherein the therapeutic compound comprises an ester of a therapeutic compound.
127. The method according to embodiments 102-126, wherein the therapeutic compound comprises an ester of a therapeutic compound according to embodiments 111-126.
128. The method according to embodiments 103-127, wherein the pharmaceutically-acceptable solvent is less than about 20% (v/v).
129. The method according to embodiments 103-128, wherein the pharmaceutically-acceptable solvent comprises a pharmaceutically-acceptable polar aprotic solvent, a pharmaceutically-acceptable polar protic solvent, a pharmaceutically-acceptable non-polar solvent, or a combination thereof.
130. The method according to embodiments 103-129, wherein the pharmaceutically-acceptable solvent comprises a pharmaceutically-acceptable alcohol.
131. The method according to embodiment 130, wherein the pharmaceutically-acceptable alcohol comprises an acyclic alcohol, a monohydric alcohol, a polyhydric alcohol, an unsaturated aliphatic alcohol, an alicyclic alcohol, or a combination thereof.
132. The method according to embodiment 130, wherein the pharmaceutically-acceptable alcohol comprises a $C_{1-20}$ alcohol.
133. The method according to embodiment 130, wherein the pharmaceutically-acceptable alcohol comprises methanol, ethanol, propanol, butanol, pentanol, 1-hexadecanol, or a combination thereof.
134. The method according to embodiment 130, wherein the pharmaceutically-acceptable solvent comprises a pharmaceutically-acceptable ester of pharmaceutically-acceptable alcohol and an acid.
135. The method according to embodiment 134, wherein the pharmaceutically-acceptable ester comprises methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate, or a combination thereof.
136. The method according to embodiments 103-135, wherein the pharmaceutically-acceptable solvent is a pharmaceutically-acceptable polyethylene glycol (PEG) polymer.

137. The method according to embodiment 136, wherein the pharmaceutically-acceptable polyethylene glycol (PEG) polymer is less than about 2,000 g/mol.
138. The method according to embodiment 136, wherein the pharmaceutically-acceptable polyethylene glycol (PEG) polymer is more than about 2,000 g/mol.
139. The method according to embodiments 103-138, wherein the pharmaceutically-acceptable solvent comprises a pharmaceutically-acceptable glyceride.
140. The method according to embodiments 139, wherein the pharmaceutically-acceptable glyceride is a monoglyceride, a diglyceride, a triglyceride, an acetylated monoglyceride, an acetylated diglyceride, an acetylated triglyceride, or a combination thereof.
141. The method according to embodiments 103-140, wherein the pharmaceutically-acceptable solvent is a liquid at 20° C.
142. The method according to embodiments 103-141, wherein the pharmaceutically-acceptable solvent is a solid at 20° C.
143. The method according to embodiment 142, wherein the pharmaceutically-acceptable solid solvent is menthol.
144. The method according to embodiments 102-143, wherein the pharmaceutically-acceptable adjuvant is at least 80% (v/v).
145. The method according to embodiments 102-144, wherein the pharmaceutically-acceptable adjuvant is a liquid at 20° C.
146. The method according to embodiments 102-144, wherein the pharmaceutically-acceptable adjuvant is a solid at 20° C.
147. The method according to embodiments 102-146, wherein the pharmaceutically-acceptable adjuvant comprises a pharmaceutically-acceptable lipid.
148. The method according to embodiment 147, wherein the pharmaceutically-acceptable lipid comprises a pharmaceutically-acceptable saturated fatty acid, an unsaturated fatty acid, or a combination thereof.
149. The method according to embodiment 147 or 148, wherein the pharmaceutically-acceptable lipid comprises two or more pharmaceutically-acceptable saturated or unsaturated fatty acids.
150. The method according to embodiments 149, wherein the two or more pharmaceutically-acceptable saturated or unsaturated fatty acids include palmitic acid, stearic acid, oleic acid, linoleic acid, linolenic acid, or a combination thereof.
151. The method according to embodiments 148-150, wherein the pharmaceutically-acceptable unsaturated fatty acid has a melting point temperature of 20° C. or below.
152. The method according to embodiments 148-150, wherein the pharmaceutically-acceptable unsaturated fatty acid is a solid at 20° C.
153. The method according to embodiments 148-152, wherein the pharmaceutically-acceptable unsaturated fatty acid comprises an omega fatty acid.
154. The method according to embodiments 147-153, wherein the pharmaceutically-acceptable lipid comprises a pharmaceutically-acceptable oil.
155. The method according to embodiment 154, wherein the pharmaceutically-acceptable oil comprises almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof.
156. The method according to embodiments 103 or 105-155, wherein in step(b) the ratio of the pharmaceutically-acceptable solvent to pharmaceutically-acceptable adjuvant is in a range from about 0:1 to about 1:25.
157. The method according to embodiments 102-156, wherein the step (a) further comprising contacting a pharmaceutically-acceptable stabilizing agent with the pharmaceutically-acceptable solvent and the therapeutic compound.
158. The method according to embodiment 157, wherein the pharmaceutically-acceptable stabilizing agent comprises water, a sacrificial acid comprising a fatty acid component and acetic acid, ethyl acetate, a sodium acetate/acetic acid, a monoglyceride, an acetylated monoglyceride, a diglyceride, an acetylated diglyceride, a fatty acid, a fatty acid salt, or a combination thereof.
159. The method according to embodiment 157 or 158, wherein the pharmaceutically-acceptable stabilizing agent comprises a pharmaceutically-acceptable emulsifying agent.
160. The method according to embodiment 159, wherein the pharmaceutically-acceptable emulsifying agent comprises a surfactant, a polysaccharide, a lectin, a phospholipid, or a combination thereof.
161. The method according to embodiments 102-158, wherein the pharmaceutical composition does not comprise a pharmaceutically-acceptable emulsifying agent.
162. The method according to embodiments 103-161, wherein the method further comprises removing the pharmaceutically-acceptable solvent from the pharmaceutical composition.
163. The method according to embodiment 162, wherein at least 5% the pharmaceutically-acceptable solvent is removed from the pharmaceutical composition.
164. The method according to embodiment 162 or 163, wherein at, removal of solvent from the pharmaceutical composition disclosed herein is carried out at a temperature of less than 20° C.
165. The method according to embodiments 102-164, wherein the pharmaceutical composition made is according to embodiments 1-101.
166 A method of treating an individual with a severe pain condition, the method comprising the step of: administering to the individual in need thereof a pharmaceutical composition according to embodiments 1-101, wherein administration results in a reduction in a symptom associated with the severe pain condition, thereby treating the individual.
167. Use of a pharmaceutical composition according to embodiments 1-101 in the manufacture of a medicament for the treatment of a chronic inflammation.
168. Use of a pharmaceutical composition according to embodiments 1-101 for the treatment of a severe pain condition.
169. The method according to embodiment 166 or the use according to embodiment 167 or 168, wherein the severe pain condition is an acute pain, a subacute pain, or a chronic pain.
170. The method according to embodiment 166 or the use according to embodiment 167 or 168, wherein the severe pain condition is a nociceptive pain.

171. The method or use according to embodiment 170, wherein the nociceptive pain is a visceral pain, a deep somatic pain, a superficial somatic pain, or any combination thereof.

172. The method according to embodiment 166 or the use according to embodiment 167 or 168, wherein the severe pain condition is a pathological pain.

173. The method or use according to embodiment 172, wherein the pathological pain is a neuropathic pain, a dysfunctional pain, or any combination thereof.

174. The method or use according to embodiment 173, wherein the neuropathic pain is a central neuropathic pain, a peripheral neuropathic pain, a deafferentation pain, or any combination thereof.

175. The method or use according to embodiment 174, wherein the peripheral neuropathic pain is a mononeuropathy, a mononeuropathic multiplex, a polyneuropathy, or an autonomic neuropathy.

176. The method or use according to embodiment 175, wherein the polyneuropathy is a distal axonopathy, a myelinopathy, or a neuronopathy.

177. The method or use according to embodiment 174, wherein the peripheral neuropathic pain is a neuralgia or a complex regional pain syndrome.

178. The method according to embodiment 166 or the use according to embodiment 167 or 168, wherein the severe pain condition is a referred pain.

179. The method according to embodiment 166 or the use according to embodiment 167 or 168, wherein the severe pain condition is a headache.

180. The method or use according to embodiment 179, wherein the headache is a muscular/myogenic headache, a vascular headache, a traction headache, inflammatory headache, a chronic sinusitis headache, a hormone headache, a rebound headache, an organic headache, or an ictal headache.

181. The method according to embodiment 166 or the use according to embodiment 167 or 168, wherein the severe pain condition is a migraine.

182. The method according to embodiments 166 or 169-181 or the use according to embodiments 167-181, wherein upon administration to an individual, the pharmaceutical composition comprising the therapeutic compound according to embodiments 1-101 results in a bio-distribution of the therapeutic compound different than a bio-distribution of the therapeutic compound included in the same pharmaceutical composition, except without the pharmaceutically-acceptable adjuvant.

183. The method according to embodiments 166 or 169-182 or the use according to embodiments 167-182, wherein upon administration to an individual, the amount of the therapeutic compound of the pharmaceutical composition according to embodiments 1-101 delivered to a macrophage is at least 5% of the total amount of the therapeutic compound contained in the administered pharmaceutical composition.

184. The method according to embodiments 166 or 169-183 or the use according to embodiments 167-183, wherein upon administration to an individual, the pharmaceutical composition according to embodiments 1-101 reduces intestinal irritation by at least 5% when compared to the pharmaceutical composition according to embodiments 1-101, except without the pharmaceutically-acceptable adjuvant.

185. The method according to embodiments 166 or 169-184 or the use according to embodiments 167-184, wherein upon administration to an individual, the pharmaceutical composition according to embodiments 1-101 reduces gastric irritation by at least 5% when compared to the pharmaceutical composition according to embodiments 1-101, except without the pharmaceutically-acceptable adjuvant.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, alcohols, lipids, pharmaceutical compositions, methods of preparing pharmaceutical compositions, or methods or uses of treating a severe pain condition.

Example 1

Liquid Formulations of Pharmaceutical Composition

This example illustrates how to make a pharmaceutical composition as disclosed herein as a liquid formulation.

Initially, 2,400 mg of ibuprofen was contacted directly with 2.0 mL of rapeseed oil in an attempt to dissolve a therapeutic compound directly into an adjuvant at a concentration of 1,200 mg/mL. However, ibuprofen remained insoluble in the oil and did not dissolve to substantially measureable degree. Ibuprofen remained insolubility even if the mixture was mixed by vortexing for 20 seconds, the contacting was done at 20° C. or 37° C., and/or the mixture was allowed to incubate for 24 hours at 20° C. or 37° C. The insolubility of ibuprofen in rapeseed oil was surprising given that ibuprofen has a log P value of 3.6; such a high log P value is indicative of a compound that would readily soluble in an adjuvant like oil.

Since, it was not possible to dissolve ibuprofen directly into oil, despite its high log P value, it was next tried to dissolve a therapeutic drug in a solvent to first create a solution comprising the compound. As a first step, experiments were conducted to the miscibility of a solvent in an adjuvant like oil in the absence of a therapeutic compound. In these experiments 0.5 mL ethanol was contacted with ten different volumes of rapeseed oil (Table 1). Each mixture was tested at 22° C. and at 37° C. in which the ethanol and oil were initially heated in a water bath before being mixed together. Mixing was attempted by vortex mixing for 20 seconds, and the containers were allowed to settle before visual assessment, either immediately, or after 24 hours. Each mixture was evaluated to determine whether or not the ethanol and rapeseed oil form immiscible layers, or a homogeneous mixture. The results are summarized in Table 1. Mixtures comprising solvent:adjuvant ratios of 1:1, 1:2, 1:3, 1:4, 1:5, and 1:6 formed immiscible layers at either 22° C. or at 37° C., either immediately or after 24 hours of incubation, indicating that the ethanol and oil did not mix well at these ratios. However, in solvent:adjuvant ratios above 1:7 a homogeneous mixture was formed under all conditions tested.

TABLE 1

Liquid Formulations without Therapeutic Compound

| Components | | | Temperature | | | |
|---|---|---|---|---|---|---|
| Solvent | Adjuvant | | 22° C. | | 37° C. | |
| (mL) | (mL) | Ratio | Immediate | 24 hours | Immediate | 24 hours |
| 0.5 | 0.5 | 1:1 | IL | IL | IL | IL |
| 0.5 | 1.0 | 1:2 | IL | IL | IL | IL |
| 0.5 | 1.5 | 1:3 | IL | IL | IL | IL |
| 0.5 | 2.0 | 1:4 | IL | IL | IL | IL |
| 0.5 | 2.5 | 1:5 | IL | IL | IL | IL |
| 0.5 | 3.0 | 1:6 | IL | IL | IL | IL |
| 0.5 | 3.5 | 1:7 | HM | HM | HM | HM |
| 0.5 | 4.0 | 1:8 | HM | HM | HM | HM |
| 0.5 | 4.5 | 1:9 | HM | HM | HM | HM |
| 0.5 | 5.0 | 1:10 | HM | HM | HM | HM |

IL, Immiscible layers.
HM, Homogeneous mixture.

Once the appropriate ratios of alcohol and lipid necessary to form a homogenous mixture were determined, it was next determined whether contacting a therapeutic compound first in a solvent before contacting with an adjuvant would result in the compound dissolving in the solvents. To conduct these experiments, either 1,000 mg or 1,200 mg of ibuprofen was dissolved into 0.5 mL of ethanol. The resulting alcohol solution was then contacted with rapeseed oil at two different solvent:adjuvant ratios (1:2 and 1:9). Each mixture was tested at 20° C. and at 37° C. in which the ethanol solution and oil were initially heated in a water bath before being mixed together. Mixing was attempted by vortex mixing for 20 seconds, and the containers were allowed to settle before visual assessment, either immediately, or after 24 hours. Each mixture was evaluated to determine whether or not the ethanol solution and rapeseed oil form immiscible layers, or a homogeneous mixture. The results are summarized in Table 2. In contrast to the situation in the absence of a therapeutic compound, when ibuprofen is present in the ethanol, it caused the ethanol and oil to form a homogeneous mixture under all conditions tested in solvent:adjuvant ratios above 1:2. This observation was very surprising because, although not wish to be bound by any theory, it appears that a therapeutic compound may be having some effect on the manner in which an adjuvant and solvent interact with each other, such that a homogeneous mixture is formed in a way that does not occur when the therapeutic compound is absent. In addition, the results indicate that a therapeutic compound can be formulated at clinically useful concentrations.

TABLE 2

Liquid Formulations with Therapeutic Compound

| Components | | | | Temperature | | | |
|---|---|---|---|---|---|---|---|
| Compound | Solvent | Adjuvant | | 22° C. | | 37° C. | |
| (mg) | (mL) | (mL) | Ratio | Immediate | 24 hours | Immediate | 24 hours |
| 500 | 0.5 | 1.0 | 1:2 | HM | HM | HM | HM |
| 600 | 0.5 | 1.0 | 1:2 | HM | HM | HM | HM |
| 500 | 0.5 | 4.5 | 1:9 | HM | HM | HM | HM |
| 600 | 0.5 | 4.5 | 1:9 | HM | HM | HM | HM |

IL, Immiscible layers.
HM, Homogeneous mixture.

Example 2

Liquid Formulations of Pharmaceutical Composition

This example illustrates how to make a pharmaceutical composition as disclosed herein as a liquid formulation.

To prepare a pharmaceutical composition disclosed herein using gemfibrozil, the following formulations were examined. In these experiments, 600 mg gemfibrozil was contacted with different volumes of ethanol, as the solvent, warmed to 37° C., and the resulting solution was then contacted with different volumes of linseed oil, as the adjuvant, warmed to 37° C. (Table 3). Each formulation was evaluated to determine whether or not the ethanol and linseed oil form immiscible layers, a clear homogeneous mixture, as well as whether or not the gemfibrozil crystallized out of solution. The results are summarized in Table 3.

Like ibuprofen in Example 1 above, gemfibrozil remained insoluble in the oil alone and did not dissolve to substantially measureable degree. The formulation comprising 0.2 mL ethanol was unable to completely dissolve gemfibrozil. In addition, although the formulation comprising 0.3 mL ethanol was capable of dissolving gemfibrozil, the therapeutic compound began to crystallizing out of solution within 3 hours and complete crystallization occurred within 48 hours. All other formulations tested were capable of dissolving gemfibrozil and forming a pharmaceutical composition disclosed herein. However, only the formulation comprising 0.5 mL ethanol appeared to for a stable pharmaceutical composition in that gemfibrozil remained completely dissolved after three weeks.

TABLE 3

Liquid Formulations with Therapeutic Compound

| Components | | | | Temperature | |
|---|---|---|---|---|---|
| Compound | Solvent | Adjuvant | | 22° C. | |
| (mg) | (mL) | (mL) | Ratio | Immediate | 3 weeks |
| 600 | 0 | 1.0 | — | IM | N/A |
| 600 | 0.2 | — | — | IM | N/A |
| 600 | 0.3 | 0.6 | 1:2 | CR | CR |
| 600 | 0.4 | 0.4 | 1:1 | HM | CR |
| 600 | 0.4 | 0.8 | 1:2 | HM | CR |
| 600 | 0.5 | 1.0 | 1:2 | HM | HM |

HM, Clear homogeneous mixture.
CR, Crystallization.
IM, Immiscible.

Example 3

Liquid Formulations of Pharmaceutical Compositions

This example illustrates how to make a pharmaceutical composition as disclosed herein as a liquid formulation.

To prepare a liquid pharmaceutical composition disclosed herein using ibuprofen, the following method was performed. About 4 g ibuprofen was contacted with 3.6 mL of ethyl acetate, as the solvent, and the resulting solution was then contacted with 76.4 mL of rapeseed oil, as the adjuvant. The resulting pharmaceutical composition had a solvent: adjuvant ratio of about 1:21. This pharmaceutical composition was then placed in a round bottom flask and subjected to low pressure on a rotary evaporator. The temperature was kept low and evaporation continued to constant weight. The total volume lost was 3.65% of the total weight. The resulting liquid no longer retained the characteristic ethyl acetate odor/taste, indicating that there was a substantial removal of ethyl acetate form the pharmaceutical composition.

To prepare a liquid pharmaceutical composition disclosed herein using ibuprofen, the following method was performed. About 2 g ibuprofen was contacted with 1.2 mL of diethylene glycol monoethyl ether (2-(2-ethoxyethoxy)ethanol), as the solvent, 2.2 mL MAISINE® 35-1 (Gattefosse), a glyceryl monolinoleate, and 2.2 mL rapeseed oil, as the adjuvants, and the resulting mixture was then contacted with 0.46 mL isopropanol. The mixture was added to a vessel heated to about 40° C. to about 50° C. and stirred until all components of the mixture dissolved and then cooled to about 30° C. The resulting pharmaceutical composition had a solvent:adjuvant ratio of about 1:3.67. This pharmaceutical composition was then aliquoted to produce 10 liquid capsules each containing about 200 mg ibuprofen.

Example 4

Solid Formulation of Pharmaceutical Composition

This example illustrates how to make a pharmaceutical composition as disclosed herein as a solid formulation.

Since certain fatty acids are liquid at room temperature, while others are solid, an examination of the different fatty acids was undertaken in an effort to evaluate the potential of each fatty acid in the manufacture of a solid formulation. This understanding would enable the development of a wide array of solid formulation by adjusting the relative ratios of each fatty acid. As an initial experiment, linolenic acid, linoleic acid, palmitic acid and stearic acid were evaluated to assess whether it was possible to prepare a pharmaceutical composition disclosed herein that could be formulated using only one of these fatty acids to be a solid or semi-solid at 22° C. (simulating room temperature conditions), but melt into a liquid at 37° C. (simulating internal body temperature conditions after ingestion).

Four different test formulations were prepared and evaluated on their ability to form a solid dose formulation at 22° C. and melt into a homogeneous solution at 37° C. without forming a suspension (Table 4). Formulation 1 was prepared by dissolving 200 mg of Ibuprofen into 400 mg of menthol, and the resulting solution was then mixed with 200 mg of stearic acid ($T_m$ of about 67-72° C.) and heated at 60° C. for 30 minutes to form a homogeneous solution. Formulation 1 solidified immediately upon cooling to 22° C. Formulation 1 remained a solid even after incubating at 37° C. overnight. Formulation 2 was prepared by dissolving 200 mg of Ibuprofen into 400 mg of menthol, and the resulting solution was then mixed with 200 mg of palmitic acid ($T_m$ of about 61-62° C.) and heated at 60° C. for 30 minutes to form a homogeneous solution. Formulation 2 solidified about 1 hour after cooling to 22° C. Incubating at 37° C. overnight cause Formulation 2 to completely melt into a clear homogenous liquid. However, Formulation 2 once again solidified about 1 hour after cooling to 22° C. Formulation 3 was prepared by dissolving 200 mg of Ibuprofen into 400 mg of menthol, and the resulting solution was then mixed with 200 mg of linoleic acid ($T_m$ of about −5° C.) and heated at 37° C. for 2 hours to form a homogeneous solution. Formulation 3 remained a liquid, even after cooling to 22° C. for 72 hours. Formulation 4 was prepared by dissolving 200 mg of Ibuprofen into 400 mg of menthol, and the resulting solution was then mixed with 200 mg of linolenic acid ($T_m$ of about −11° C.) and heated at 37° C. for 2 hours to form a homogeneous solution. Formulation 4 remained a liquid, even after cooling to 22° C. for 72 hours.

TABLE 4

Solid Formulations with Therapeutic Compound

| Components | | | | Temperature | | |
| --- | --- | --- | --- | --- | --- | --- |
| Compound | Solvent | Adjuvant | | 22° C. | | 37° C. |
| (mg) | (mg) | (mg) | Ratio | Upon Cooling | 24 hours | 72 hours |
| 200 | 400 | 200 (stearic acid) | 2:1 | Solid | Solid | — |
| 200 | 400 | 200 (palmitic acid) | 2:1 | Solid | Liquid | — |
| 200 | 400 | 200 (linoleic acid) | 2:1 | Liquid | Liquid | Liquid |
| 200 | 400 | 200 (linolenic acid) | 2:1 | Liquid | Liquid | Liquid |

Based on these data, a solid dosage form of a pharmaceutical composition disclosed herein can be made. For example, a pharmaceutical composition will be formulated to be solid or semi-solid at 22° C., but melt into a proper clear solution (and not a suspension) at 37° C. (Table 5).

TABLE 5

Solid Formulations of Pharmaceutical Compositions

| | |
| --- | --- |
| Compound | 600 mg Ibuprofen |
| Solvent | 500 mg Methanol |
| Adjuvant | 2000 mg Palmitic acid |
| | 2000 mg Stearic acid |
| | 250 mg Linolenic acid |
| | 250 mg Linoleic acid |
| Ratio | 1:9 |
| Volume | 5 mL |
| Concentration | 120 mg/mL |

To prepare a solid pharmaceutical composition disclosed herein using ibuprofen, the following method was performed. About 15 g ibuprofen was contacted with about 9.0 mL of diethylene glycol monoethyl ether (2-(2-ethoxyethoxy)ethanol), as the solvent, about 33 g GELUCIRE® 39/01 (Gattefosse), a waxy solid having a melting point of between 37° C. to 41° C. and comprising a mixture of saturated $C_{10}$-$C_{18}$ triglycerides, as the adjuvant, and about 3.6 mL isopropanol. The mixture was added to a vessel heated to about 40° C. to about 50° C. and stirred until all components of the mixture dissolved, cooled to about 30° C., and then aliquoted by poring into molds and cooled to room temperature. The resulting pharmaceutical composition had a solvent:adjuvant ratio of about 1:3.67. This pharmaceutical composition produced 75 solid tablets each containing about 200 mg ibuprofen.

To prepare a solid pharmaceutical composition disclosed herein using ibuprofen, the following method was performed. About 20 g ibuprofen was contacted with about 12.0 mL of diethylene glycol monoethyl ether (2-(2-ethoxyethoxy)ethanol), as the solvent, about 16 g GELUCIRE® 43/01 (Gattefosse), a waxy solid having a melting point of between 41° C. to 45° C. and comprising a mixture of saturated $C_{10}$-$C_{18}$ triglycerides, and about 16 g MAISINE® 35-1 (Gattefosse), a glyceryl monolinoleate, as the adjuvant, and about 3.6 mL isopropanol. The mixture was added to a vessel heated to about 40° C. to about 50° C. and stirred until all components of the mixture dissolved, cooled to about 30° C., and then aliquoted by poring into molds and cooled to room temperature. The resulting pharmaceutical composition had a solvent:adjuvant ratio of about 1:2.67. This pharmaceutical composition produced 100 solid tablets each containing about 200 mg ibuprofen.

To prepare a solid pharmaceutical composition disclosed herein using ibuprofen, the following method was performed. About 80 g ibuprofen, about 152 g GELUCIRE® 43/01 (Gattefosse), a waxy solid having a melting point of between 41° C. to 45° C. and comprising a mixture of saturated $C_{10}$-$C_{18}$ triglycerides, and about 72 mL MAISINE® 35-1 (Gattefosse), a glyceryl monolinoleate, and about 32 mL PEG 400 were added to a vessel heated to about 50° C. to about 60° C. and stirred until all components of the mixture dissolved. The heated mixture is cooled to about 40° C., and then aliquoted by poring into molds and cooled to room temperature. This pharmaceutical composition produced 400 solid tablets each containing about 200 mg ibuprofen.

To prepare a solid pharmaceutical composition disclosed herein using ibuprofen, the following method was performed. About 1.1 g ibuprofen sodium salt, about 1.9 g GELUCIRE® 43/01 (Gattefosse), a waxy solid having a melting point of between 41° C. to 45° C. and comprising a mixture of saturated $C_{10}$-$C_{18}$ triglycerides, and about 0.9 mL MAISINE® 35-1 (Gattefosse), a glyceryl monolinoleate, about 0.4 mL PEG 400, and about 0.3 mL propylene glycol were added to a vessel heated to about 50° C. to about 60° C. and stirred until all components of the mixture dissolved. The heated mixture is cooled to about 40° C., and then aliquoted by poring into molds and cooled to room temperature. This pharmaceutical composition produced 5 solid tablets each containing about 200 mg ibuprofen.

To prepare a solid pharmaceutical composition disclosed herein using ibuprofen, the following method was performed. About 5 g ibuprofen free acid, about 5 g ibuprofen sodium salt, about 3 g GELUCIRE®43/01 (Gattefosse), a waxy solid having a melting point of between 41° C. to 45° C. and comprising a mixture of saturated $C_{10}$-$C_{18}$ triglycerides, and about 8 mL MAISINE® 35-1 (Gattefosse), a glyceryl monolinoleate, about 3 mL PEG 400, and about 1 mL propylene glycol were added to a vessel heated to about 50° C. to about 60° C. and stirred until all components of the mixture dissolved. The heated mixture is cooled to about 40° C., and then aliquoted by poring into molds and cooled to room temperature. This pharmaceutical composition produced 50 solid tablets each containing about 200 mg ibuprofen.

Example 5

Semi-Solid Formulation of Pharmaceutical Composition

This example illustrates how to make a pharmaceutical composition as disclosed herein as a semi-solid formulation useful for topical administration.

To prepare a semi-solid pharmaceutical composition disclosed herein using ibuprofen, the following method was performed. About 1 g ibuprofen free acid, about 0.2 g ibuprofen sodium salt, about 0.6 g GELUCIRE®43/01 (Gattefosse), a waxy solid having a melting point of between 41° C. to 45° C. and comprising a mixture of saturated $C_{10}$-$C_{18}$ triglycerides, and about 1.6 mL MAISINE® 35-1 (Gattefosse), a glyceryl monolinoleate, about 0.6 mL PEG 400, and about 0.15 mL propylene glycol were added to a vessel heated to about 50° C. to about 60° C. and stirred until all components of the mixture dissolved. The heated mixture is cooled to room temperature and aliquoited into an appropriate container. This pharmaceutical composition produced a semisolid oinment having a concentration of ibuprofen that is about 400 mg/mL.

To prepare a semi-solid pharmaceutical composition disclosed herein using ibuprofen, the following method was performed. About 5 g ibuprofen free acid, about 5 g ibuprofen sodium salt, about 3 g GELUCIRE®43/01 (Gattefosse), a waxy solid having a melting point of between 41° C. to 45° C. and comprising a mixture of saturated $C_{10}$-$C_{18}$ triglycerides, and about 8 mL MAISINE® 35-1 (Gattefosse), a glyceryl monolinoleate, about 3 mL PEG 400, and about 1 mL propylene glycol were added to a vessel heated to about 50° C. to about 60° C. and stirred until all components of the mixture dissolved. The heated mixture is cooled to room temperature and aliquoited into an appropriate container. This pharmaceutical composition produced a semisolid oinment having a concentration of ibuprofen that is about 650 mg/mL.

Example 6

Animal Model for Intestinal Erosion

To assess whether a pharmaceutical composition disclosed herein reduced gastric irritation, experiments were conducted using an intestinal erosion murine model.

Sprague-Dawley rats were divided into seven experimental groups containing five animals each. After fasting overnight, the animals were challenged with one with one of seven different treatments. Group A was a control in which each mouse was orally administered 1% methylcellulose/0.5% polysorbate 80 vehicle only. Group B was a control in which each mouse was orally administered solvent/adjuvant vehicle only (gavage of 10% ethanol and 90% linseed oil). Group C was a control in which each mouse was orally administered 150 mg/kg aspirin. Group D was a control in which each mouse was orally administered 100 mg/kg ibuprofen suspended in 1% methylcellulose/0.5% polysorbate 80. Group E was the experimental group in which each mouse was administered a pharmaceutical composition disclosed herein (BC1054-100) comprising 100 mg/kg of ibuprofen, 10% ethanol, and 90% linseed oil. Group F was a control in which each mouse was orally administered 100 mg/kg ibuprofen suspended in 1% methylcellulose/0.5% polysorbate 80. Group G was the experimental group in which each mouse was administered a pharmaceutical composition disclosed herein (BC1054-200) comprising 200 mg/kg of ibuprofen, 10% ethanol, and 90% linseed oil. Animals were sacrificed 4 hours after treatment and the stomachs were examined for degree of hemorrhage and severity of mucosal erosive lesions. Gastric irritation was scored as follows: 0, no lesions; 1, hyperemia; 2, one or two slight lesions; 3, more than two slight lesions or severe lesions; and 4, very severe lesions. A score of 50% or more relative to Group C (aspirin-treated control group), which was set to 100%, was considered a positive score for gastric irritation.

Results are shown in Table 6. Group D (100 mg/kg of ibuprofen-treated control group) and Group F (200 mg/kg of ibuprofen-treated control group) produced gastric lesions that were 75% and 95%, respectively, severe as those induced by Group C (aspirin-treated control group). However, Group E (BC1054-100-treated experimental group) and Group G (BC1054-200-treated experimental group) produced gastric lesions that were 20% and 40%, respectively, as severe as those associated with Group C (aspirin-treated control group). These results demonstrate that that a pharmaceutical composition disclosed herein reduced the extent to which a therapeutic compound may cause mucosal lesions and cause gastric irritation.

TABLE 6

Results from Intestinal Erosion Assay

| Group | Mean Ulceration Score | % Aspirin Erosion |
|---|---|---|
| A | 0 | 0 |
| B | 0 | 0 |
| C | 4 | (100) |
| D | 3 | 75[1] |
| E | 0.8 | 20 |
| F | 3.8 | 95[1] |
| G | 1.6 | 40 |

[1]Positive score for gastric erosion.

Example 7

Case Studies for the Treatment of Severe Pain

A 51 year old male experienced severe dental pain due to the exposure of a nerve after a tooth filling disintegrated. The pain was perceived to be too severe to be controlled by ibuprofen or diclofenac, but the patient was reluctant to use codeine (30 mg) with paracetamol (500 mg) which was available to him. Prior to the patient coming into to see the dentist for remedial dental work, he took 7 day course of a pharmaceutical composition disclosed herein (BC1054) comprising 20 mg/kg of ibuprofen, 10% ethanol, and 90% rapeseed oil (800 mg b.id), which effectively controlled the pain. Relief of pain occurred within 30 minutes of taking each dose and lasted for approximately 12 hours before redosing. The pain control was so good that he was no longer aware of pain in the affected tooth.

A 50 year old male was diagnosed with a maison neuve fracture in the ankle after a sport injury. The patient was initially administered 30 mg codeine with 500 mg paracetamol bid, along with 10 mg diclofenac tid for 8 months to control his severe pain. After experiencing unacceptable side effects he ceased opiate paracetamol and diclofenac therapy and commenced a 5 day course of a pharmaceutical composition disclosed herein (BC1054) comprising 20 mg/kg of ibuprofen, 10% ethanol, and 90% rapeseed oil (600 mg bid). After 2 days reported a significant improvement in his pain, and then after 3 days he reported that the pain was completely controlled. After a 2 month follow the patient is still free of severe pain and he has since resumed an active sporting life.

Example 8

Treatment of a Severe Pain Condition

A 62 year old female complains of severe lower back pain after lifting a heavy box the day before. A physician determines that the lower pain is due to an acute pain. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates there is reduced pain. At one and three week check-ups, the woman indicates that she continues to have reduced pain. This reduction in acute pain symptoms indicates successful treatment with the pharmaceutical composition disclosed herein. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 22 year old male complains of severe pain in his right shoulder that occurred while he was lifting weighs in the gym one month ago. A physician determines that the severe pain is a subacute pain. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is improvement in his ability to move his arm without pain in his shoulder. At one week and one and three month check-ups, the man indicates that he continues to have improved shoulder mobility and no pain. This reduction in subacute pain symptoms indicates successful treatment with the pharmaceutical composition disclosed herein. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 67 year old male complains of severe pain in his ankle from a fall he took two months before. A physician determines that the pain is a chronic pain. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced pain in his ankle and mobility in his ankle is better. At one and three month check-ups, the man indicates that he continues to have improved ankle mobility and no pain. This reduction in chronic pain symptoms indicates successful treatment with the pharmaceutical composition disclosed herein. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 73 year old female complains of severe pain after burning her forearm on a hot oven. A physician determines that the pain is due to superficial somatic nociceptive pain. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that she no longer feels pain in her forearm. At one and three week check-ups, the woman indicates that she still feels no pain. This reduction in superficial somatic noceceptive pain symptoms indicates successful treatment with the pharmaceutical composition disclosed herein. A similar type of oral administration of a pharmaceutical composition disclosed herein will be used to treat a patient suffering from severe pain associated with any other deep somatic noceceptive pain, including, without limitation, an excessive muscle tension, a repetitive motion disorder, a muscle disorder, a myalgia, an infection, and a drug-induced pain. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 37 year old male complains of severe pain due to a lower leg bone fracture while skiing. A physician determines that the pain is due to deep somatic noceceptive pain. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced pain in his leg. At one and two month check-ups, the man indicates that he continues to have reduced pain. This reduction in deep somatic noceceptive pain symptoms indicates successful treatment with the pharmaceutical composition disclosed herein. A similar type of oral administration of a pharmaceutical composition disclosed herein will be used to treat a patient suffering from severe pain associated with any other deep somatic noceceptive pain, including, without limitation, an excessive muscle tension, a repetitive motion disorder, a muscle disorder, a myalgia, an infection, and a drug-induced pain. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 33 year old female complains of chronic abdominal pain. A physician determines that the pain is due to deep visceral noceceptive pain. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that there is a reduction in abdominal pain. At one and three month check-ups, the woman indicates that she continues to have reduced abdominal pain. This reduction in deep visceral noceceptive pain symptoms indicates successful treatment with the pharmaceutical composition disclosed herein. A similar type of oral administration of a pharmaceutical composition disclosed herein will be used to treat a patient suffering from severe pain associated with any other deep visceral noceceptive pain, including, without limitation, a functional visceral pain, a chronic gastrointestinal inflammation, an autoimmune pain, an organic visceral pain, and a treatment-induced visceral pain. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 66 year old male complains of severe pain after suffering a stroke. A physician determines that the pain is due to central neuropathic pain. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates that there is a reduction in abdominal pain. At one and three month check-ups, the man indicates that he continues to have reduced pain. This reduction in central neuropathic pain symptoms indicates successful treatment with the pharmaceutical composition disclosed herein. A similar type of oral administration of a pharmaceutical composition disclosed herein will be used to treat a patient suffering from severe pain associated with any other central neuropathic or dysfunctional pain, including, without limitation, cerebral venous thrombosis, cerebral tumors or abscesses compressing a brain portion, traumatic brain or spinal cord injury, complications following brain or spinal surgery, multiple sclerosis, and Parkinson disease, ischemic lesions, syringomyelia, radiation myelopathy, and HIV myelopathy. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 58 year old male, who is a diabetic, complains of severe pain. A physician determines that the pain is due to peripheral neuropathic pain from diabetic neuropathy. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduction in the pain. At one and three month check-ups, the man indicates that he still experiences reduced pain. This reduction in a peripheral neuropathic pain indicates successful treatment with the pharmaceutical composition disclosed herein. A similar type of oral administration of a pharmaceutical composition disclosed herein will be used to treat a patient suffering from severe pain associated with any other peripheral neuropathic or dysfunctional pain, including, without limitation, systemic diseases, metabolic disorders, nutrient disorders, drug-induced disorders, traumatic and entrapment syndromes, complications following surgery, distal axonopathy, HIV sensory neuropathy, demyelinating polyradiculoneuropathy, postherpetic neuralgia, nerve root avulsions, cranial neuralgias like trigeminal neuralgia, neuropathic cancer pain, compression of peripheral nerves, nerve plexuses, and nerve roots, paraneoplastic peripheral neuropathy, ganglionopathy, complication of cancer therapies like chemotherapy, radiation, and surgery, and complex regional pain syndrome like Type 1 and Type 2. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 59 year old female complains of severe pain by even the faintest amount of pressure is applied to her forearm. A physician determines that the pain is due to allodynia. The woman is treated by topical administration a pharmaceutical composition comprising ibuprofen as disclosed herein taken twice daily. Alternatively, the woman is treated by topical administration a pharmaceutical composition comprising aspirin as disclosed herein taken thrice daily. Alternatively, the woman is treated by topical administration a pharmaceutical composition comprising naproxen as disclosed herein taken twice daily. The woman's condition is monitored and after about 3 days of treatment the woman indicates there is reduced pain. At one and three month check-ups, the woman indicates that she continues to have reduced pain. This reduction in allodynia symptoms indicates successful treatment with the pharmaceutical composition disclosed herein. A similar type of topical administration of a pharmaceutical composition disclosed herein will be used to treat a patient suffering from severe pain associated with any dysesthesia, such as, e.g., hyperalgesia or hyperpathia. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 47 year old female complains of severe pain down her left leg when she leans over to do the dishes. A physician determines that the leg pain is due to a sciatic nerve dysfunction. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates there is reduced pain. At one and three month check-ups, the woman indicates that she continues to have reduced pain in her leg. This reduction in sciatic nerve dysfunction symptoms indicates successful treatment with the pharmaceutical composition disclosed herein. A similar type of topical administration of a pharmaceutical composition disclosed herein will be used to treat a patient suffering from severe pain associated with any mononeuropathy, such as, e.g., a common peroneal nerve dysfunction. a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome or other focal entrapment neuropathy, and a sixth (abducent) nerve palsy. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 22 year old male complains of severe pain in his right leg that began after a hike in the woods. A physician determines that the severe pain is sue to a Lyme disease. The man is treated by intravenous injection administration of a pharmaceutical composition comprising ibuprofen as disclosed herein taken twice daily. Alternatively, the man is treated by intravenous injection administration of a pharmaceutical composition comprising aspirin as disclosed herein taken thrice daily. Alternatively, the man is treated by intravenous injection administration of a pharmaceutical composition comprising naproxen as disclosed herein taken twice daily. The man's condition is monitored and after about 3 days of treatment the man indicates there is reduced pain. At one week and one and three month check-ups, the man indicates that he continues to no pain. This reduction in Lyme disease symptoms indicates successful treatment with the pharmaceutical composition disclosed herein. A similar type of intravenous injection administration of a pharmaceutical composition disclosed herein will be used to treat a patient suffering from severe pain associated with any mononeuropathic multiplex, such as, e.g., systemic diseases, metabolic disorders, nutrient disorders, drug-induced disorders, traumatic and entrapment syndromes, toxicity, and infections. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 67 year old male, a chronic alcoholic, complains of severe pain. A physician determines that the pain is a polyneuropathy. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced pain. At one and three month check-ups, the man indicates that he continues to have no pain. This reduction in polyneuropathic pain symptoms indicates successful treatment with the pharmaceutical composition disclosed herein. A similar type of oral administration of a pharmaceutical composition disclosed herein will be used to treat a patient suffering from severe pain associated with any other polyneuropathy, including, without limitation, acute inflammatory demyelinating polyneuropathy, chronic inflammatory demyelinating polyneuropathy, and a genetic metabolic disorder. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 73 year old female complains of severe pain in her bladder. A physician determines that the pain is due to an autonomic neuropathy. The woman is treated by instillation administration of a pharmaceutical composition comprising ibuprofen as disclosed herein taken twice daily. Alternatively, the woman is treated by oral administration of a pharmaceutical composition comprising aspirin as disclosed herein taken thrice daily. Alternatively, the woman is treated by oral administration of a pharmaceutical composition comprising naproxen as disclosed herein taken twice daily. The woman's condition is monitored and after about 3 days of treatment the woman indicates that she no longer feels pain in her bladder. At one and three month check-ups, the woman indicates that she still feels no pain. This reduction in autonomic neuropathy symptoms indicates successful treatment with the pharmaceutical composition disclosed herein. A similar type of oral administration of a pharmaceutical composition disclosed herein will be used to treat a patient suffering from severe pain associated with any other autonomic neuropathy affecting any other internal organ. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 42 year old male complains of severe pain whenever any pressure is applied to his left side of his face. A physician determines that the pain is due to a trigeminal neuralgia. The man is treated by topical administration of a pharmaceutical composition comprising ibuprofen as disclosed herein taken twice daily. Alternatively, the man is treated by topical administration a pharmaceutical composition comprising aspirin as disclosed herein taken thrice daily. Alternatively, the man is treated by topical administration a pharmaceutical composition comprising naproxen as disclosed herein taken twice daily. The man's condition is monitored and after about 3 days of treatment the man indicates there is reduced pain in his face. At one and two month check-ups, the man indicates that he continues to have reduced pain. This reduction in trigeminal neuralgia pain symptoms indicates successful treatment with the pharmaceutical composition disclosed herein. A similar type of topical administration of a pharmaceutical composition disclosed herein will be used to treat a patient suffering from severe pain associated with any other neuralgia, including, without limitation, a glossopharyngeal neuralgia, a postherpetic neuralgia, a carpal tunnel syndrome, a meralgia paresthetica, a sciatica and an atypical facial pain. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 54 year old female complains of pain in her left shoulder after suffering a heart-attack. A physician determines that the pain is due to referred pain from a myocardial ischaemia. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that there is a reduction in shoulder pain. At one and three month check-ups, the woman indicates that she continues to have reduced shoulder pain. This reduction in referred pain symptoms indicates successful treatment with the pharmaceutical composition disclosed herein. A similar type of oral administration of a pharmaceutical composition disclosed herein will be used to treat a patient suffering from severe pain associated with any other referred pain, including, without limitation, an intervertebral disc herniation. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 26 year old male complains of severe pain in the location where is amputated arm once was. A physician determines that the pain is due to phantom pain. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates that there is a reduction in pain. At one and three month check-ups, the man indicates that he continues to have reduced pain. This reduction in phantom pain symptoms indicates successful treatment with the pharmaceutical composition disclosed herein. A similar type of oral administration of a pharmaceutical composition disclosed herein will be used to treat a patient suffering from severe pain associated with any other deafferentation pain syndrome, including, without limitation, a brain injury, a spinal cord injury, a lumbar radiculopathy, a post-stroke pain, a paraplegia, avulsion of the brachial plexus or other types of lesions of peripheral nerves, a pathology of the central nervous system. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 58 year old male complains of a headache. The man is treated by oral administration of a pharmaceutical composition comprising ibuprofen as disclosed herein taken twice daily. Alternatively, the man is treated by oral administration of a pharmaceutical composition comprising aspirin as disclosed herein taken thrice daily. Alternatively, the man is treated by oral administration of a pharmaceutical composition comprising naproxen as disclosed herein taken twice daily. The man's condition is monitored and after about 3 hours the headache pain is gone. This elimination in headache pain indicates successful treatment with the pharmaceutical composition disclosed herein. A similar type of oral administration of a pharmaceutical composition disclosed herein will be used to treat a patient suffering from severe pain associated with any other headache pain, including, without limitation, a muscular/myogenic headache, a vascular headache, a traction headache, inflammatory headache, a chronic sinusitis headache, a hormone headache, a rebound headache, an organic headache, and an ictal headache. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 59 year old female complains of severe headache pain. A physician determines that the pain is due to migraine. The woman is treated by oral administration of a pharmaceutical composition comprising ibuprofen as disclosed herein taken twice daily. Alternatively, the woman is treated by topical administration of a pharmaceutical composition comprising aspirin as disclosed herein taken thrice daily. Alternatively, the woman is treated by topical administration of a pharmaceutical composition comprising naproxen as disclosed herein taken twice daily. The woman's condition is monitored and after about 3 days of treatment the woman indicates there is no migraine pain reoccurrence. At one and three month check-ups, the woman indicates that she continues to have reduced frequency and intensity of migraine headache pain. This reduction in migraine symptoms indicates successful treatment with the pharmaceutical composition disclosed herein. A similar type of oral administration of a pharmaceutical composition disclosed herein will be used to treat a patient suffering from severe pain associated with any other migraine headache pain, including, without limitation, a migraine without aura (common migraine), a migraine with aura (classic migraine), a menstrual migraine, a migraine equivalent (acephalic headache), a complicated migraine, an abdominal migraine and a mixed tension migraine. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating an individual with an inflammatory pain, the method comprising the step of: administering to the individual in need thereof a pharmaceutical composition, wherein administration results in a reduction in a symptom associated with the inflammatory pain, thereby treating the individual, and wherein the pharmaceutical composition comprises:
   a) a propionic acid derivative non-steroidal anti-pain drug (NSAID), or a pharmaceutically acceptable salt, solvate, or solvate of a salt thereof, in an amount of about 15% to about 30% of the total weight of the composition;
   b) a pharmaceutically-acceptable liquid polyethylene glycol (PEG) polymer in an amount of about 8% to about 15% of the total weight of the composition; and
   c) a pharmaceutically-acceptable lipid in an amount of at least 50% of the total weight of the composition, the pharmaceutically-acceptable lipid comprising a pharmaceutically-acceptable fat in an amount of at least 30% of the total weight of the composition, the pharmaceutically-acceptable fat comprising a triglyceride, an acetylated triglyceride and/or a triester of glycerol and a pharmaceutically-acceptable monoglyceride in an amount of at least 20% of the total weight of the composition,
   wherein the pharmaceutical composition does not comprise a surfactant, and
   wherein the pharmaceutical composition is formulated to be a solid at a temperature of about 15° C. or lower and have a melting point temperature of about 25 ° C. or higher.

2. The method according to claim 1, wherein the inflammatory pain is an acute pain, a subacute pain, a chronic pain, or any combination thereof.

3. The method according to claim 1, wherein the inflammatory pain is a nociceptive pain, a pathological pain, a referred pain, a headache, or any combination thereof.

4. The method according to claim 3, wherein the nociceptive pain is a visceral pain, a deep somatic pain, a superficial somatic pain, or any combination thereof.

5. The method according to claim 3, wherein the pathological pain is a neuropathic pain, a dysfunctional pain, or any combination thereof.

6. The method according to claim 5, wherein the neuropathic pain is a central neuropathic pain, a peripheral neuropathic pain, a deafferentation pain, or any combination thereof.

7. The method or use according to claim 6, wherein the peripheral neuropathic pain is a mononeuropathy, a mononeuropathic multiplex, a polyneuropathy, or an autonomic neuropathy.

8. The method or use according to claim 7, wherein the polyneuropathy is a distal axonopathy, a myelinopathy, or a neuronopathy.

9. The method or use according to claim 6, wherein the peripheral neuropathic pain is a neuralgia or a complex regional pain syndrome.

10. The method or use according to claim 3, wherein the headache is a muscular/myogenic headache, a vascular headache, a migraine, a traction headache, inflammatory headache, a chronic sinusitis headache, a hormone headache, a rebound headache, an organic headache, or an ictal headache.

11. The method according to claim 1, wherein upon administration to an individual, the pharmaceutical composition comprising the therapeutic compound results in a bio-distribution of the therapeutic compound different than a bio-distribution of the therapeutic compound included in the same pharmaceutical composition, except without the pharmaceutically-acceptable adjuvant.

12. The method according to claim 1, wherein upon administration to an individual, the amount of the therapeutic compound of the pharmaceutical composition delivered to a macrophage is at least 10% of the total amount of the therapeutic compound contained in the administered pharmaceutical composition.

13. The method according to claim 1, wherein upon administration to an individual, the pharmaceutical composition reduces intestinal and/or gastric irritation by at least 10% when compared to the pharmaceutical composition, except without the pharmaceutically-acceptable lipid.

14. The method according to claim 1, wherein the propionic acid derivative NSAID is alminoprofen, benoxaprofen, dexketoprofen, fenoprofen, flurbiprofen, ibuprofen, indoprofen, ketoprofen, loxoprofen, naproxen, oxaprozin, pranoprofen, or suprofen, or a pharmaceutically acceptable salt, solvate, or solvate of a salt thereof.

15. The method according to claim 1, wherein the propionic acid derivative NSAID, or a pharmaceutically acceptable salt, solvate, or solvate of a salt thereof, is in an amount of about 20% to about 30% of the total weight of the composition.

16. The method according to claim 1, wherein the pharmaceutically-acceptable liquid PEG polymer comprises a PEG 100, a PEG 200, a PEG 300, a PEG 400, a PEG 500, a PEG 600, a PEG 700, a PEG 800, a PEG 900, a PEG 1000, or a combination thereof.

17. The method according to claim 1, wherein the pharmaceutically-acceptable liquid PEG polymer is in an amount of about 8% to about 12% of the total weight of the composition.

18. The method according to claim 1, wherein the triglyceride is a mixtures of saturated $C_{10}$-$C_{18}$ triglycerides having a melting point around 43° C.

19. The method according to claim 1, wherein the pharmaceutically-acceptable lipid is in an amount of at least 60% of the total weight of the composition.

20. The method according to claim 19, wherein the pharmaceutically-acceptable fat is in an amount of at least 35% of the total weight of the composition.

21. The method according to claim 1, wherein the pharmaceutically-acceptable monoglyceride is a glyceryl monolinoleate.

* * * * *